(12) United States Patent
Kwong et al.

(10) Patent No.: US 9,997,712 B2
(45) Date of Patent: Jun. 12, 2018

(54) ORGANIC ELECTROLUMINESCENT MATERIALS AND DEVICES

(71) Applicant: Universal Display Corporation, Ewing, NJ (US)

(72) Inventors: Raymond Kwong, Fo Tan (HK); Kit Yee Tsang, Shatin (HK); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 399 days.

(21) Appl. No.: 14/186,607

(22) Filed: Feb. 21, 2014

(65) Prior Publication Data

US 2014/0291638 A1    Oct. 2, 2014

Related U.S. Application Data

(60) Provisional application No. 61/805,611, filed on Mar. 27, 2013.

(51) Int. Cl.
| | |
|---|---|
| H01L 51/50 | (2006.01) |
| H01L 51/00 | (2006.01) |
| C07D 333/50 | (2006.01) |
| C07D 333/76 | (2006.01) |
| C07D 405/04 | (2006.01) |
| C07D 405/10 | (2006.01) |

(Continued)

(52) U.S. Cl.
CPC ........ *H01L 51/0056* (2013.01); *C07D 209/56* (2013.01); *C07D 209/86* (2013.01); *C07D 307/77* (2013.01); *C07D 307/91* (2013.01); *C07D 333/50* (2013.01); *C07D 333/76* (2013.01); *C07D 405/04* (2013.01); *C07D 405/10* (2013.01); *C07D 409/04* (2013.01); *C07D 409/10* (2013.01); *C07D 487/04* (2013.01); *C07D 491/048* (2013.01); *C07D 495/04* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Gregory D Clark
(74) *Attorney, Agent, or Firm* — Duane Morris LLP

(57) ABSTRACT

The present disclosure provides novel compounds containing dibenzo[fg,op]tetracene and larger all-benzenoid moiety that can be used as hosts for phosphorescent emitters providing low-voltage, high-efficiency and high-stability devices.

16 Claims, 2 Drawing Sheets

(51) Int. Cl.
  *C07D 409/04* (2006.01)
  *C07D 409/10* (2006.01)
  *C07D 487/04* (2006.01)
  *C07D 491/048* (2006.01)
  *C07D 495/04* (2006.01)
  *C07D 209/56* (2006.01)
  *C07D 209/86* (2006.01)
  *C07D 307/77* (2006.01)
  *C07D 307/91* (2006.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 5,989,737 A | 11/1999 | Xie et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,183,010 B2 | 2/2007 | Jarikov |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0137239 A1* | 7/2003 | Matsuura ............ H01L 51/5048 313/503 |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0076853 A1* | 4/2004 | Jarikov ................ C09K 11/06 428/690 |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2005/0276994 A1* | 12/2005 | Iwawaki ............. C09K 11/06 428/690 |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0284318 A1 | 11/2008 | Deaton et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

(56) References Cited

OTHER PUBLICATIONS

Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1)162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

This application claims priority to U.S. Provisional Application No. 61/805,611, filed Mar. 27, 2013, the entire content of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to organic materials used in such devices. More specifically, the present invention relates to host compounds for phosphorescent OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

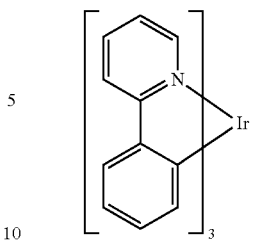

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

The present disclosure provides novel compounds containing dibenzo[fg,op]tetracene and larger all-benzenoid moiety that can be used as hosts for phosphorescent emitters to provide low-voltage, high-efficiency and high-stability devices. They can also be used in OLEDs as emitters, hosts, charge transport materials, in both single color or multiple color devices, materials can be vapor-evaporated or solution processed.

According to an embodiment of the present disclosure, a novel compound having a formula (I), A-L-B (I), wherein A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof, which are optionally further substituted with one or more groups selected from hydrogen, deuterium, alkyl, cycloalkyl, arylalkyl, alkoxy, aryloxy, amino, silyl, aryl, heteroaryl, and combinations thereof;

wherein the substitution of one or more groups in A is optionally fused to the indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group;

wherein L is a single bond or comprises an aryl or heteroaryl group having from 5-30 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof; and wherein B is an all-benzenoid group having at least 24 carbon atoms, which are optionally further substituted with one or more groups selected from hydrogen, deuterium, alkyl, cycloalkyl, arylalkyl, alkoxy, aryloxy, amino, silyl, aryl, heteroaryl, and combinations thereof is disclosed.

According to an aspect of the present disclosure, a device comprising a phosphorescent organic light-emitting device is disclosed. The phosphorescent organic light-emitting device comprising: an anode, a cathode; and an organic layer, disposed between the anode and the cathode, comprising a compound containing an all-benzenoid group having at least 24 carbon atoms disclosed. A formulation comprising the novel compound is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
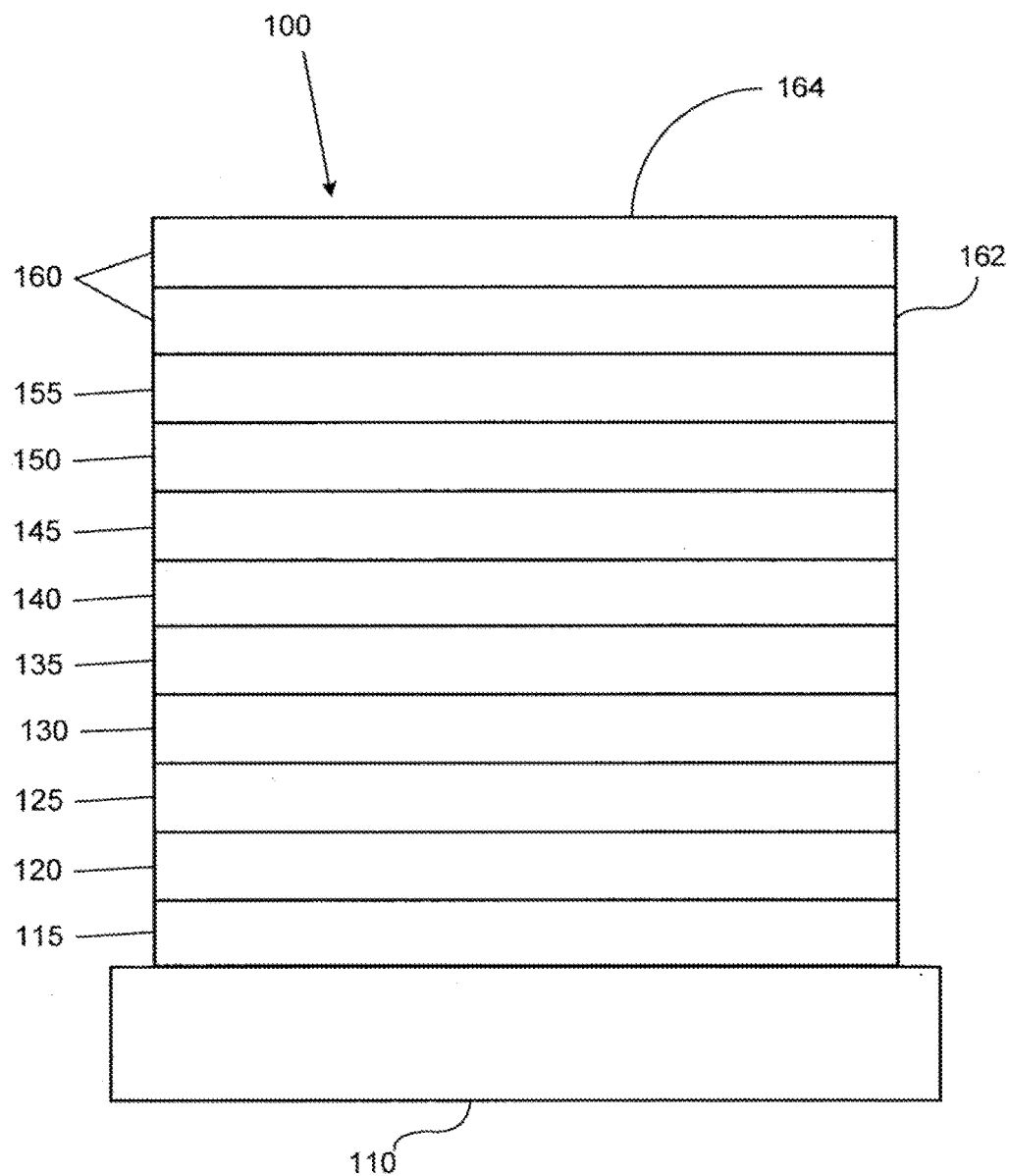
FIG. 1 shows an organic light emitting device that can incorporate the inventive compound disclosed herein.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
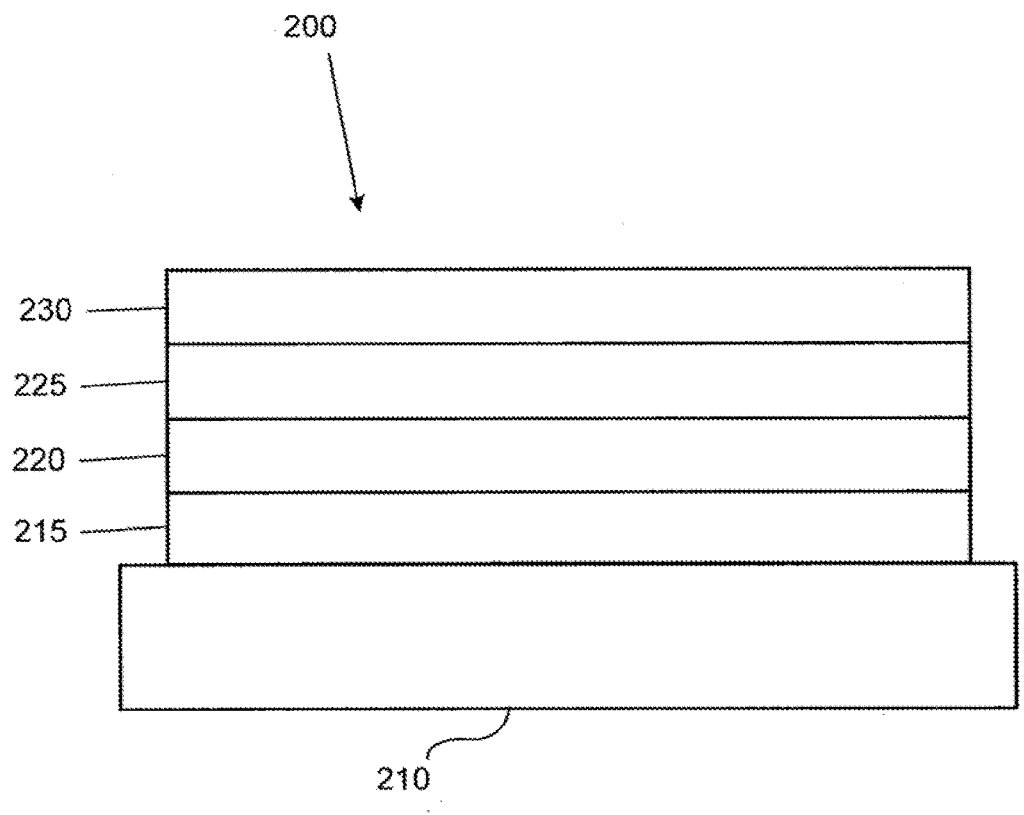
FIG. 2 shows an inverted organic light emitting device that can incorporate the inventive compound disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247, 190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

According to an embodiment of the present disclosure, a novel compound having a formula (I): A-L-B (I) is disclosed. In formula (I), A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof, which are optionally further substituted with one or more groups selected from hydrogen, deuterium, alkyl, cycloalkyl, arylalkyl, alkoxy, aryloxy, amino, silyl, aryl, heteroaryl, and combinations thereof. The substitution of one or more groups in A is optionally fused to the indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group. L is a single bond or comprises an aryl or heteroaryl group having from 5-30 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof. B is an all-benzenoid group having at least 24 carbon atoms, which are optionally further substituted with one or more groups selected from hydrogen, deuterium, alkyl, cycloalkyl, arylalkyl, alkoxy, aryloxy, amino, silyl, aryl, heteroaryl, and combinations thereof.

In one embodiment of the compound having the formula (I), L is selected from the group consisting of: a direct bond,

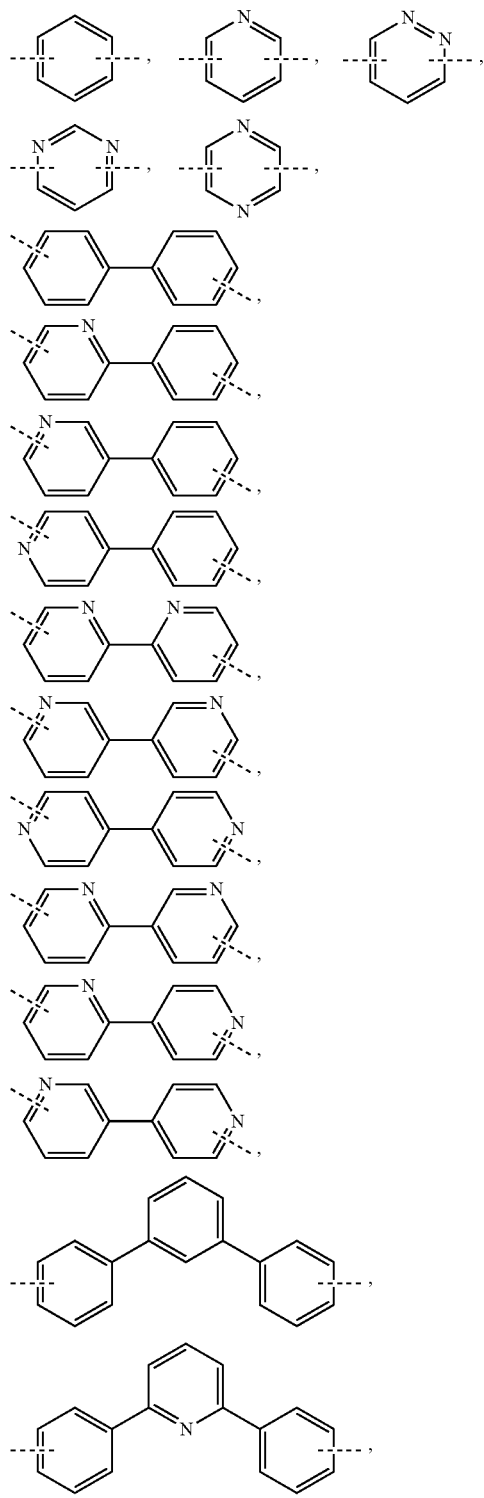

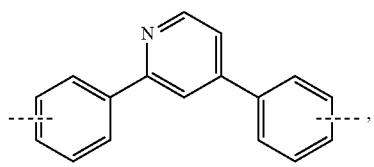

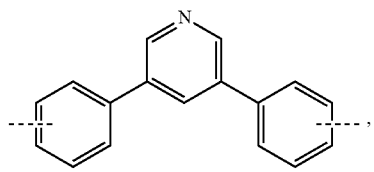

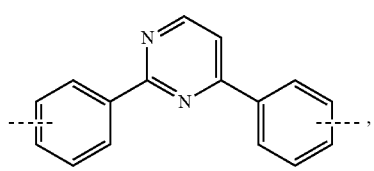

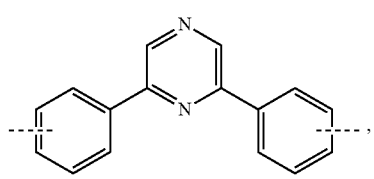

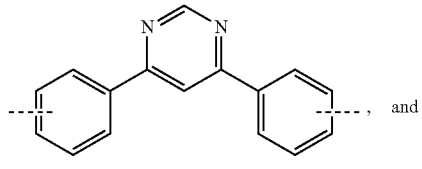

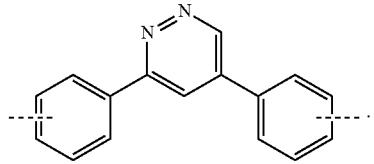

In another embodiment of the compound having the formula (I), A is

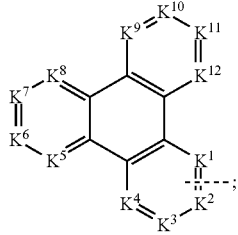

wherein $K^1$ to $K^{12}$ are independently selected from N and C—R'; and R' is selected from the group consisting of hydrogen, deuterium, alkyl, cycloalkyl, arylalkyl, alkoxy, aryloxy, amino, silyl, aryl, heteroaryl, and combinations thereof.

In another embodiment, A is selected from the group consisting of:

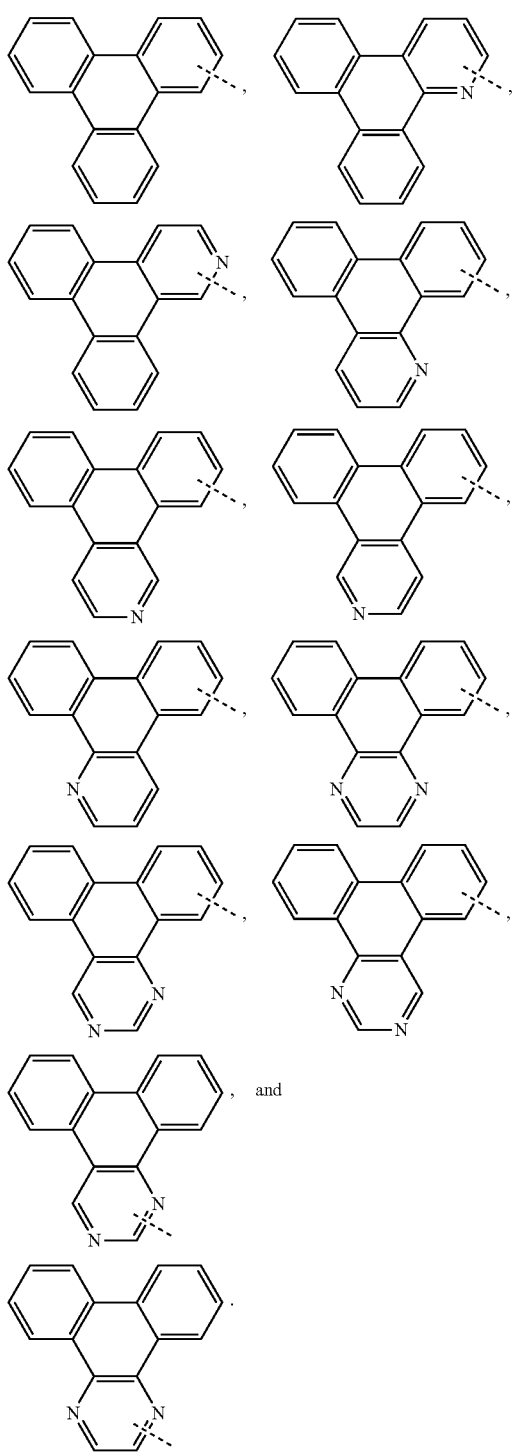
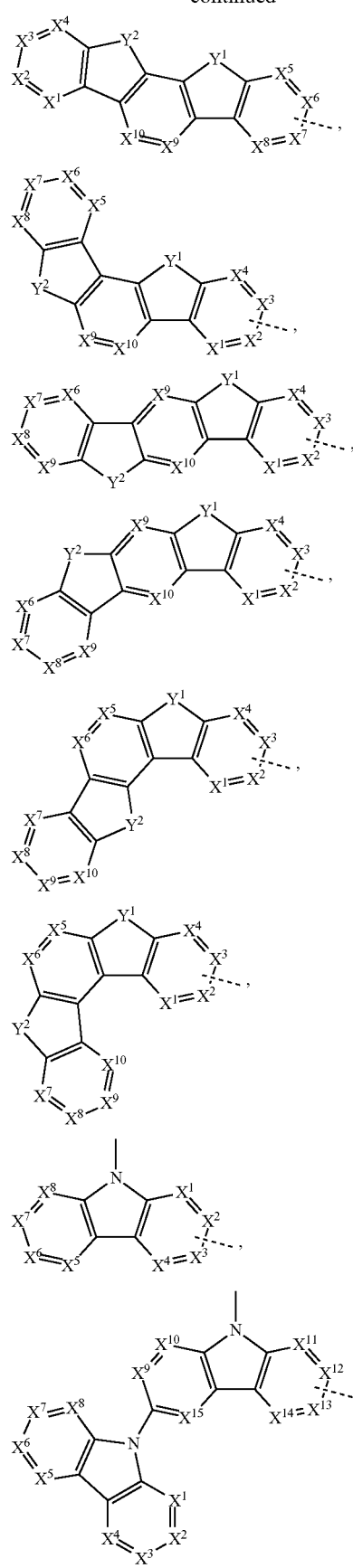
In another embodiment, A is selected from the group consisting of:
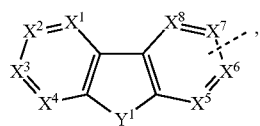

-continued

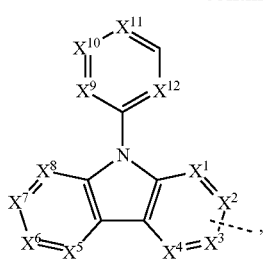

wherein $X^1$-$X^{15}$ are independently selected from the group consisting of N and C—R", wherein R" is selected from a group consisting of hydrogen, deuterium, alkyl, cycloalkyl, arylalkyl, alkoxy, aryloxy, amino, silyl, aryl, heteroaryl, and combinations thereof; and $Y^1$ and $Y^2$ are independently selected from the group consisting of O, S, and Se.

In another embodiment, A is selected from the group consisting of:

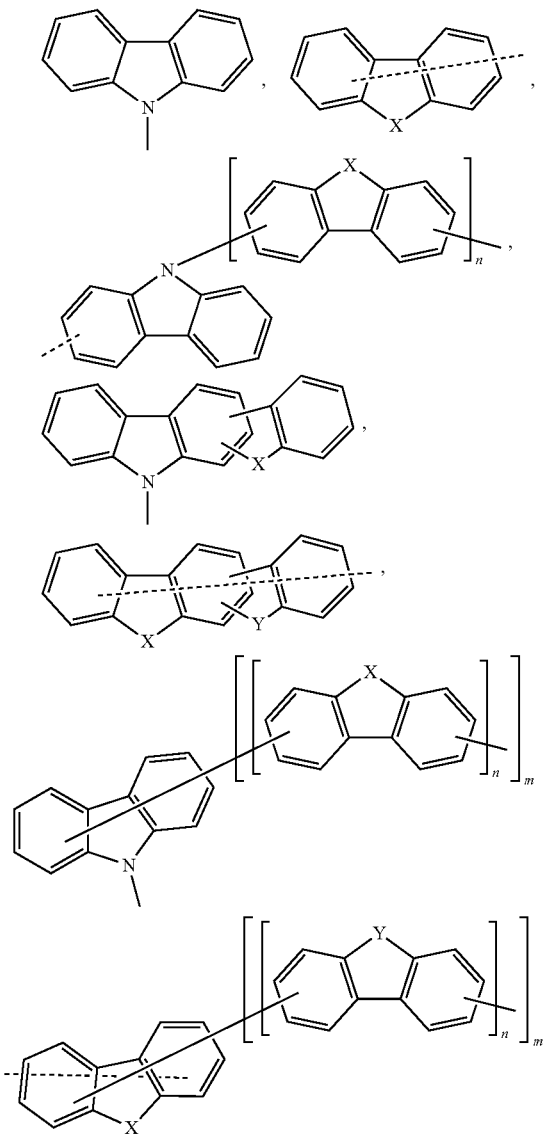

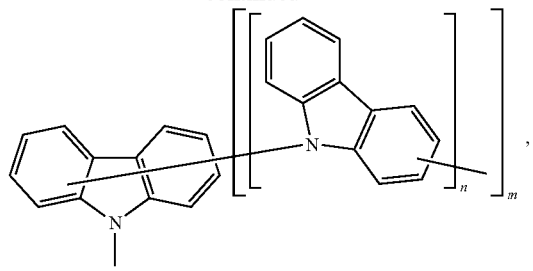

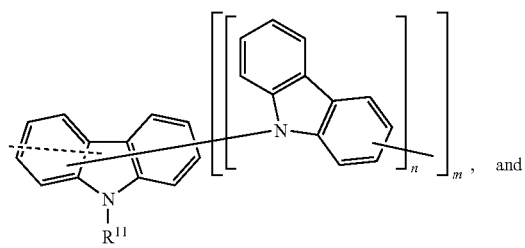

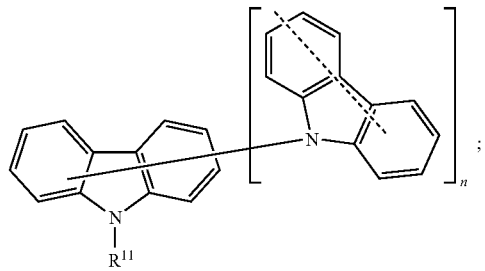

wherein n is an integer from 1 to 20;
m is an integer from 1 to 20;
X and Y are independently selected from the group consisting of O, S, and $NR^{14}$; and
$R^{11}$, $R^{12}$, $R^{13}$ and $R^{14}$ are selected from the group consisting of aryl and heteroaryl.

In another embodiment, A is selected from the group consisting of:

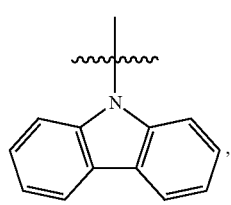

D$^{101}$

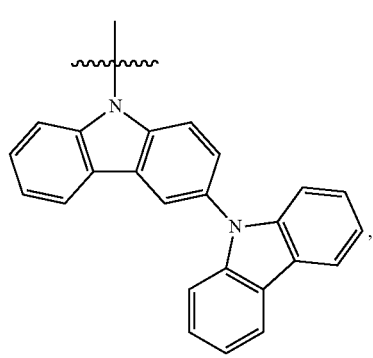

D$^{102}$

D103
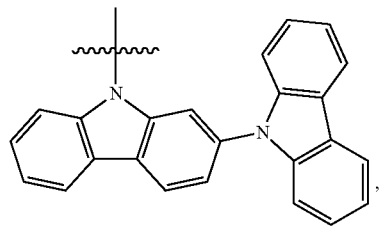
D104
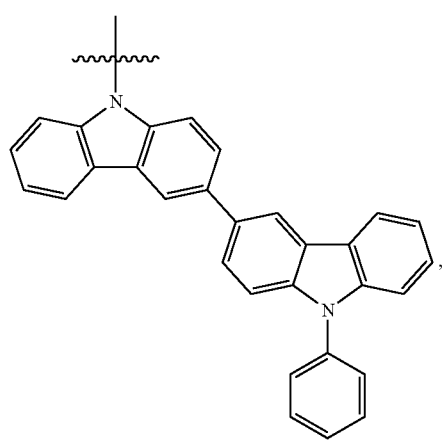
D105
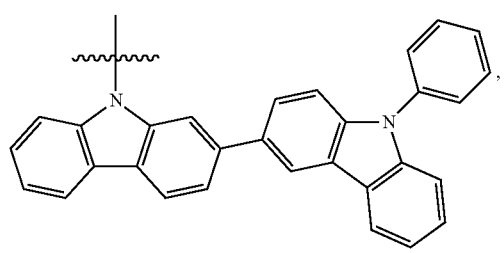
D106
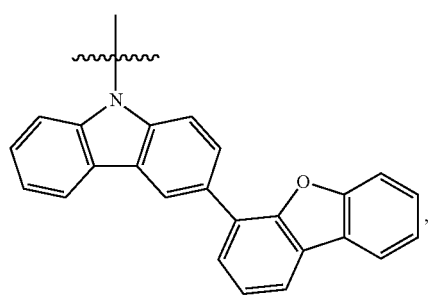
D107
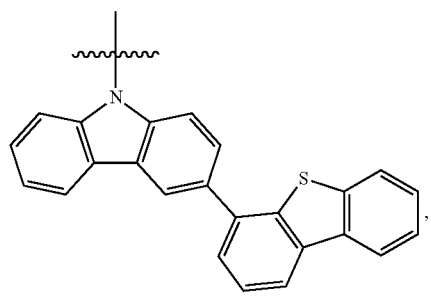
D108
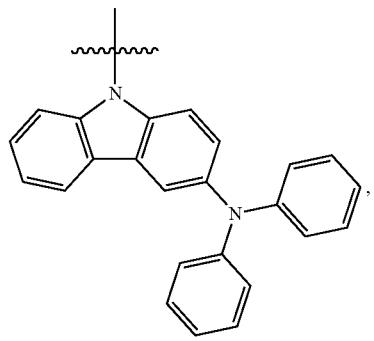
D109
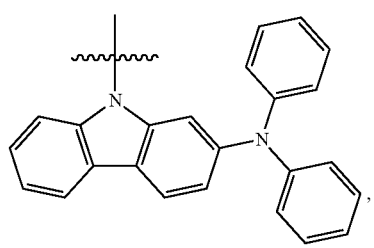
D110
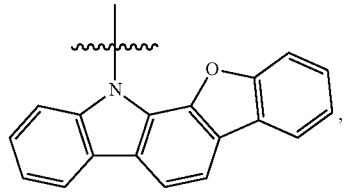
D111
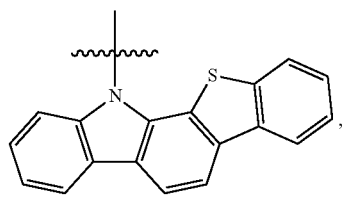
D112
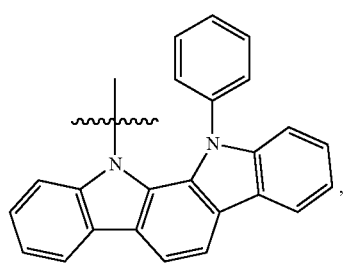
D113
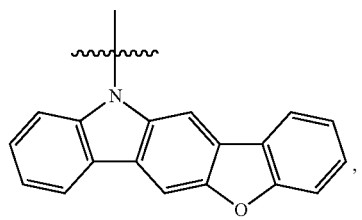

D114 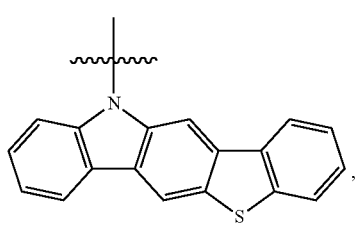,
D115 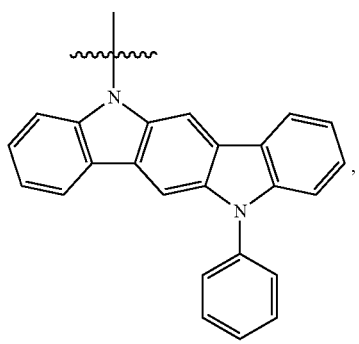,
D116 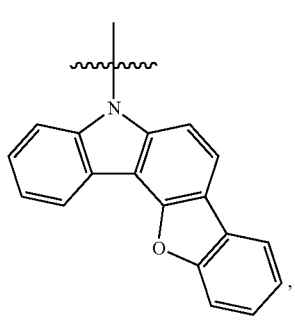,
D117 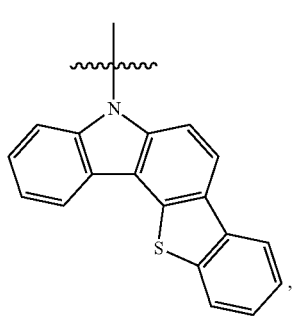,
D118 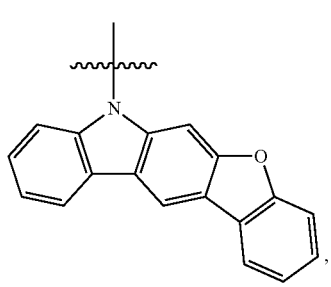,
D119 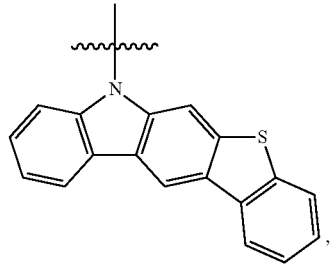,
D120 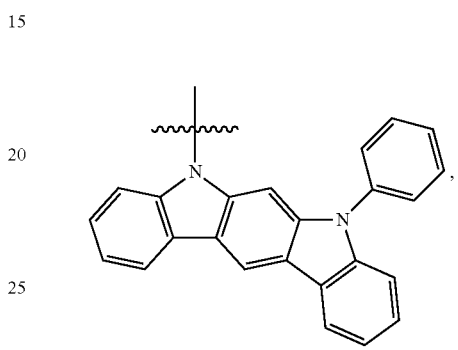,
D121 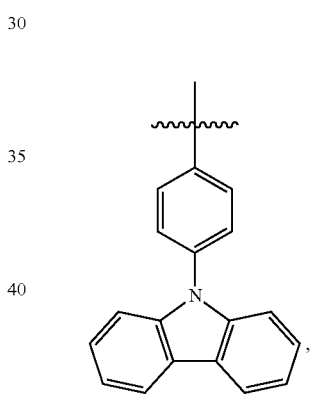,
D122 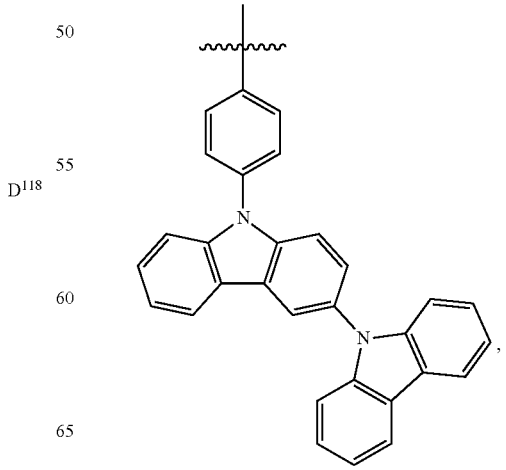,

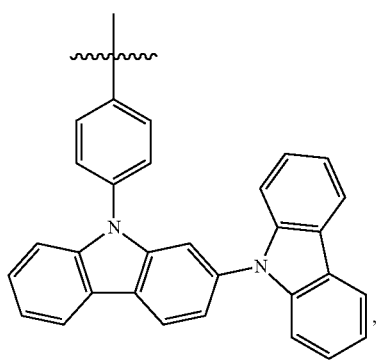
D[123]
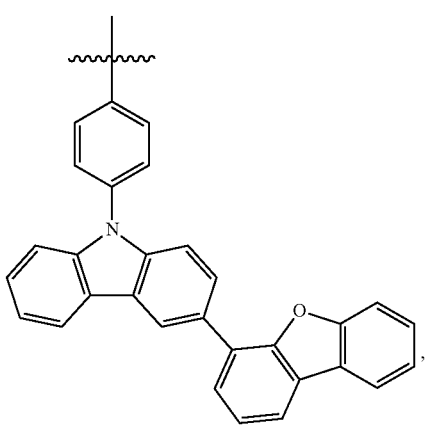
D[126]
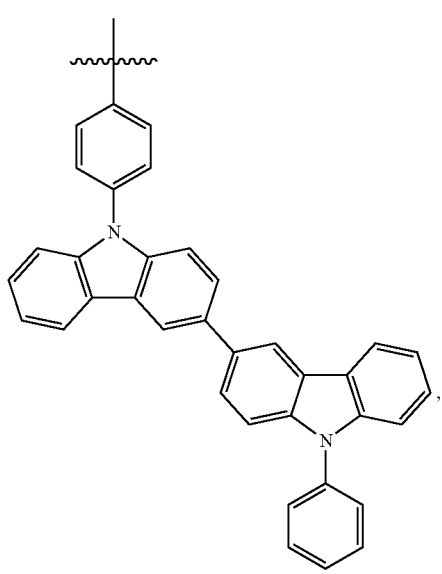
D[124]
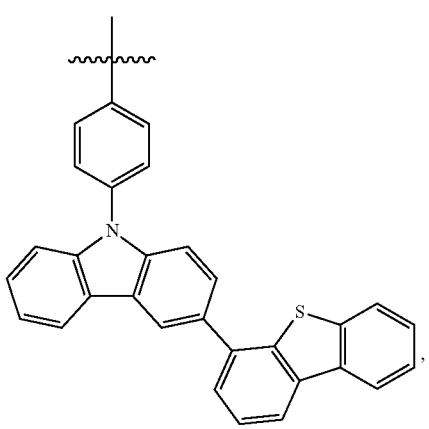
D[127]
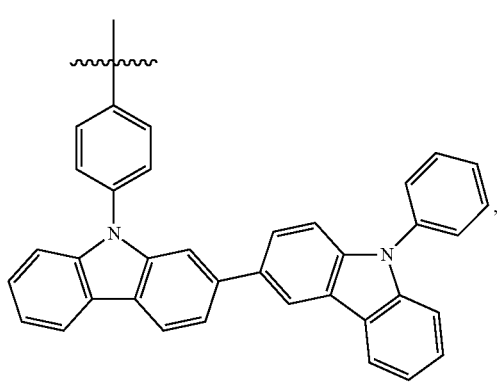
D[125]
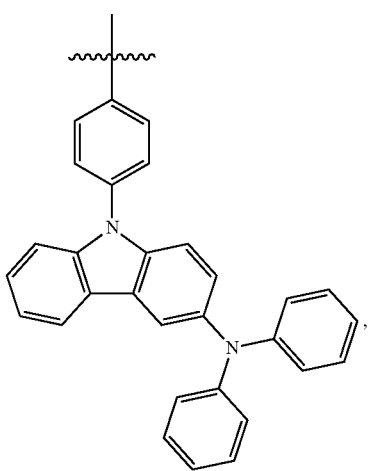
D[128]

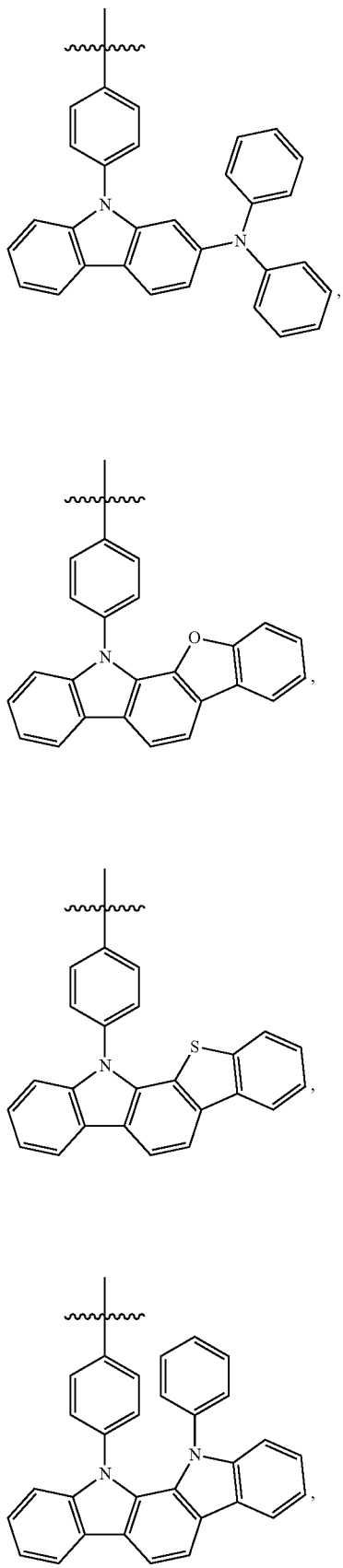
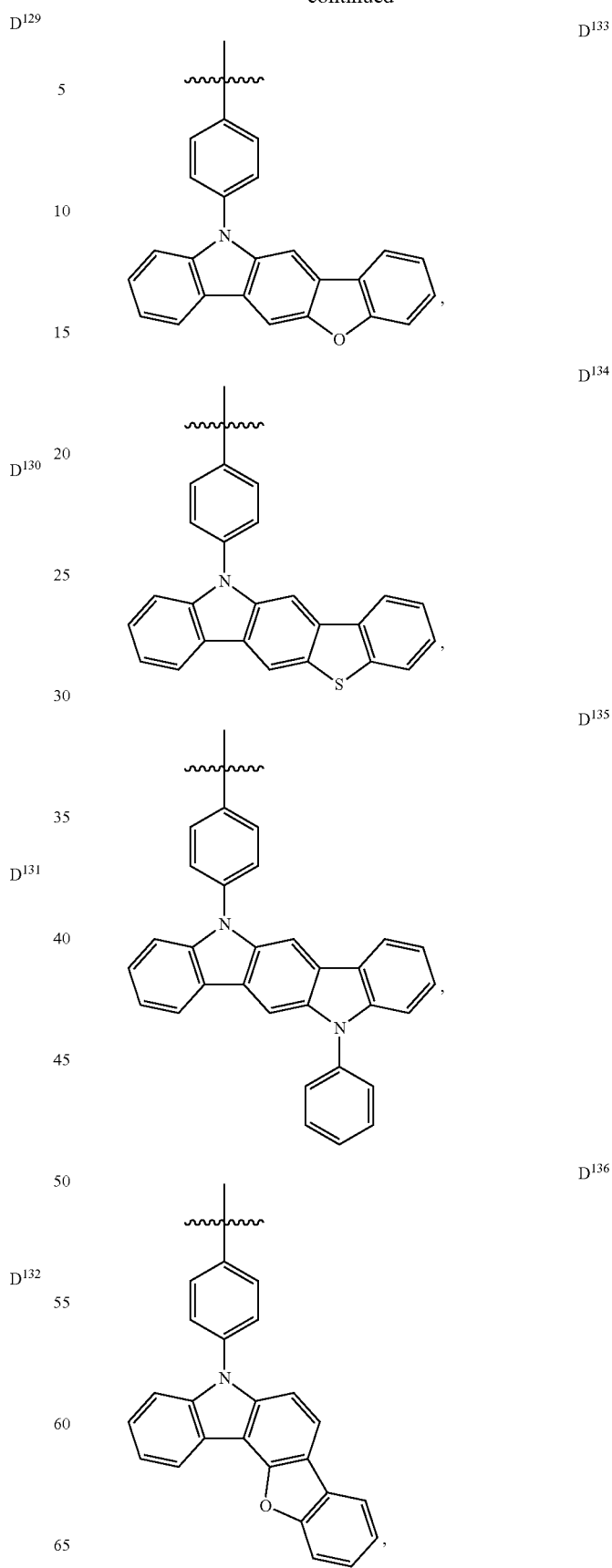

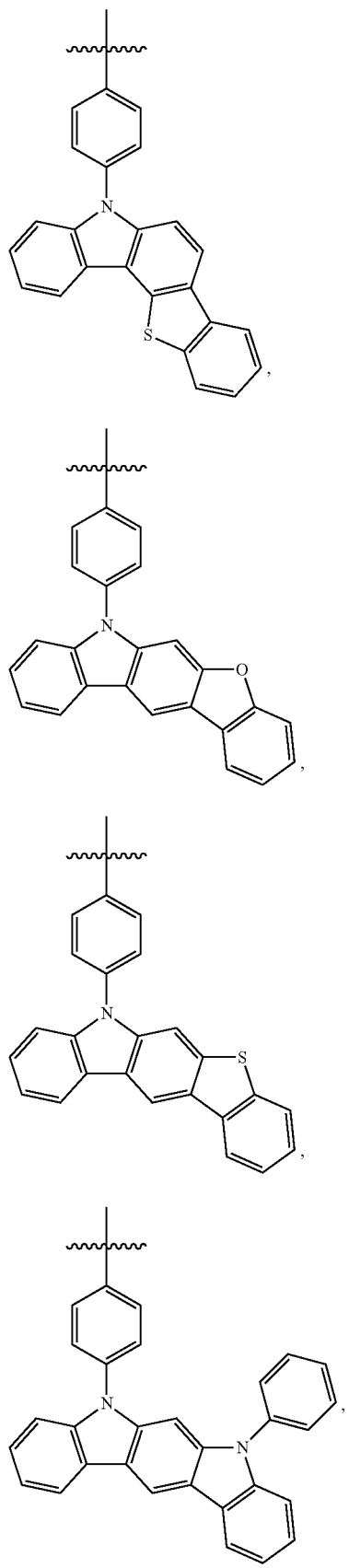
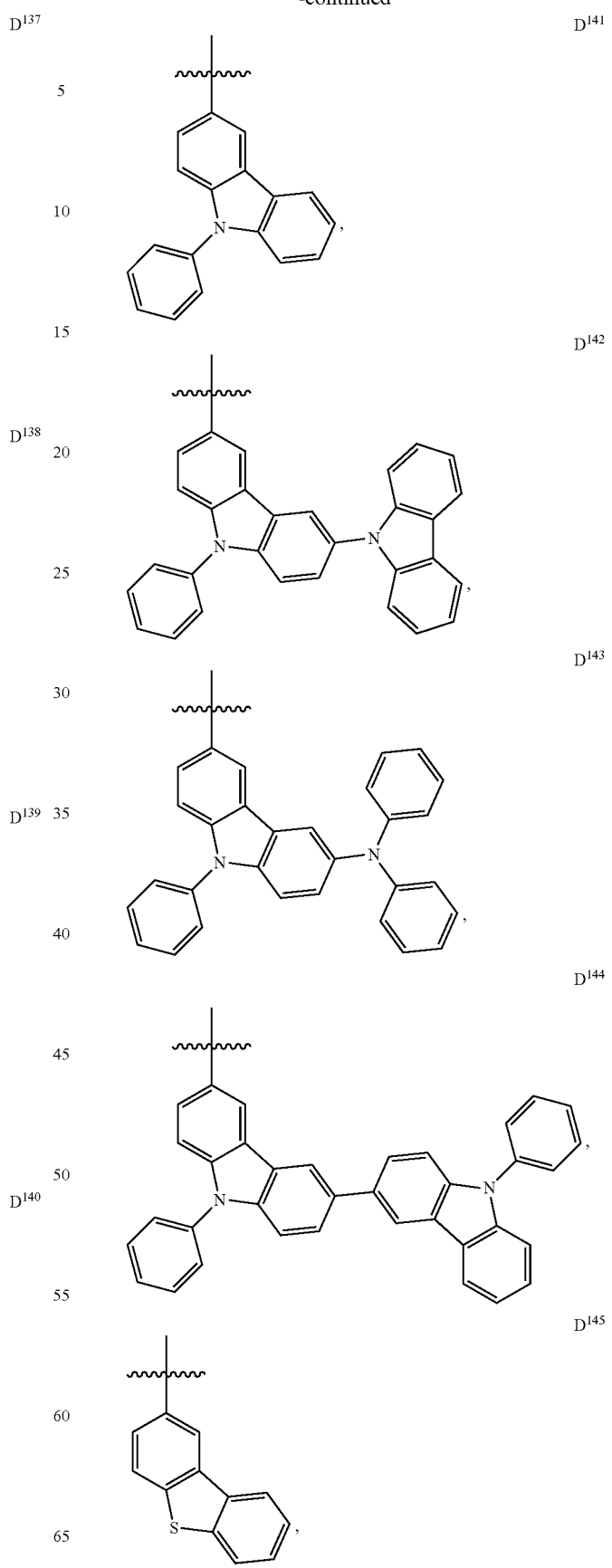

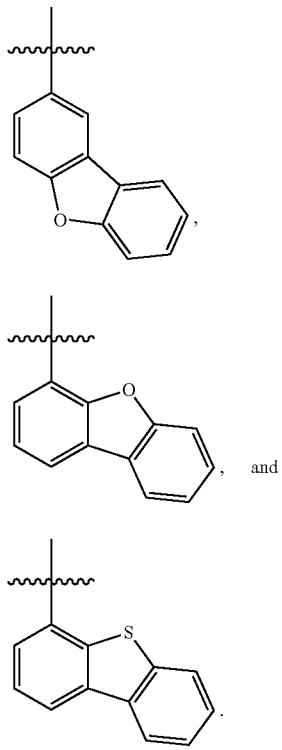
In another embodiment, A is selected from the group consisting of:
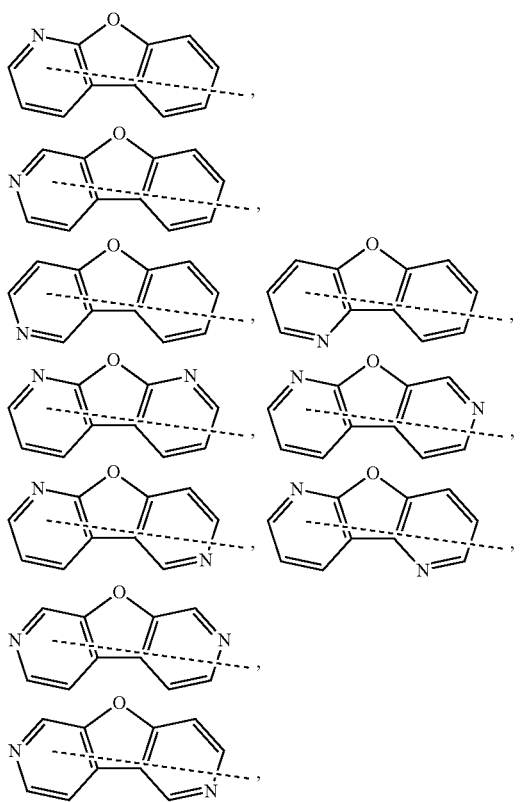
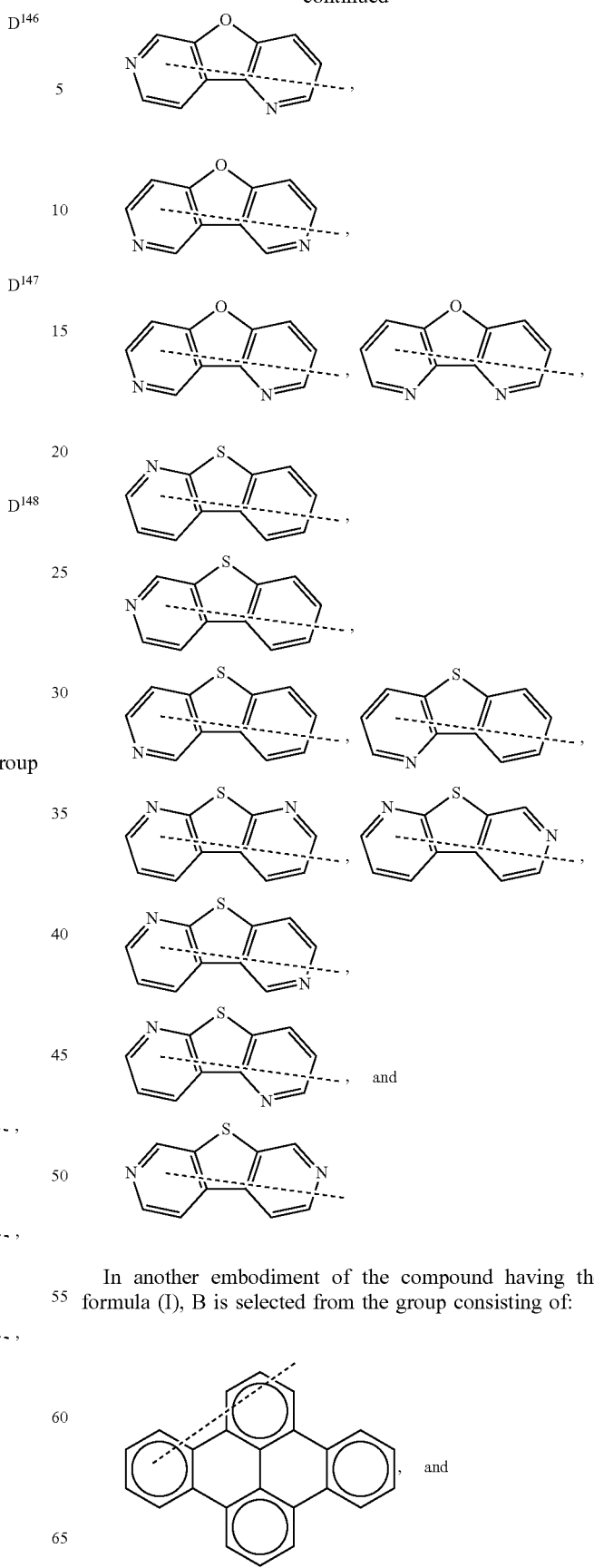
In another embodiment of the compound having the formula (I), B is selected from the group consisting of:
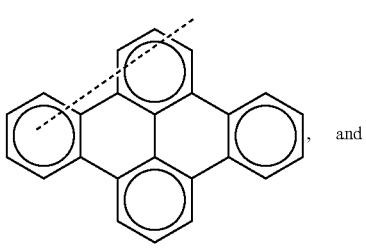, and

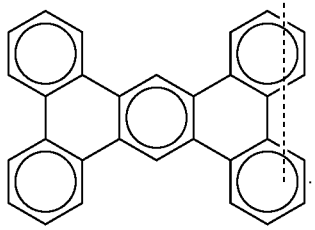

In another aspect, a formulation comprising a compound having the formula (I), A-L-B (I), described herein is disclosed.

Dibenzo[fg,op]tetracene and larger all-benzenoid compounds are polyaromatic compounds which can be drawn using only fully aromatic benzene rings (sextets). The simplest compound in the series is benzene. The next homolog is triphenylene which has been used as building blocks for host and other functional materials in OLEDs.

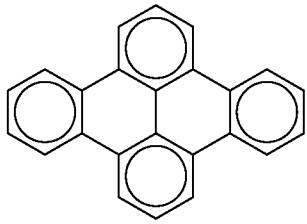

dibenzo[fg,op]tetracene.

| | Maximum no. of sextets |
|---|---|
|   | 1 sextet |
| 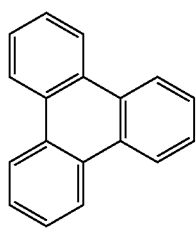 [SMILES: c1ccc2c(c1)c1ccccc1c1ccccc21] 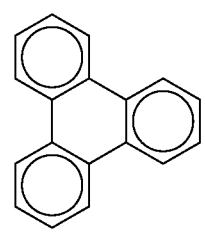 | 3 sextets |

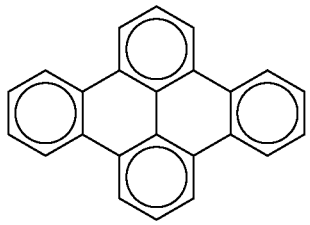

dibenzo[fg,op]tetracene.

| | Maximum no. of sextets |
|---|---|
| 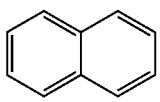 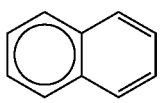 | 1 sextet and 1 diene |
| 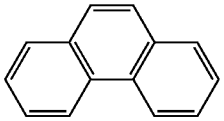 | 2 sextets and 1 ene |

Dibenzo[fg,op]tetracene, the $3^{rd}$ homolog in the series, and larger all-benzenoid compounds, despite the high π-electron delocalization, have higher triplet energy compared to non all-benzenoid compounds (compounds which must be drawn with ene or diene) with the same number of carbons. Dibenzo[fg,op]tetracene and larger all-benzenoid compounds are therefore useful as host building blocks for phosphorescent emitters to provide low-voltage, high-efficiency and high-stability devices.

To demonstrate the relatively high triplet energy of these all-benzenoid compounds, Compound 2-X and 2-Y were synthesized. The data is summarized in Table 1 below. For comparison, the triplet of anthracene is well beyond 650 nm and tetracene is 700 nm. In addition, the LUMO can be quite deep due to the high π-electron delocalization. For example, the reduction potential is 2.55 V for Compound 2-X. When such compounds are used as the hosts in OLEDs, the operating voltage may be low.

TABLE 1
| Structure | Compound | CV data [V] | $\lambda_{peak}$ at RT [nm] | $\lambda_{peak}$ at 77K [nm] |
|---|---|---|---|---|
| 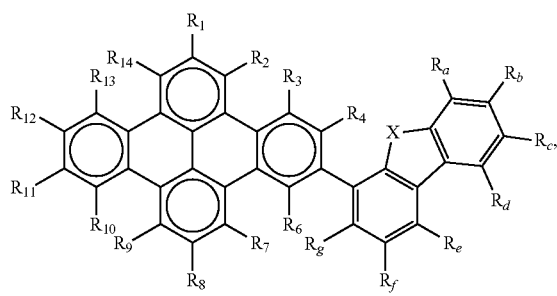 | 2-X | Red: −2.55 (R)<br>Ox: 0.47 (R) | 438 | 512 |
| 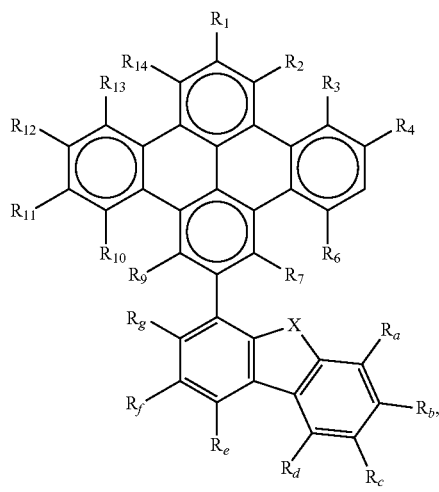 | 2-Y | | 388 | 501 |
According to an aspect, preferred structures for the novel compound having dibenzo[fg,op]tetracene or larger all-benzenoid moiety are:
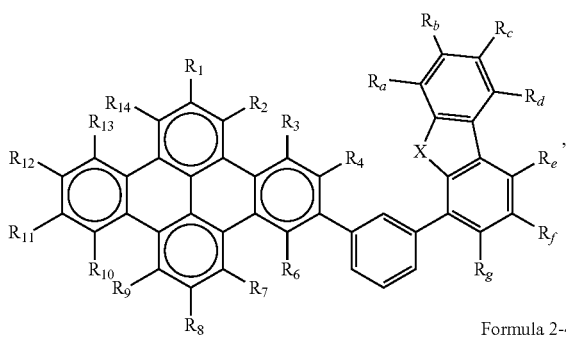
Formula 2-1, Formula 2-2
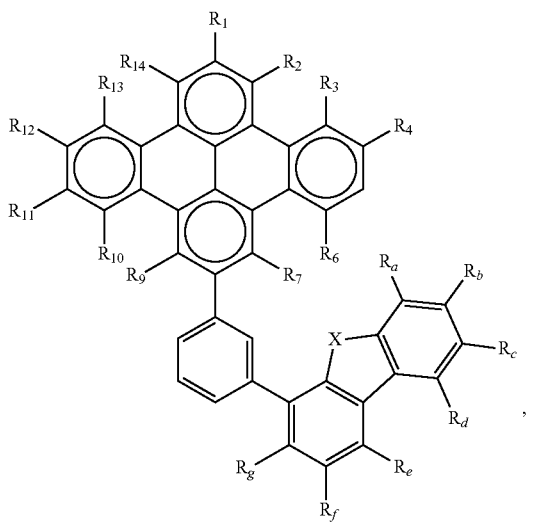
Formula 2-3, Formula 2-4

Formula 2-5
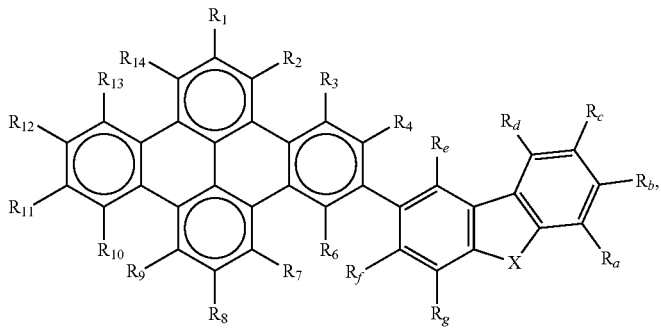
Formula 2-6
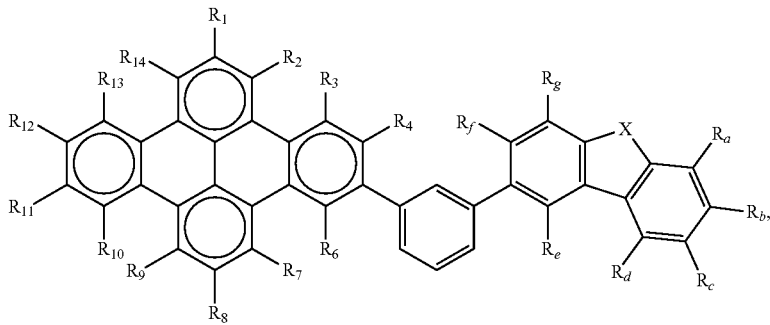
Formula 2-7
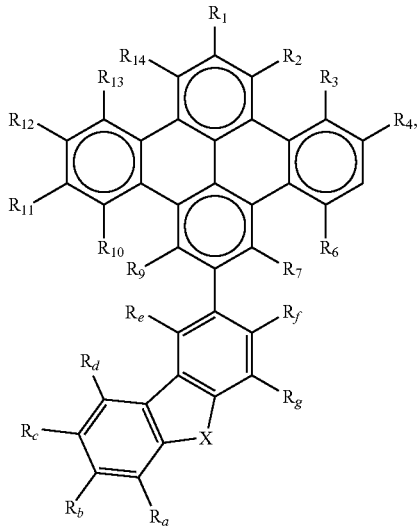
Formula 2-8
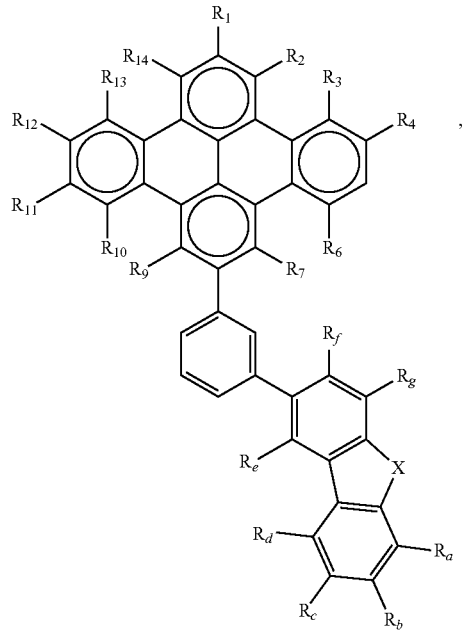
Formula 2-9
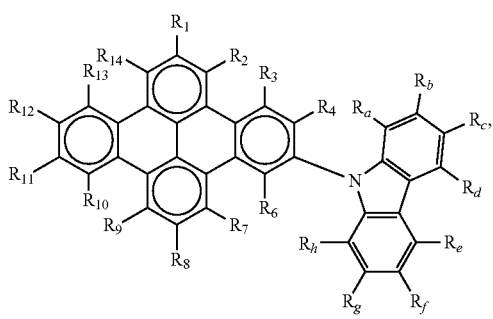
Formula 2-10
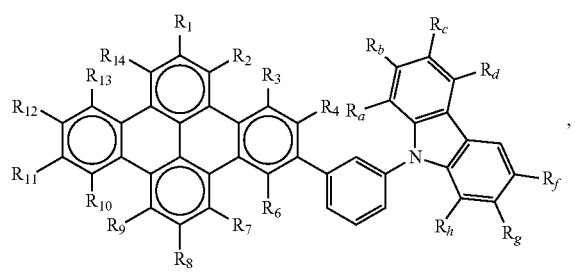

-continued
Formula 2-11
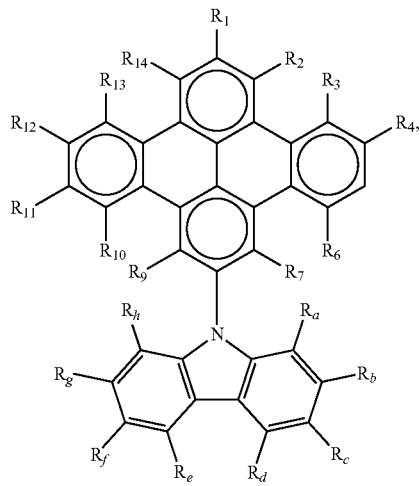
Formula 2-12
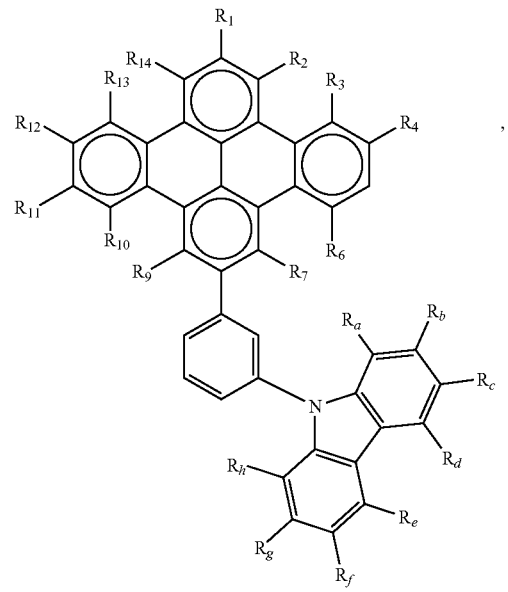
Formula 3-1
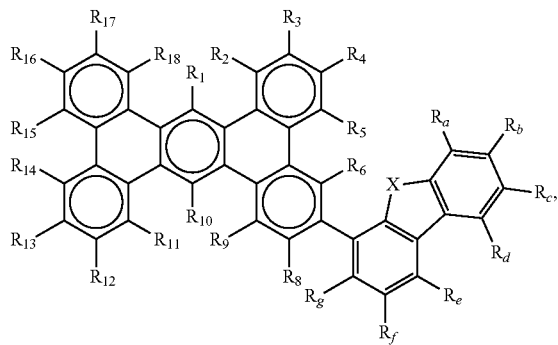
Formula 3-2
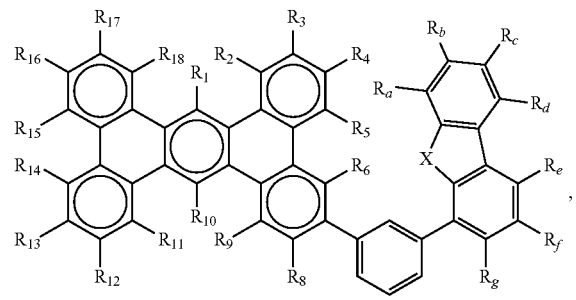
Formula 3-3
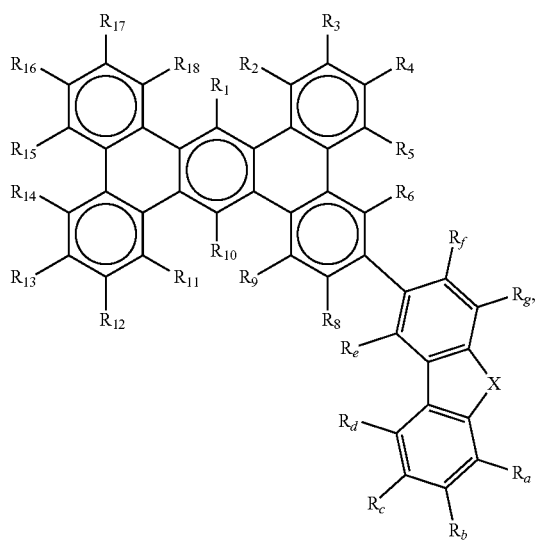

-continued

Formula 3-4

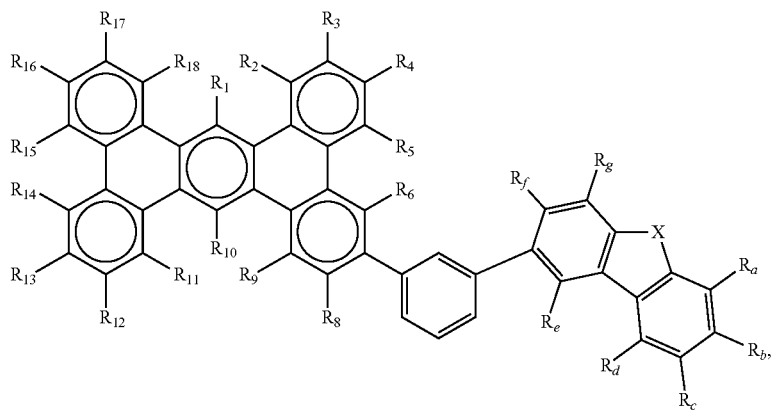

Formula 3-5

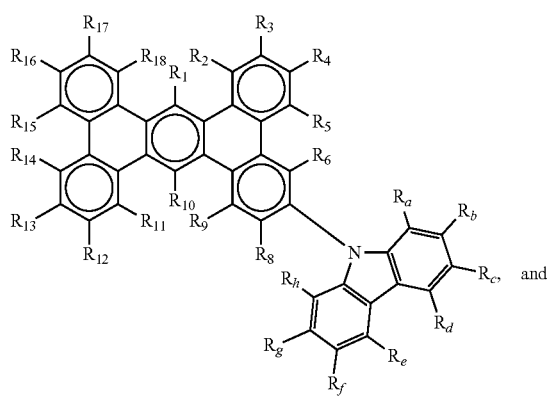

Formula 3-6

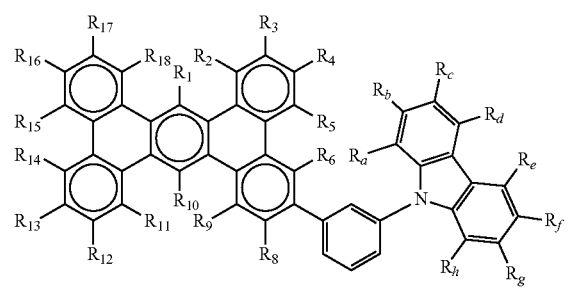

wherein each different R's are selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

Examples of some specific inventive compounds having the preferred structures presented above are:

Compound 1

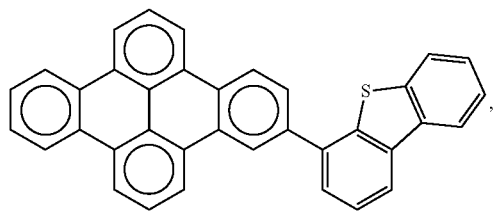

Compound 2

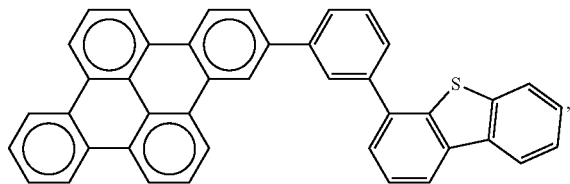

Compound 3

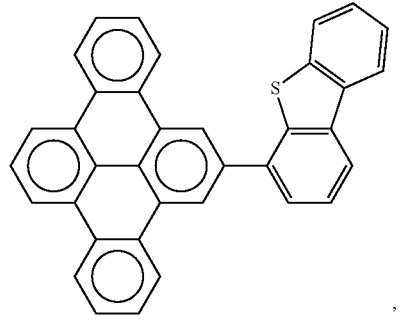

Compound 4

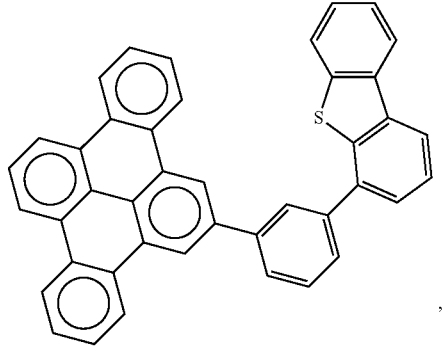

-continued
Compound 5
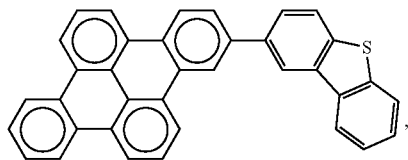
Compound 6
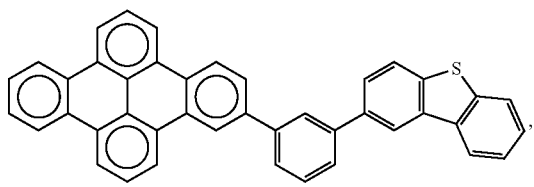
Compound 7
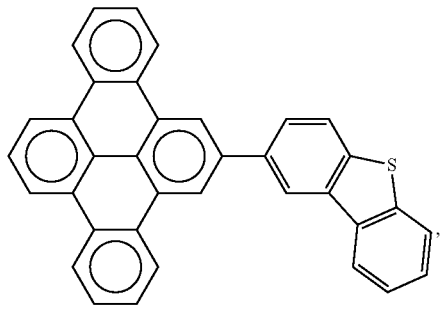
Compound 8
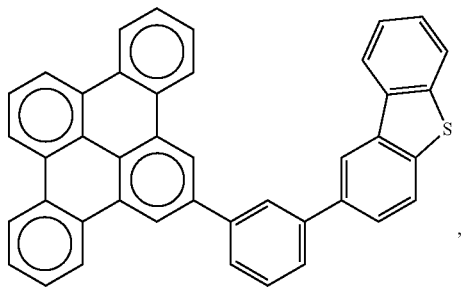
Compound 9
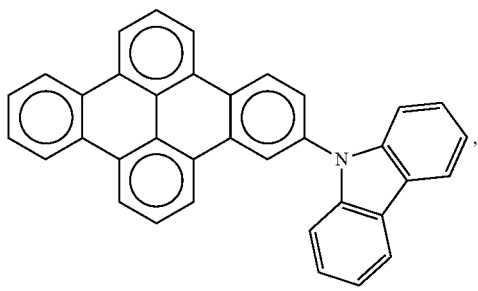
Compound 10
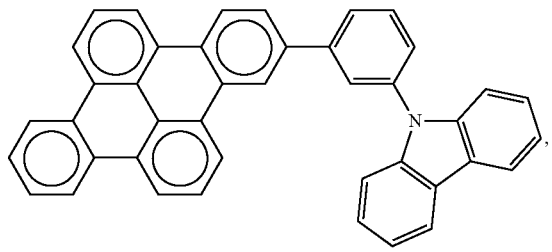
Compound 11
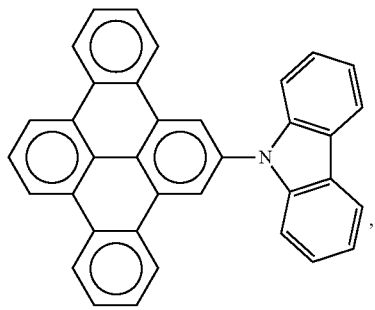
Compound 12
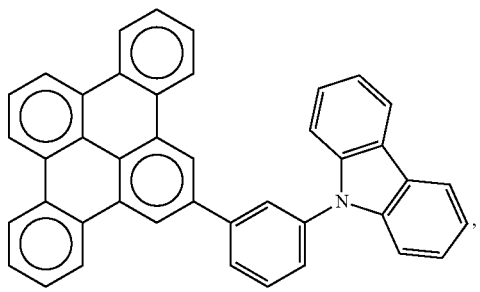
Compound 13
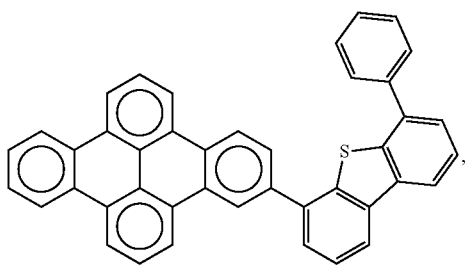
Compound 14
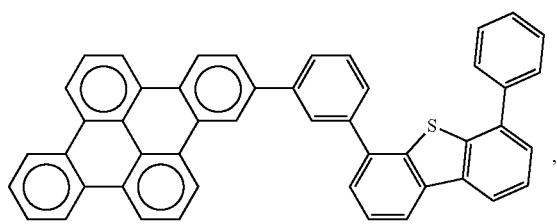

-continued
Compound 15
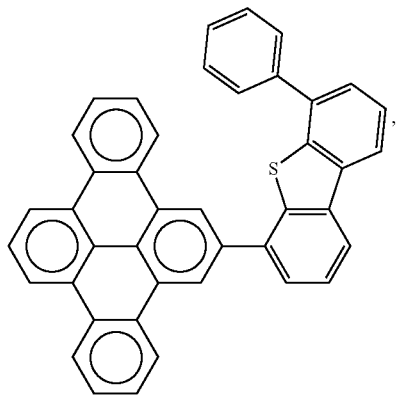
Compound 16
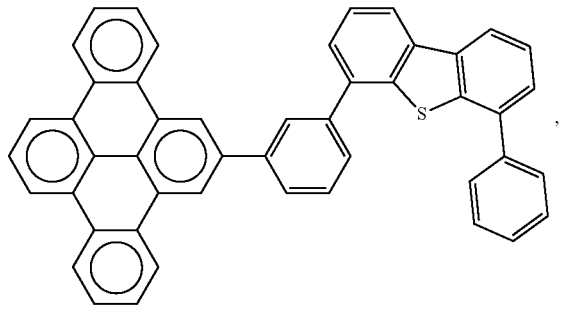
Compound 17
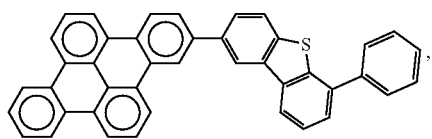
Compound 18
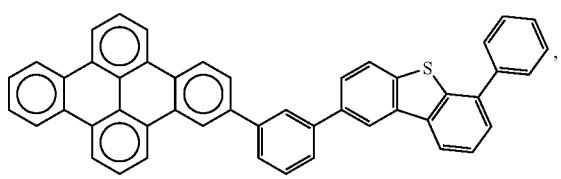
Compound 19
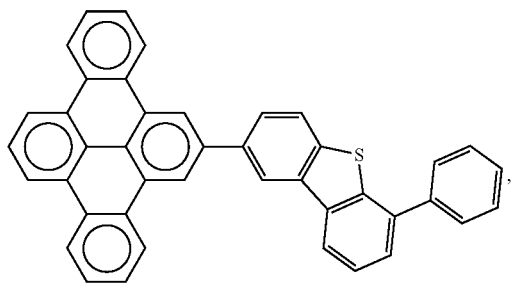
Compound 20
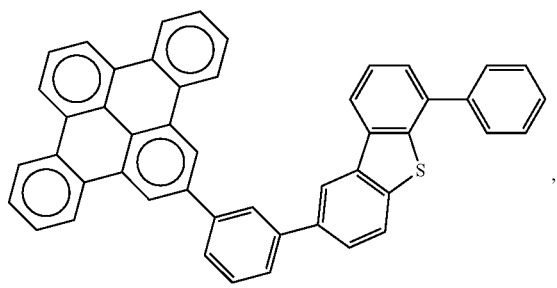
Compound 21
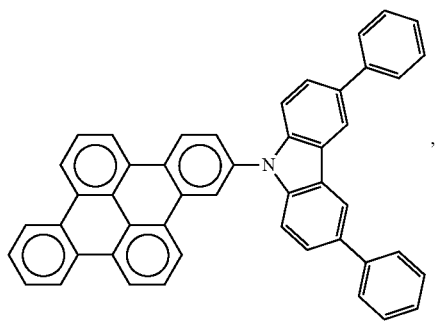
Compound 22
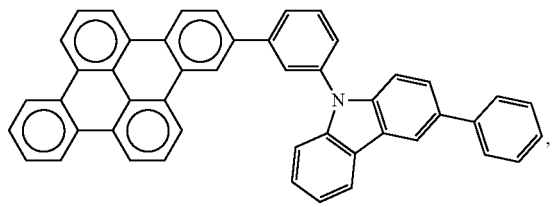

-continued
Compound 23
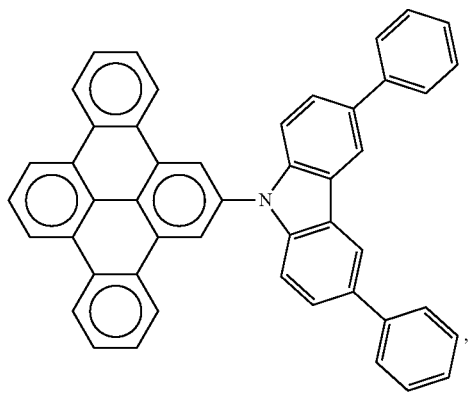
Compound 24
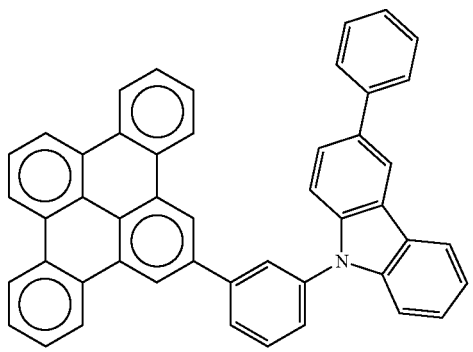
Compound 25
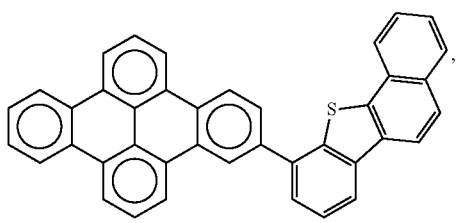
Compound 26
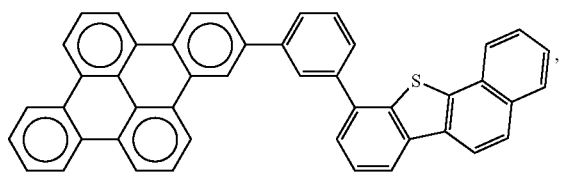
Compound 27
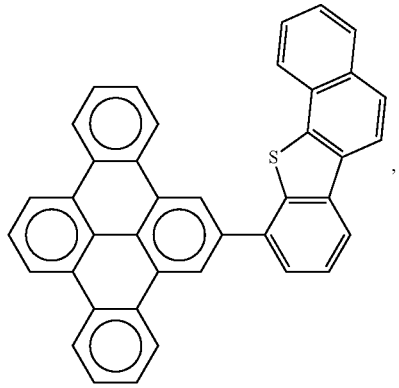
Compound 28
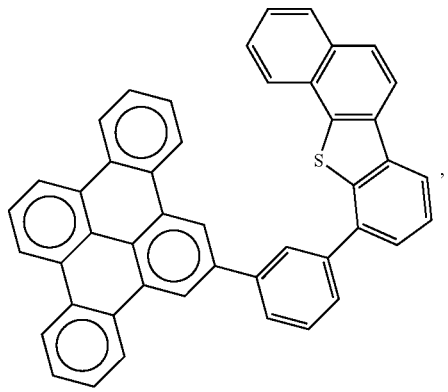
Compound 29
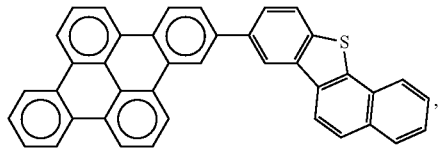
Compound 30
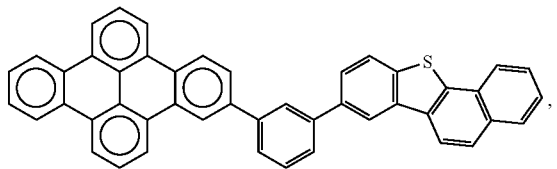
Compound 31
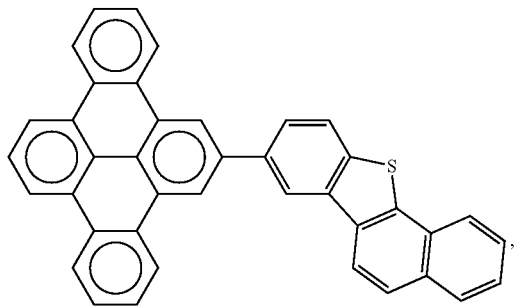
Compound 32
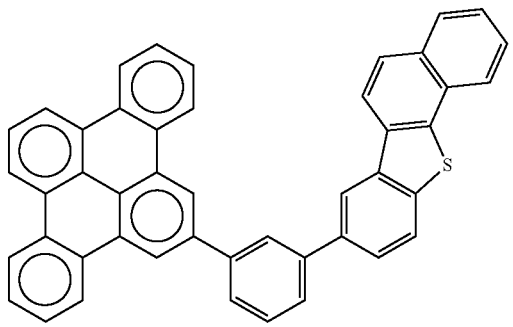

-continued

Compound 33

Compound 34

Compound 35

Compound 36

Compound 37

Compound 38

Compound 39

Compound 40

Compound 41

Compound 42

-continued
Compound 43
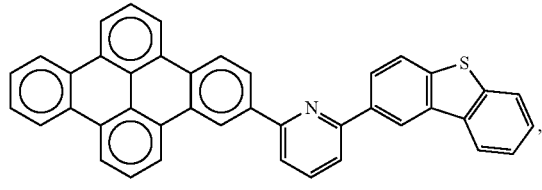
Compound 44
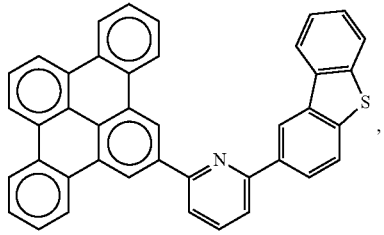
Compound 45
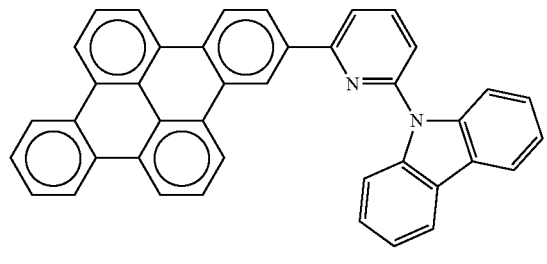
Compound 46
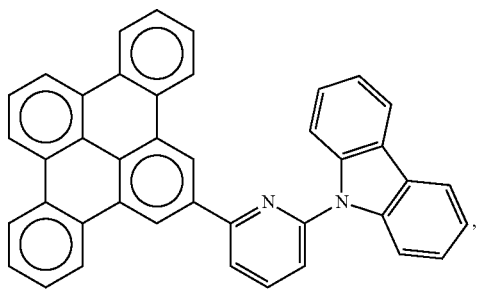
Compound 47
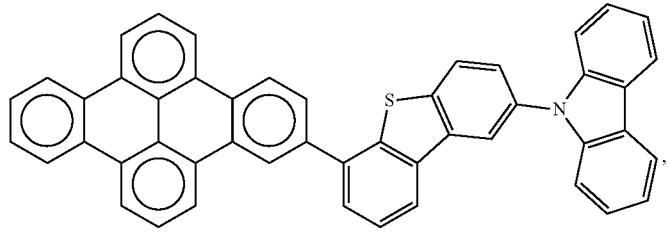
Compound 48
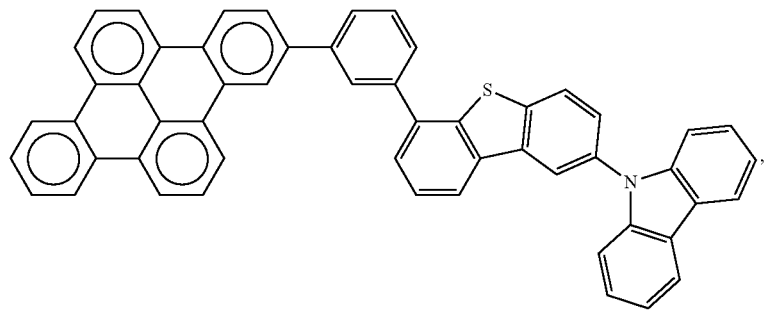
Compound 49
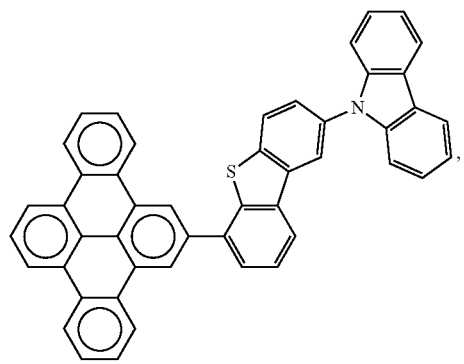
Compound 50
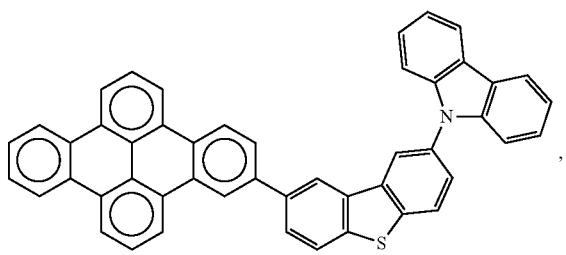

-continued
Compound 51
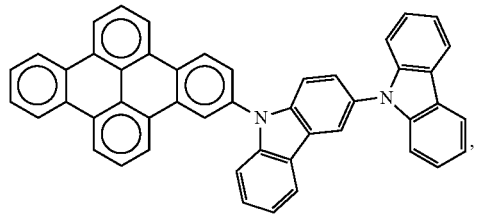
Compound 52
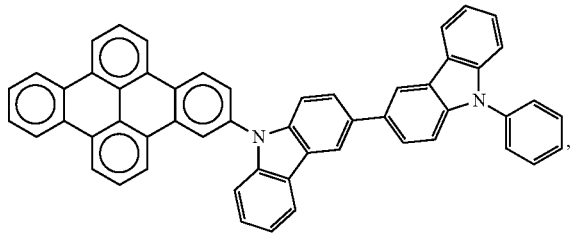
Compound 53
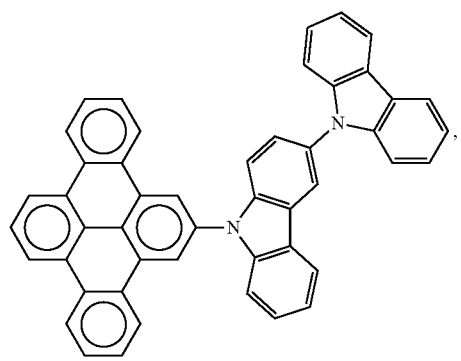
Compound 54
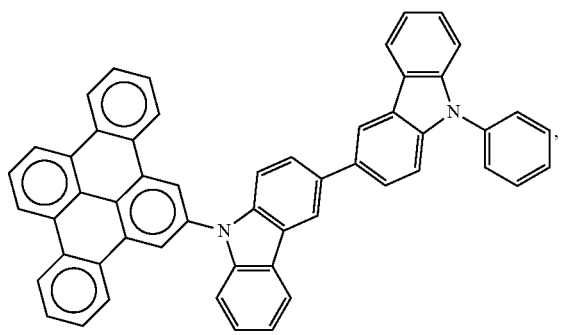
Compound 55
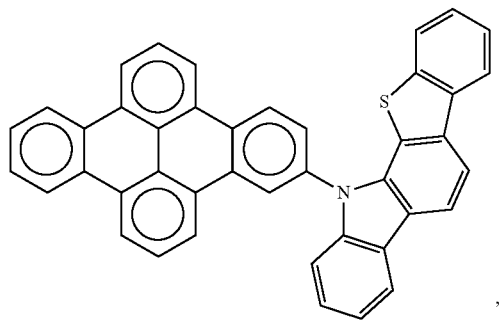
Compound 56
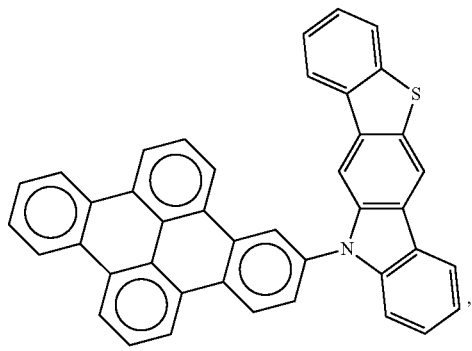
Compound 57
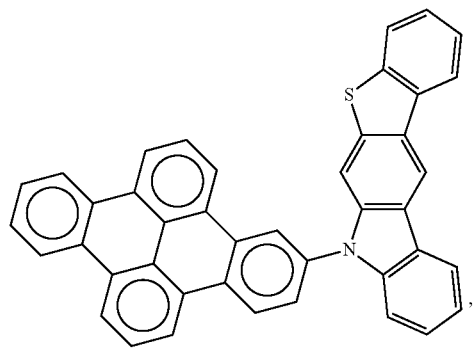
Compound 58
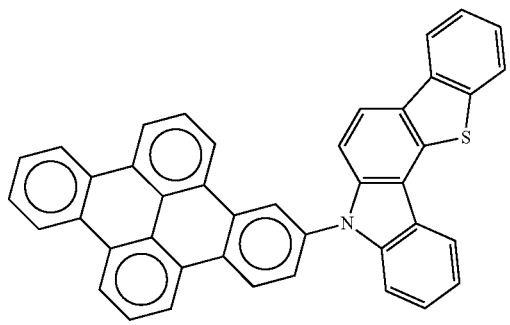

-continued
Compound 59 Compound 60
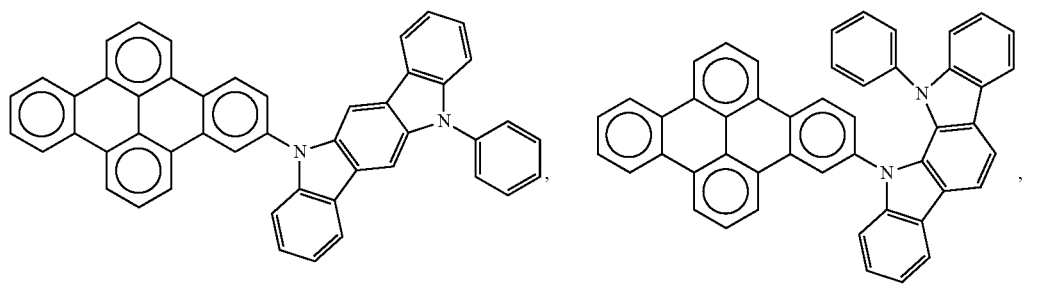
Compound 61 Compound 62
Compound 63 Compound 64
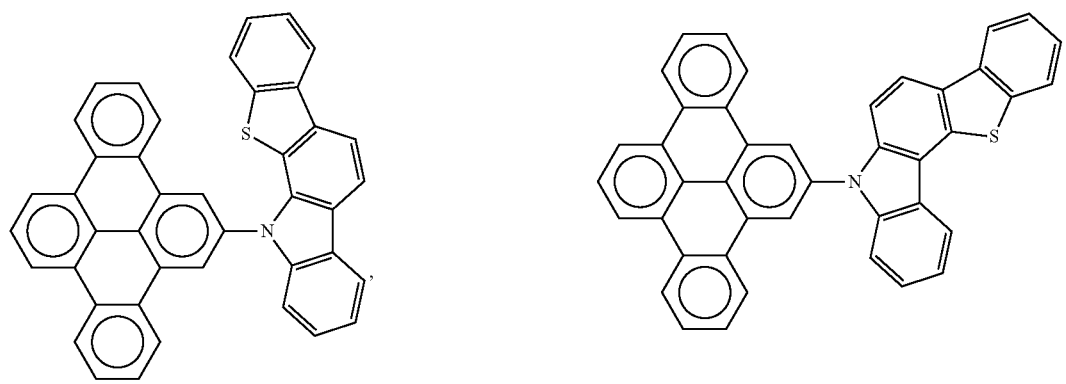
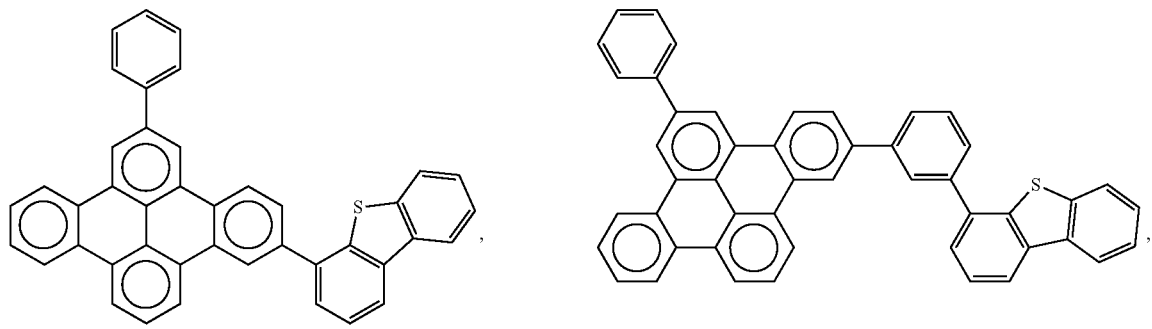
Compound 65 Compound 66
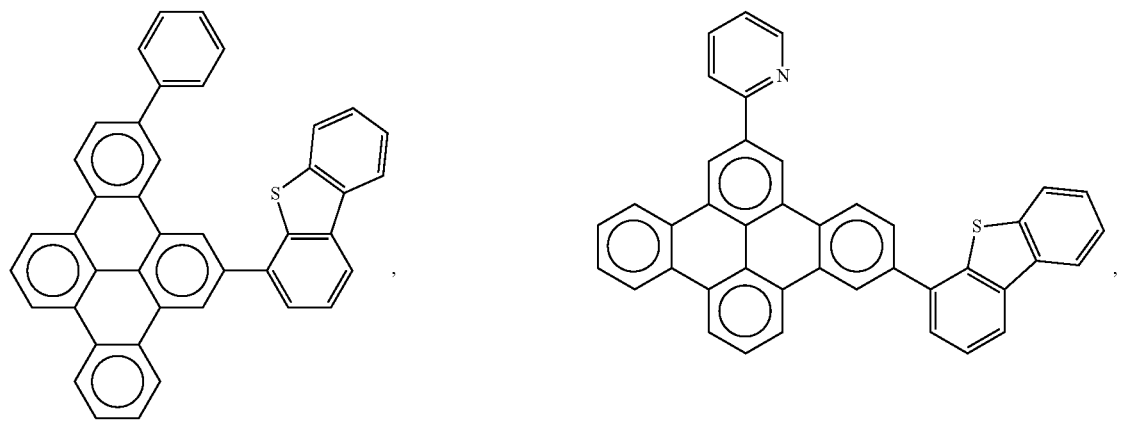

-continued
Compound 67
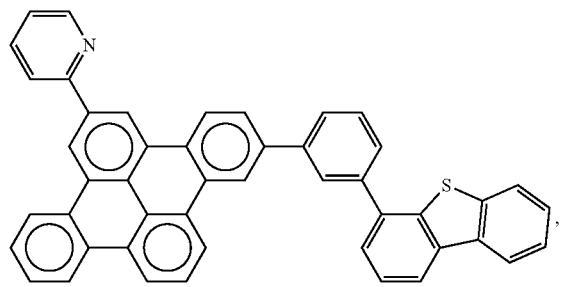
Compound 68
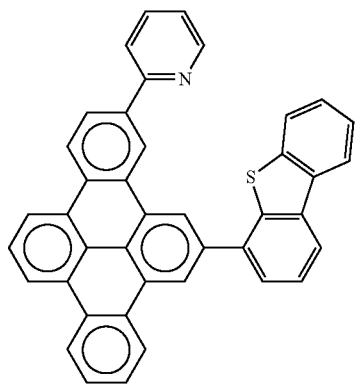
Compound 69
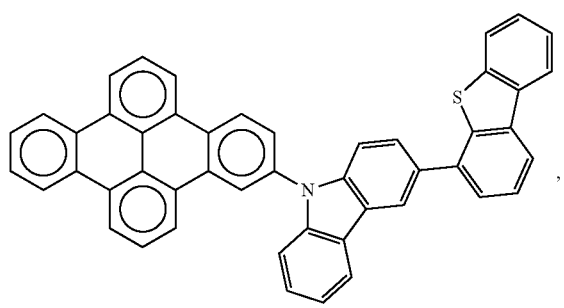
Compound 70
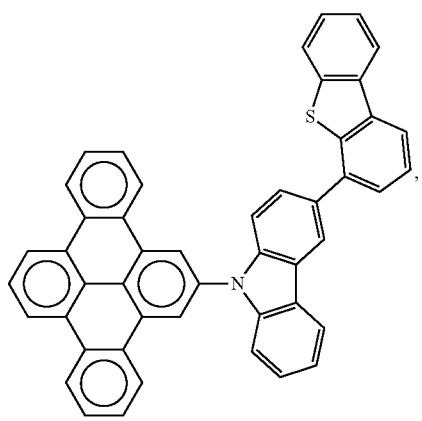
Compound 71
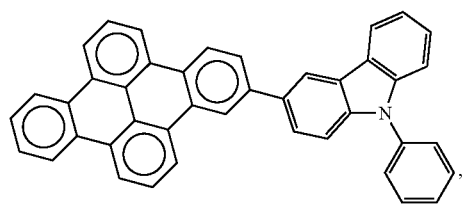
Compound 72
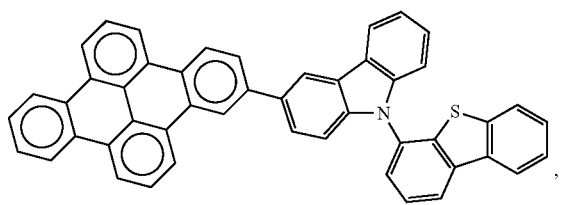
Compound 73
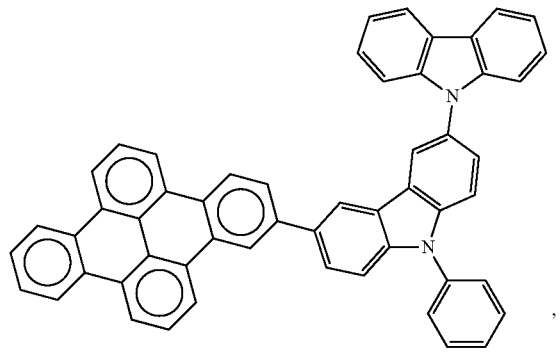
Compound 74
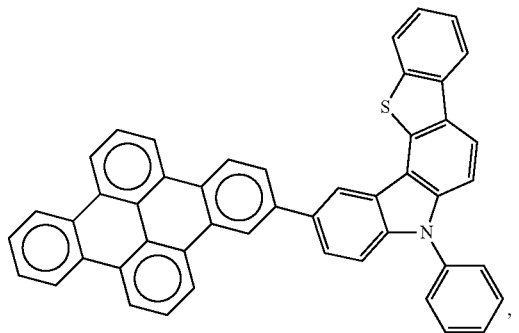

-continued
Compound 75
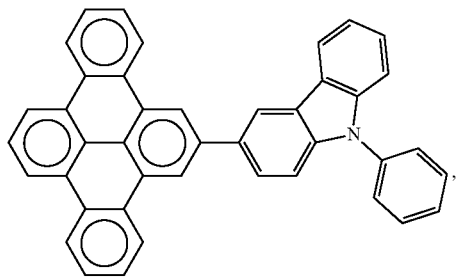
Compound 76
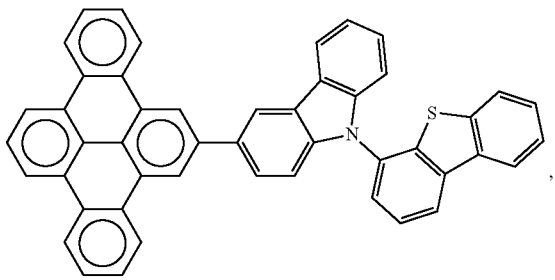
Compound 77
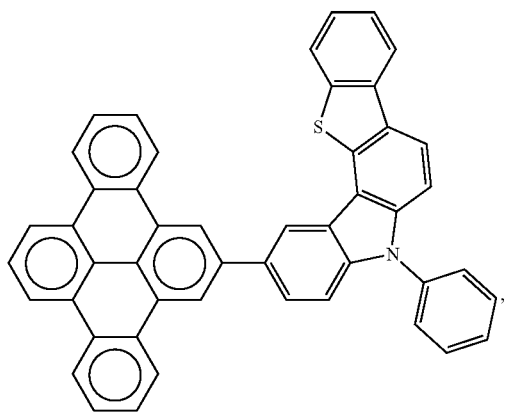
Compound 78
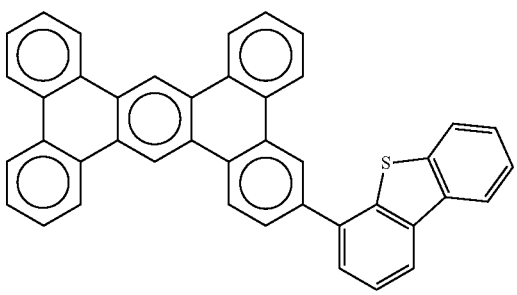
Compound 79
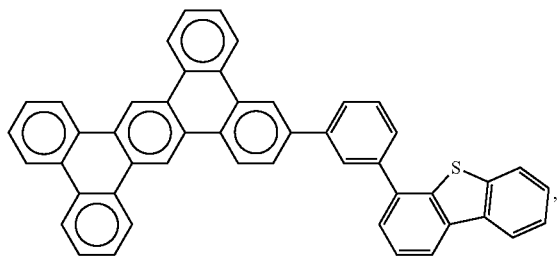
Compound 80
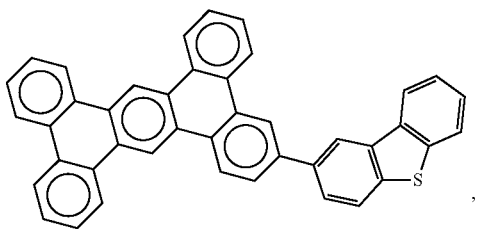
Compound 81
Compound 82
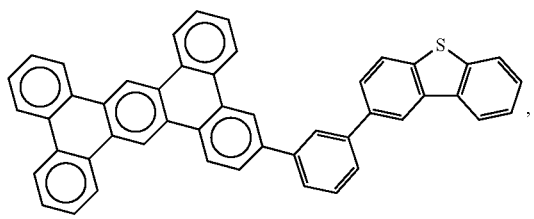
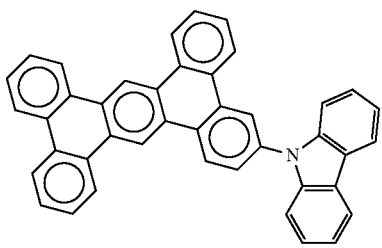
Compound 83
Compound 84
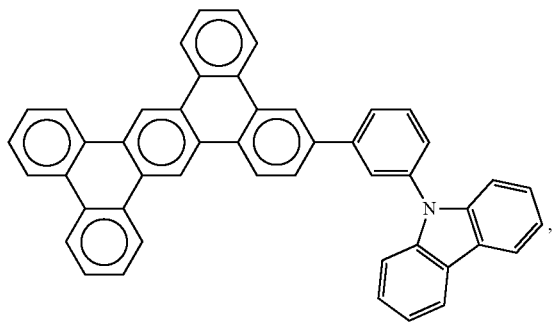

-continued
Compound 85
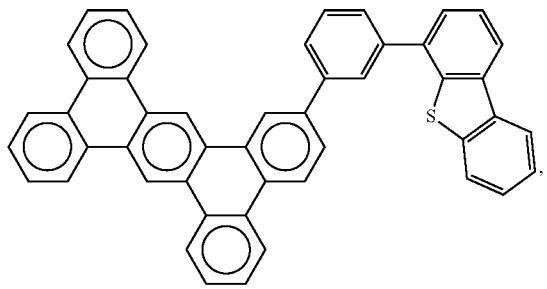
Compound 86
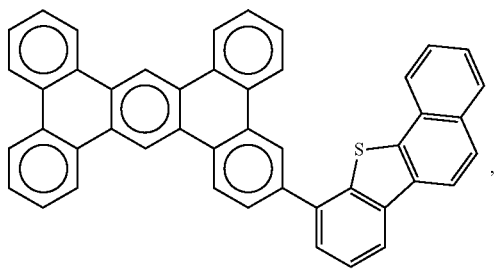
Compound 87
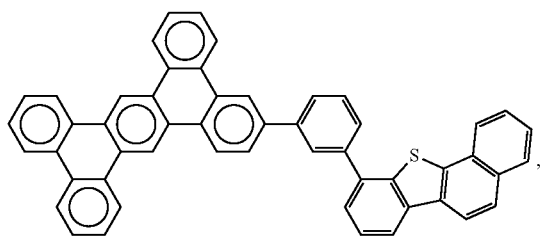
Compound 88
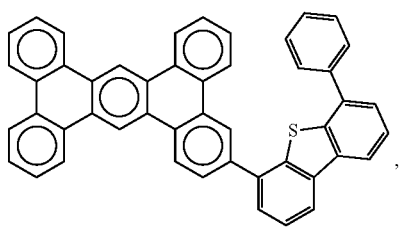
Compound 89
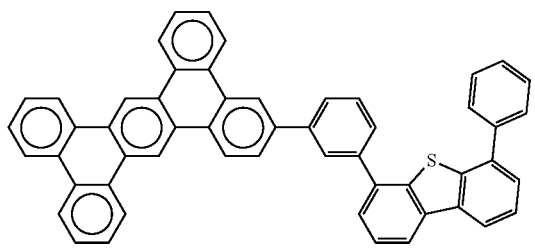
Compound 90
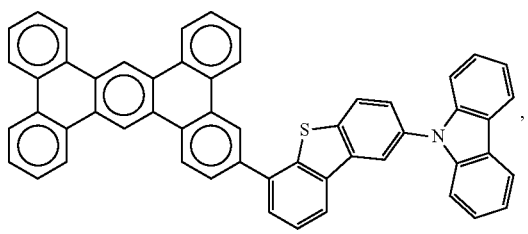
Compound 91
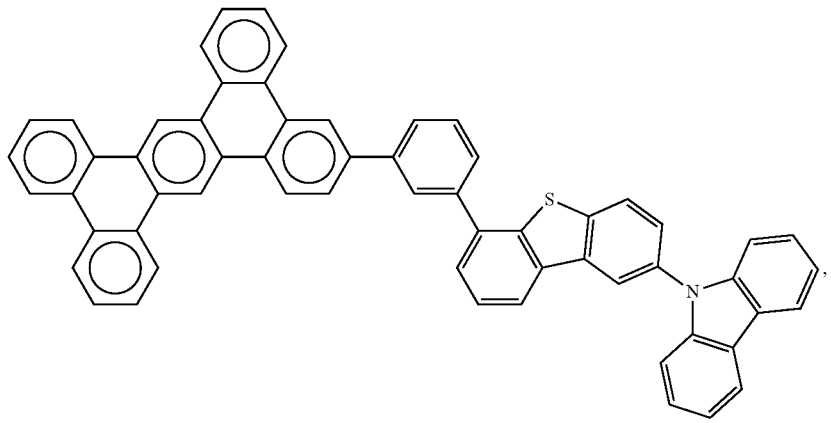
Compound 92
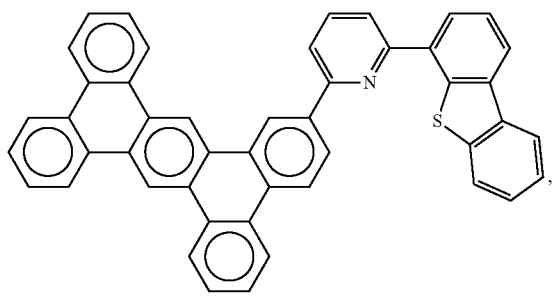
Compound 93
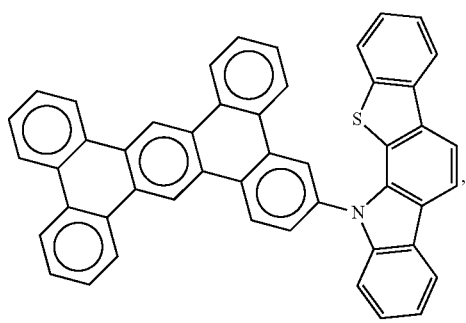

-continued
Compound 94
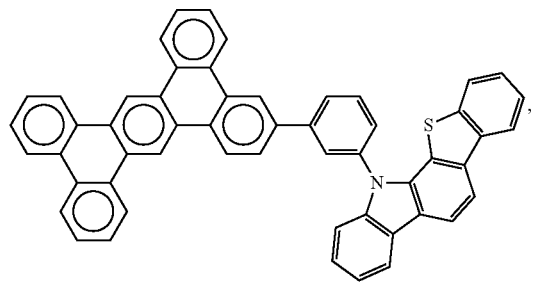
Compound 95
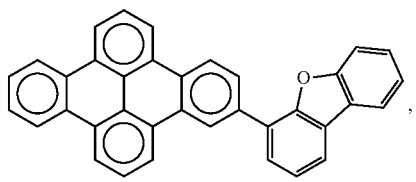
Compound 96
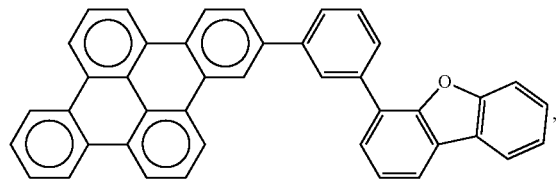
Compound 97
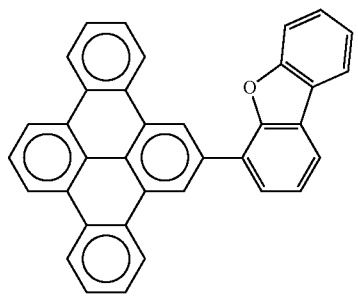
Compound 98
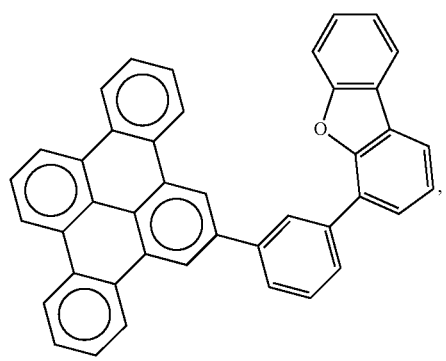
Compound 99
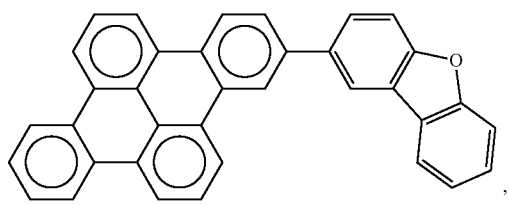
Compound 100
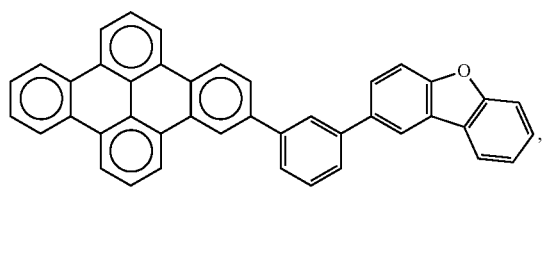
Compound 101
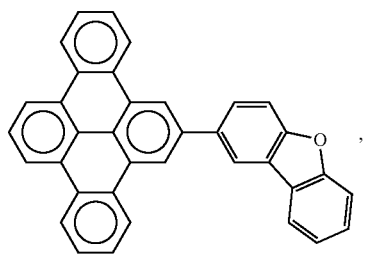
Compound 102
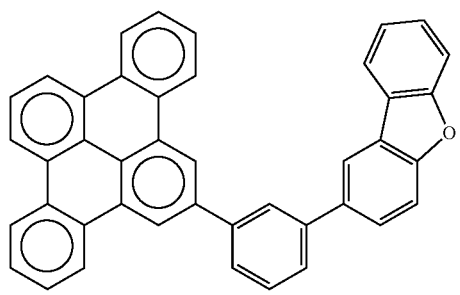
Compound 103
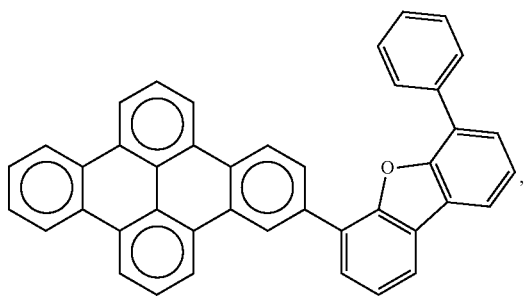

-continued
Compound 104
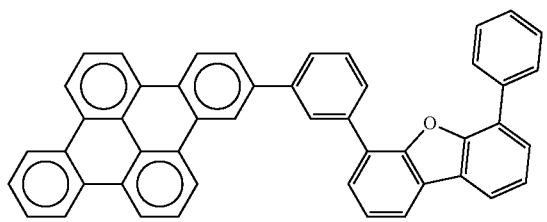
Compound 105
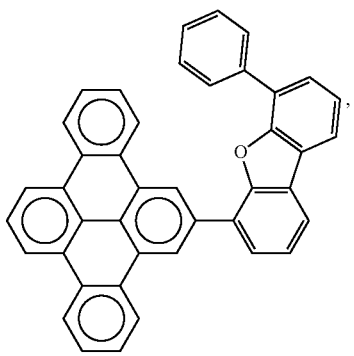
Compound 106
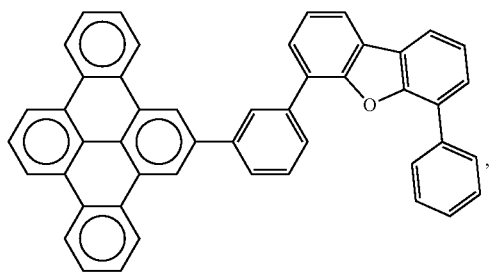
Compound 107
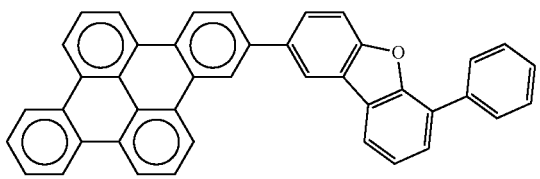
Compound 108
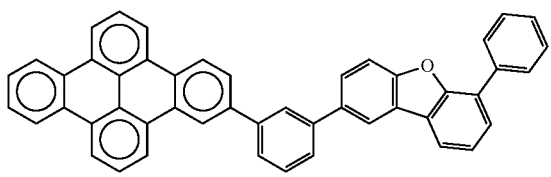
Compound 109
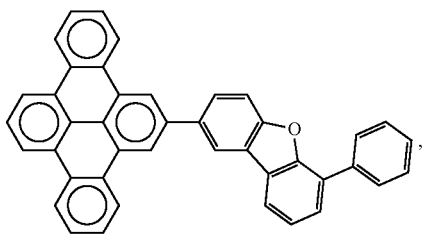
Compound 110
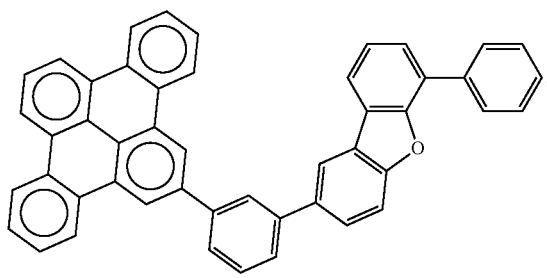
Compound 111
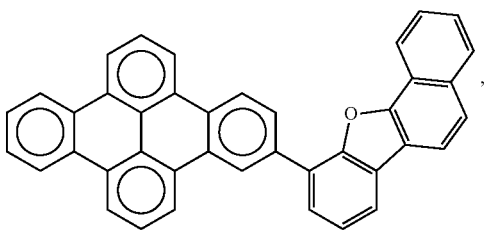
Compound 112
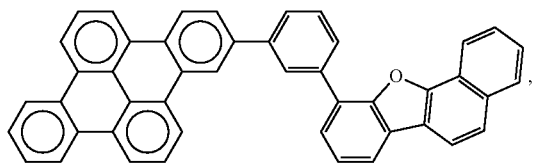
Compound 113
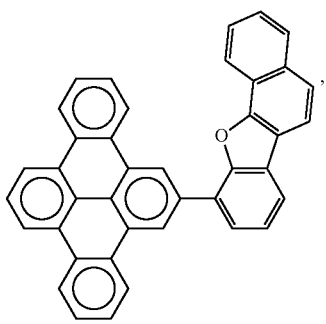

-continued
Compound 114
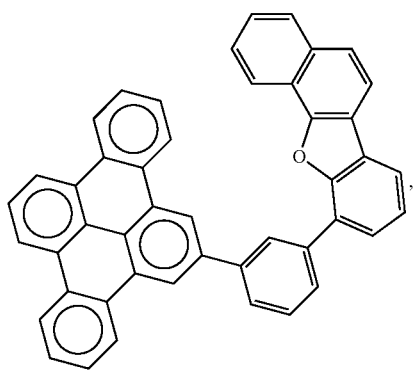
Compound 115
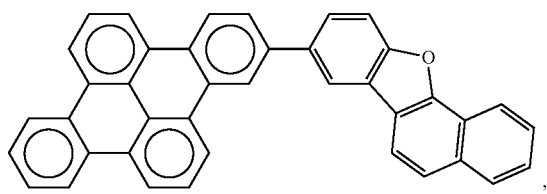
Compound 116
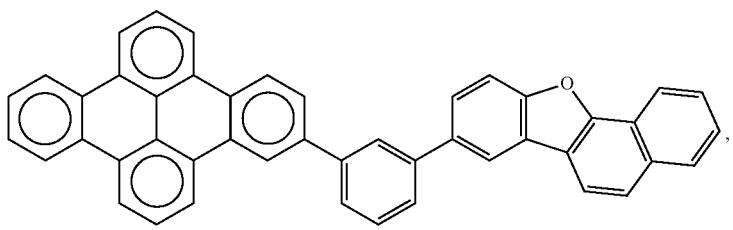
Compound 117
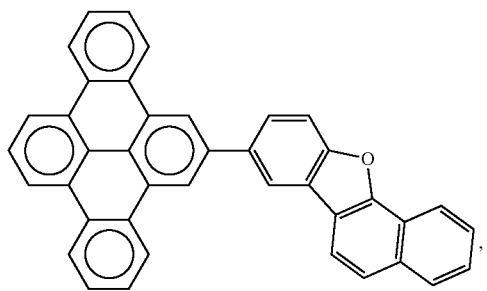
Compound 118
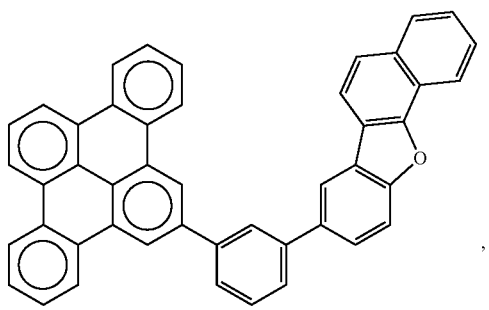
Compound 119
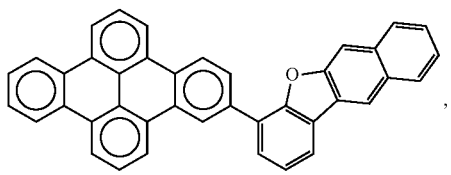
Compound 120
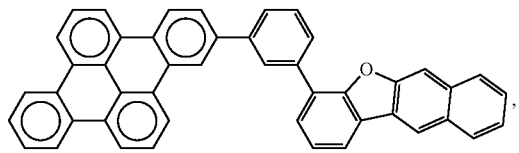
Compound 121
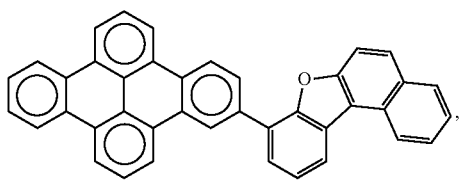
Compound 122
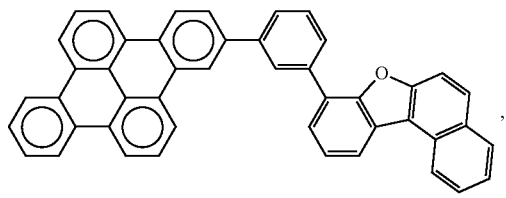

-continued
Compound 123
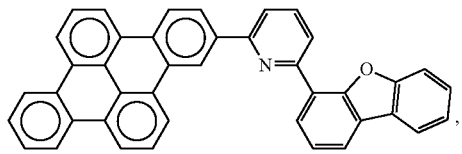
Compound 124
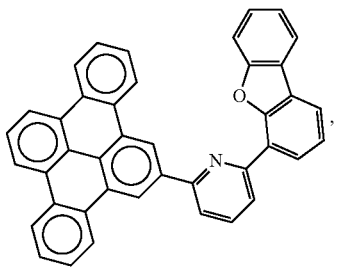
Compound 125
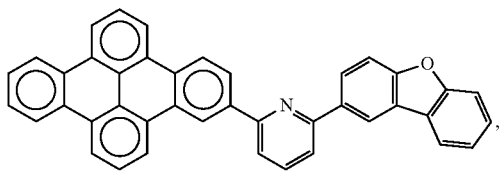
Compound 126
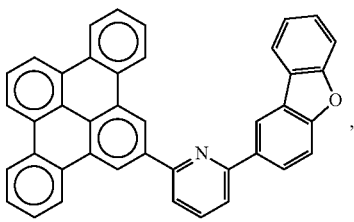
Compound 127
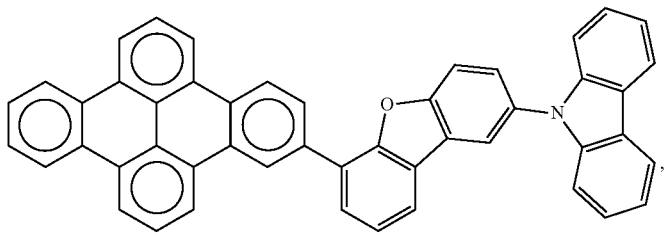
Compound 128
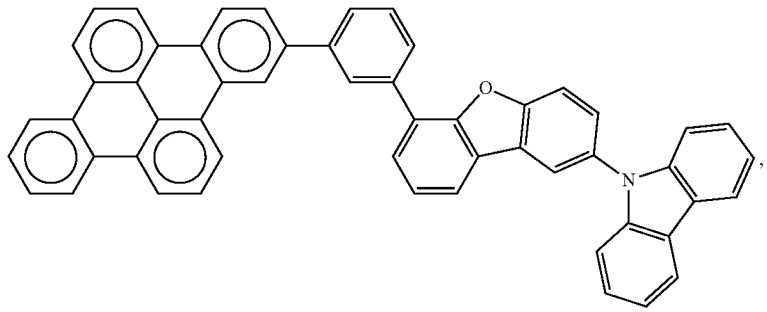
Compound 129
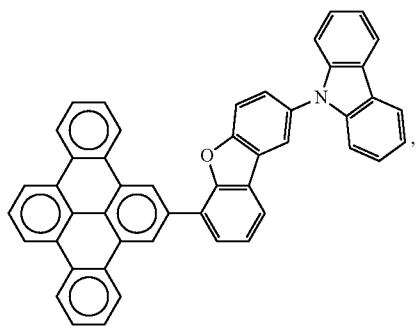
Compound 130
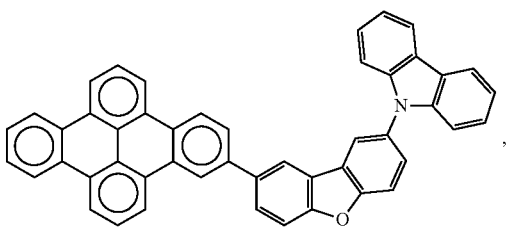

-continued
Compound 131
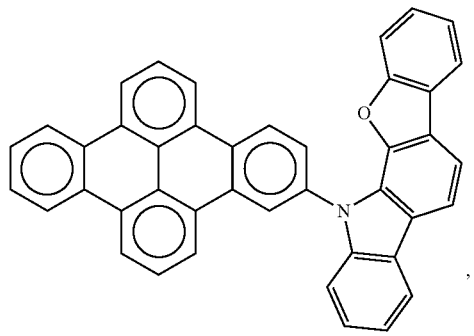
Compound 132
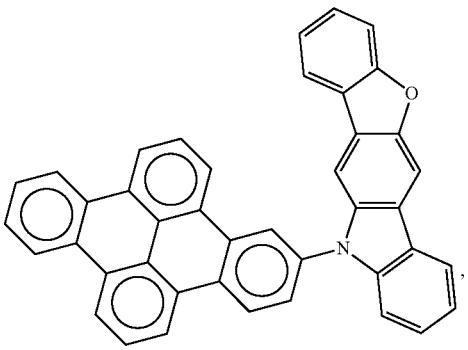
Compound 133
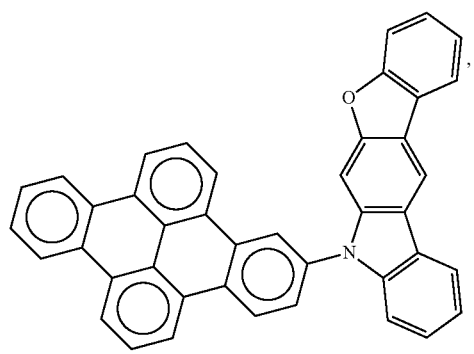
Compound 134
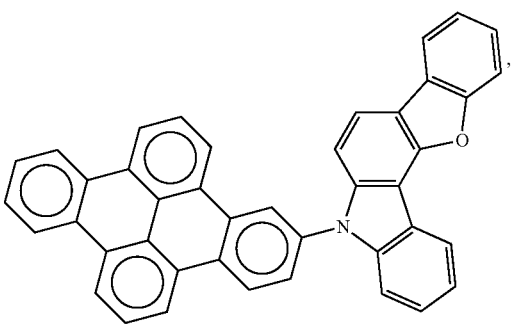
Compound 135
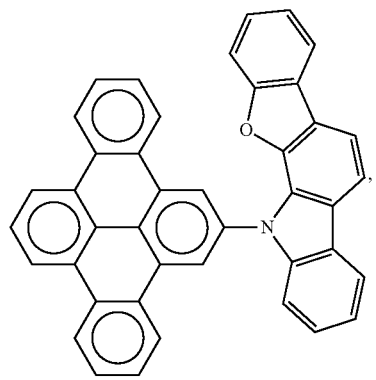
Compound 136
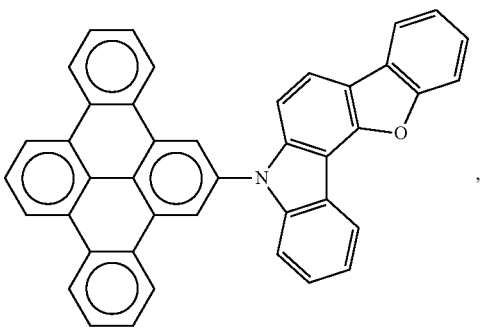
Compound 137
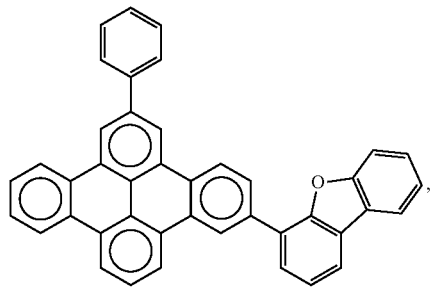
Compound 138
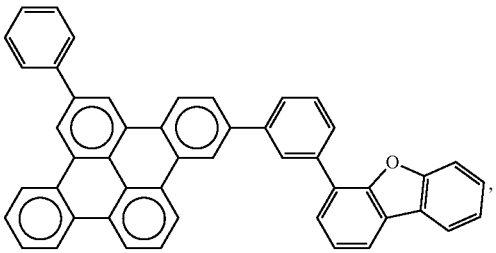

-continued
Compound 139
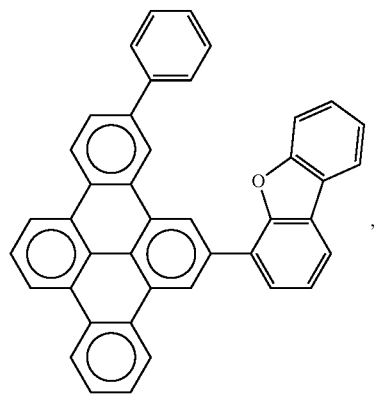
Compound 140
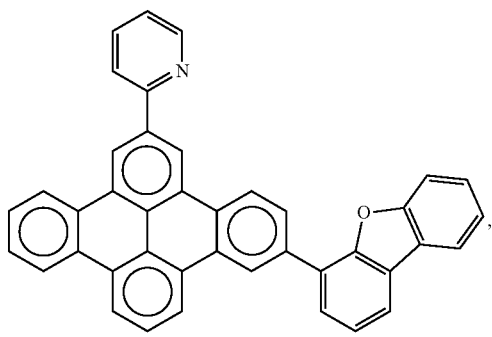
Compound 141
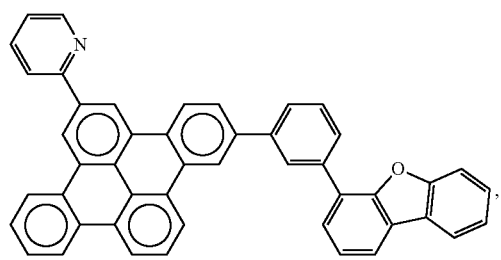
Compound 142
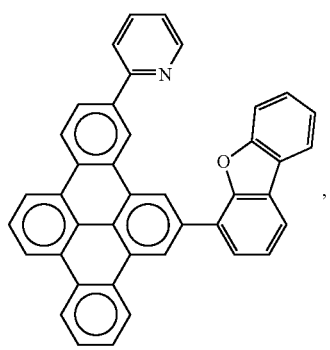
Compound 143
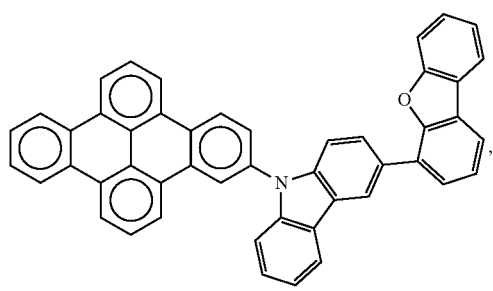
Compound 144
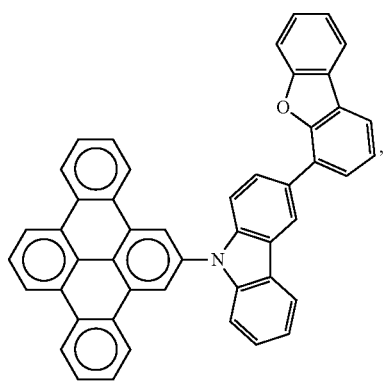
Compound 145
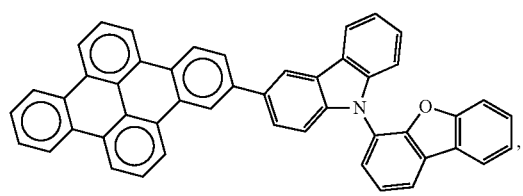
Compound 146
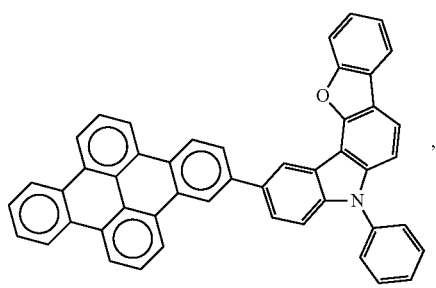

-continued
Compound 147
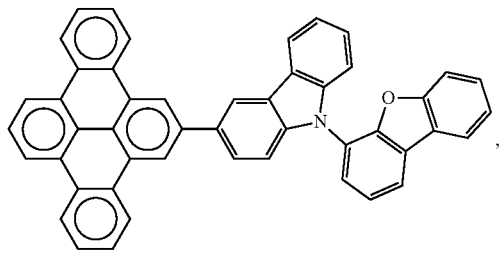
Compound 148
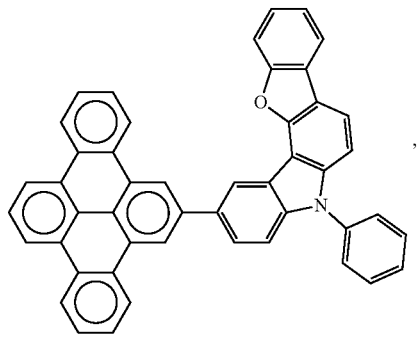
Compound 149
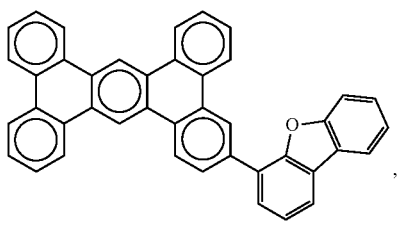
Compound 150
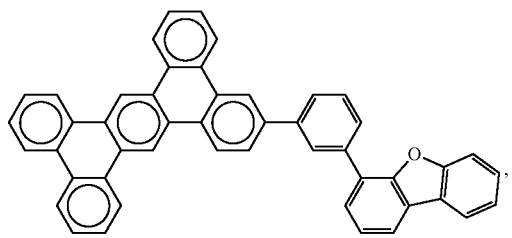
Compound 151
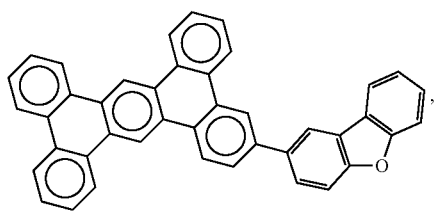
Compound 152
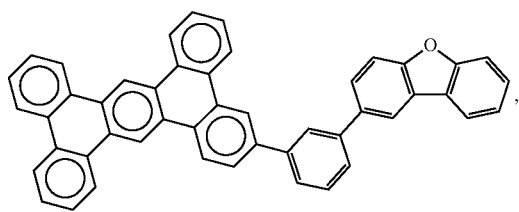
Compound 153
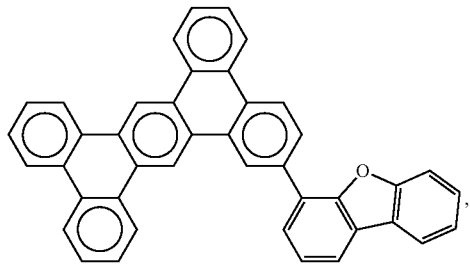
Compound 154
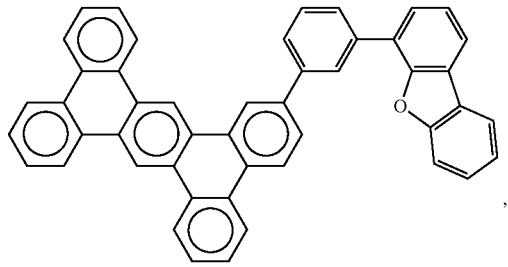
Compound 155
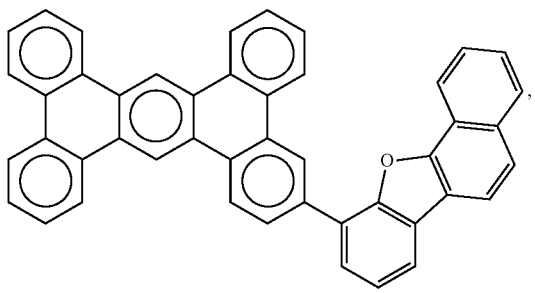

-continued
Compound 156
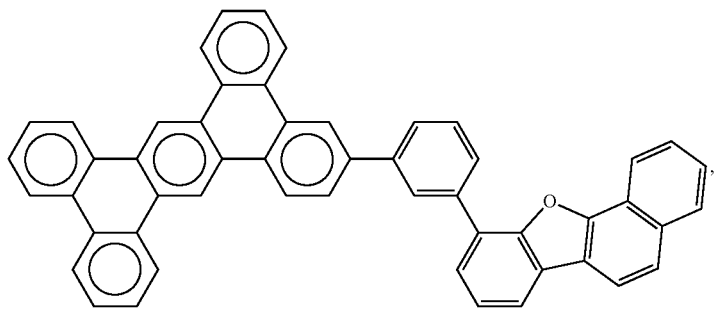
Compound 157
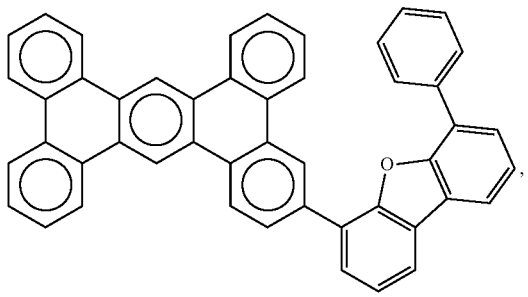
Compound 158
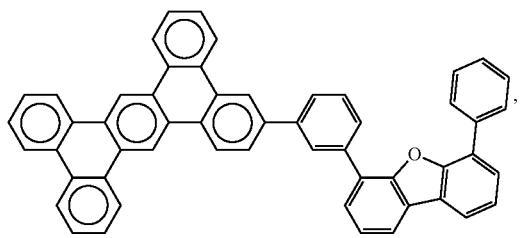
Compound 159
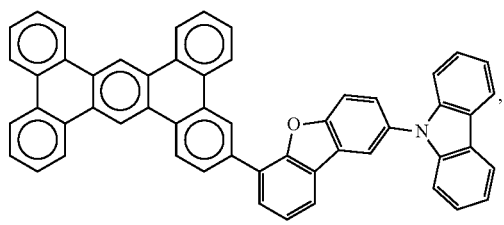
Compound 160
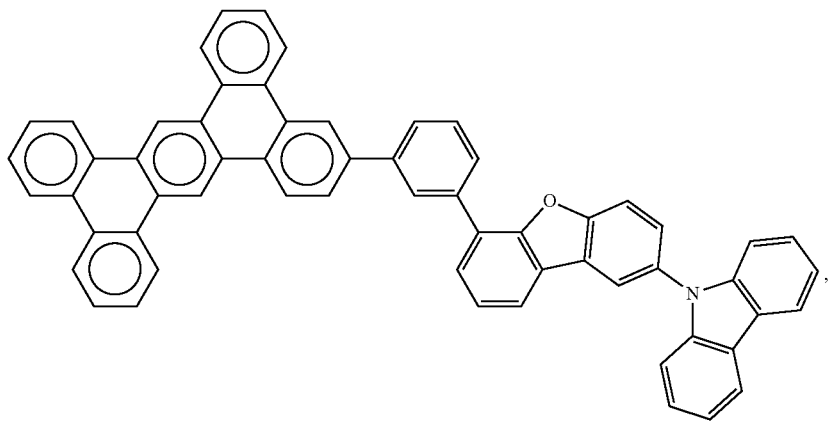
Compound 161
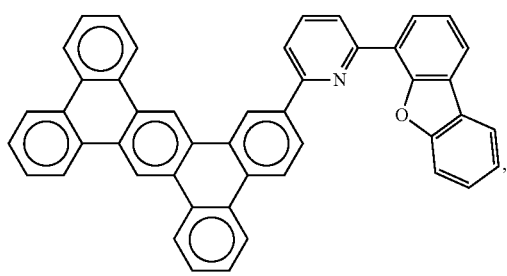
Compound 162
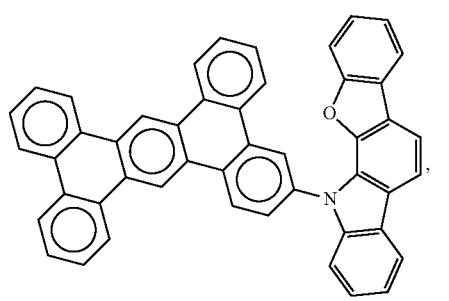
and -continued

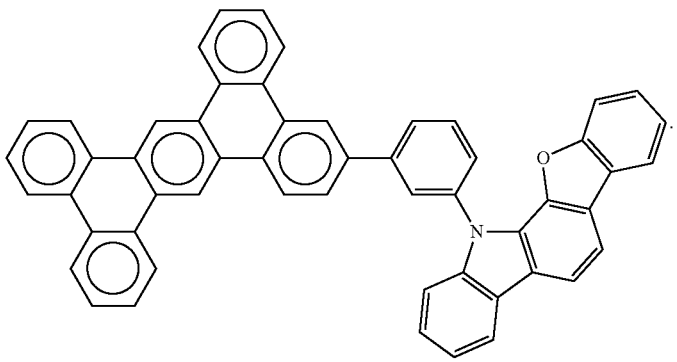

Compound 163

According to another aspect of the present disclosure, a first device comprising a phosphorescent organic light-emitting device is disclosed. The phosphorescent organic light-emitting device comprises: an anode; a cathode; and an organic layer, disposed between the anode and the cathode, comprising a compound containing an all-benzenoid group having at least 24 carbon atoms.

In one embodiment of the first device, the compound has a formula (I):

A-L-B                  (I), wherein A contains a group selected from the group consisting of indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, azatriphenylene, and combinations thereof, which are optionally further substituted with one or more groups selected from hydrogen, deuterium, alkyl, cycloalkyl, arylalkyl, alkoxy, aryloxy, amino, silyl, aryl, heteroaryl, and combinations thereof;

wherein the substitution of one or more groups in A is optionally fused to the indole, carbazole, benzofuran, dibenzofuran, benzothiophene, dibenzothiophene, benzoselenophene, dibenzoselenophene, triphenylene, azacarbazole, azadibenzofuran, azadibenzothiophene, azadibenzoselenophene, or azatriphenylene group;

wherein L is a single bond or comprises an aryl or heteroaryl group having from 5-30 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof; and wherein B is an all-benzenoid group having at least 24 carbon atoms, which are optionally further substituted with one or more groups selected from hydrogen, deuterium, alkyl, cycloalkyl, arylalkyl, alkoxy, aryloxy, amino, silyl, aryl, heteroaryl, and combinations thereof.

In one embodiment of the first device, the organic layer is an emissive layer and the compound of the formula (I) is a host. The organic layer can further comprise a phosphorescent emissive dopant.

In one embodiment of the first device, the phosphorescent emissive dopant is a transition metal complex having at least one ligand selected from the group consisting of:

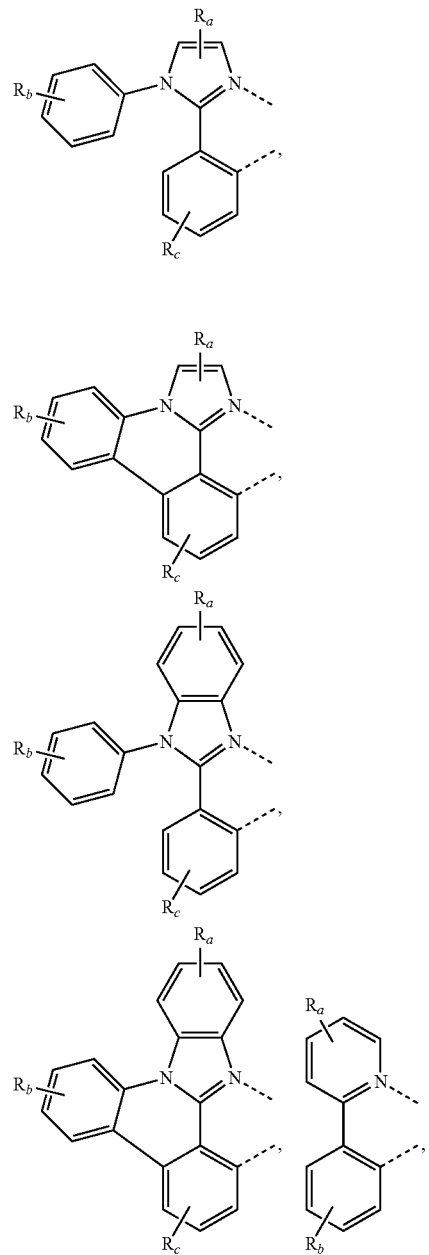

-continued

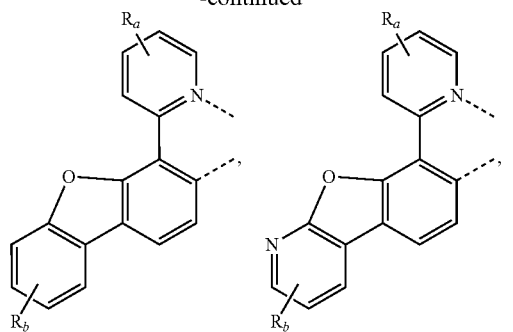
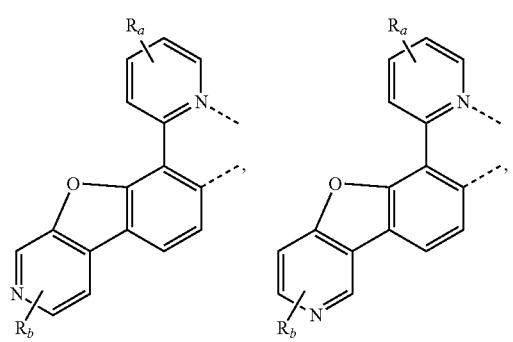
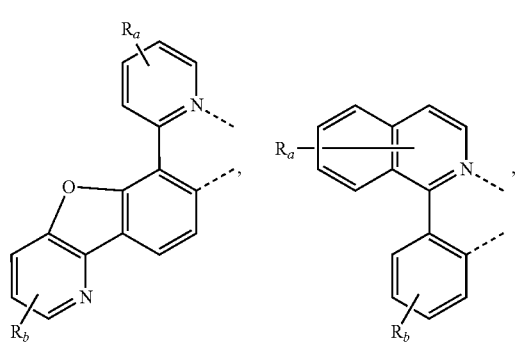
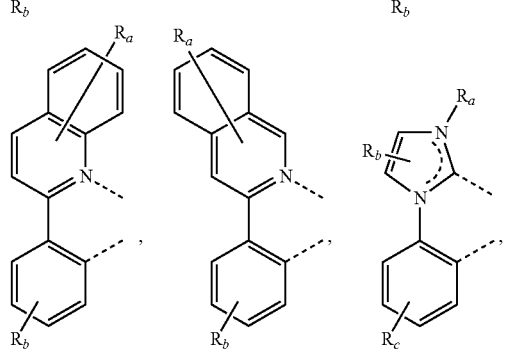
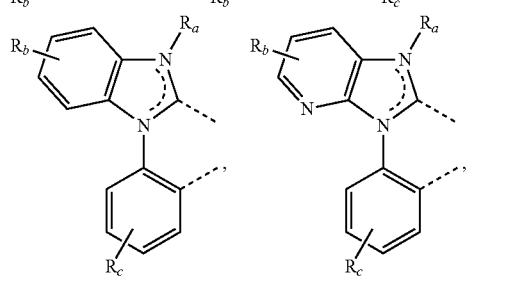

-continued

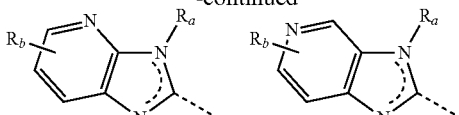
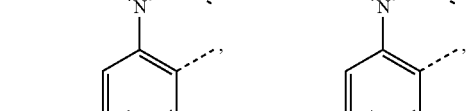
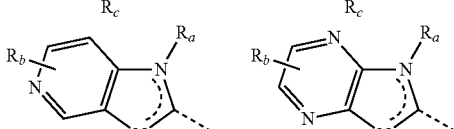
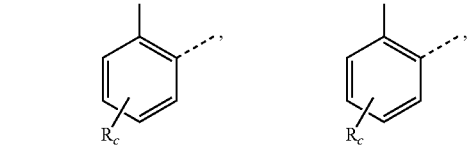
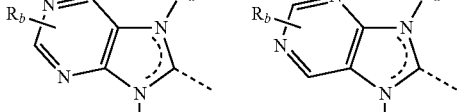
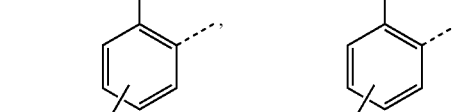
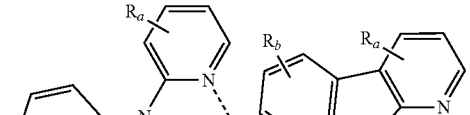
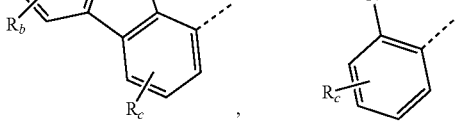
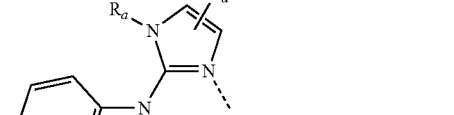, and
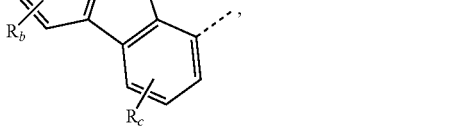

wherein $R_a$, $R_b$, $R_c$, and $R_d$ may represent mono, di, tri, or tetra substitution, or no substitution; wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In one embodiment of the first device, the organic layer is a blocking layer and the compound is a blocking material in the organic layer. Inn another embodiment, the organic layer is an electron transporting layer and the compound is an electron transporting material in the organic layer.

In one embodiment of the first device, the first device is a consumer product. In another embodiment, the first device is an organic light-emitting device. In another embodiment, the first device can comprise a lighting panel.

Synthesis of the Novel Compounds

Synthesis of triphenylen-1-ol

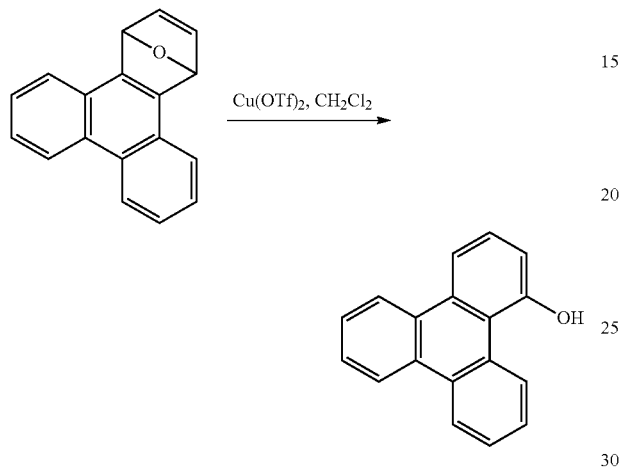

To a solution of 1,4-dihydro-1,4-epoxytriphenylene (3 g, 12 mmol), copper(II) triflate (0.45 g, 1.2 mmol), and dry dichloromethane (120 mL) in a 250 mL round bottom flask equipped with a stir bar and nitrogen inlet was allowed to stir overnight at room temperature. The reaction mixture was quenched by deionized water, followed by dichloromethane extraction and the organic layer was dried over magnesium sulfate and filtered through filter paper. The solvent was then evaporated and the residue was then purified by flash column chromatography using DCM:hexane (1:2, v/v) as eluent. The resulting white solid was recrystallized from hexane to obtain 2.7 g (90%) of triphenylen-1-ol.

Synthesis of triphenylen-1-yl trifluoromethanesulfonate

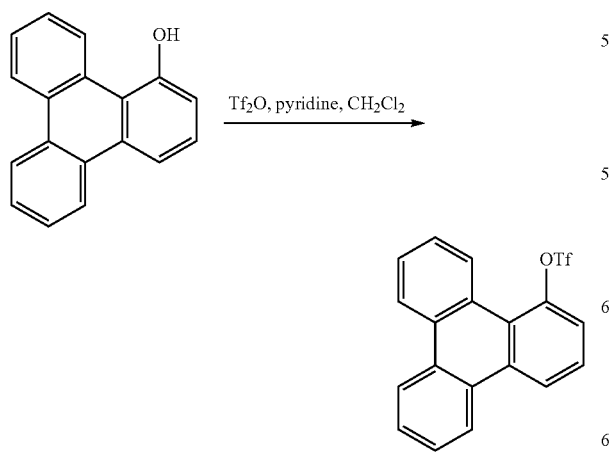

To a cooled solution (0° C.) of triphenylen-1-ol (2 g, 8.2 mmol), pyridine (8 mL) and dry dichloromethane (200 mL) in a 250 mL round bottom flask equipped with a stir bar and nitrogen inlet was added dropwise trifluoromethanesulfonyl anhydride (10 mL). The reaction mixture was allowed to stir overnight at room temperature. The reaction mixture was cooled to 0° C. and quenched by deionized water and the organic layer was dried over magnesium sulfate and filtered through filter paper. The solvent was then evaporated and the residue was then purified by column using DCM:hexane (1:4, v/v) as eluent. The resulting white solid was recrystallized from hexane, 2.7 g (88%) of triphenylen-1-yl trifluoromethanesulfonate was collected.

Synthesis of 1-(3-methoxyphenyl)triphenylene

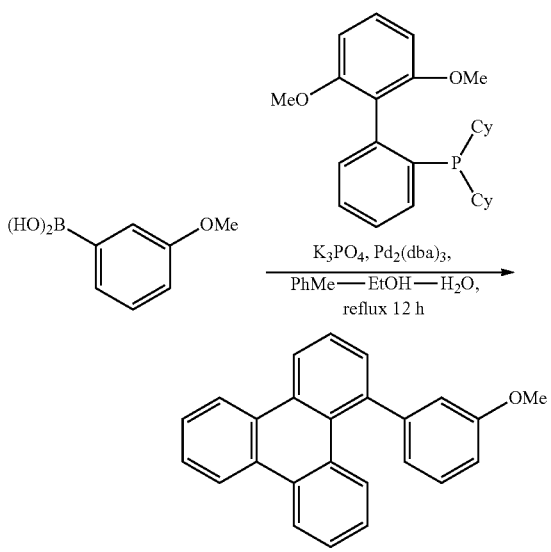

To a solution of triphenylen-1-yl trifluoromethanesulfonate (2.42 g, 6.42 mmol), 3-methoxyphenylboronic acid (1.96 g, 12.9 mmol), 2-dicyclohexylphosphino-2',6'-dimethoxybiphenyl (0.34 g, 0.83 mmol), $K_3PO_4$ (4.20 g, 19.8 mmol) in toluene (90 mL), ethanol (5 mL) and water (5 mL) was bubbled with nitrogen for 30 min. $Pd_2(dba)_3$ (0.24 g, 0.26 mmol) was added. The mixture was bubbled with nitrogen for 15 min. The resultant mixture was refluxed for 4 h. After cooling, the reaction mixture was filtered through a short silica pad and magnesium sulphate and washed with toluene. The solvent was removed in vacuo and the residue was purified by flash chromatography using 15% toluene/hexane to afford 2.04 g (95%) of 1-(3-methoxyphenyl)triphenylene as a white foam.

Synthesis of 5-Methoxydibenzo[fg,op]tetracene

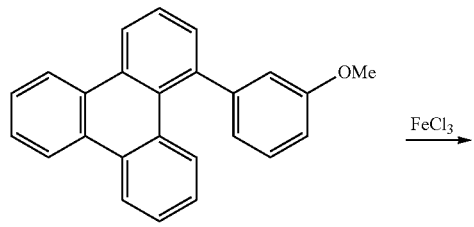

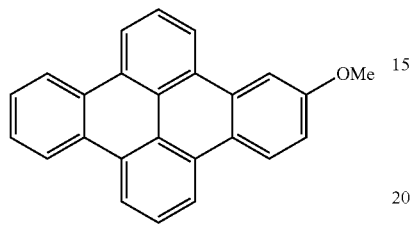

In a 50 mL round-bottom flash equipped with a nitrogen inlet and a stirring bar, 1-(3-methoxyphenyl)triphenylene (2.04 g, 6.10 mmol) was dissolved in anhydrous methylene chloride (20 mL). Iron(III) chloride (2.90 g, 17.9 mmol) was added and the mixture was stirred overnight. Methanol was added and stirred for 2 h. The solid was filtered and heated to boil with toluene (200 mL). The residue was filtered through a silica pad while hot and washed with toluene and concentrated to give 2.06 g of brown solid. The brown solid was recrystallized with toluene/heptane (1:1, 50 mL) twice to give 1.39 g (69%) of 5-methoxydibenzo[fg,op]tetracene.

Synthesis of 5-dibenzo[fg,op]tetracene trifluoromethanesulfonate

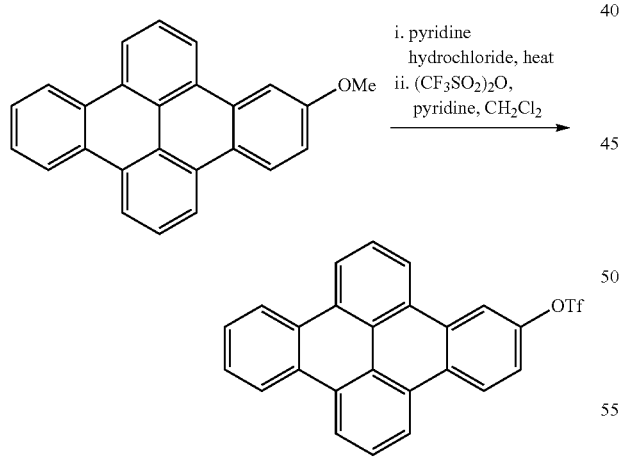

A mixture of 5-methoxydibenzo[fg,op]tetracene (1.39 g, 4.20 mmol) and pyridine hydrochloride (3.77 g, 32.7 mmol) was heated to melt for 2 hours. Upon cooling, water was added and the precipitate was filtered and dried to give 1.278 g of brown solid residue which was used for the next step without further purification.

To the above brown solid residue was added anhydrous dicholoromethane (20 mL) and anhydrous pyridine (2.7 mL, 13.6 mmol) at 0° C. After 10 min, trifluoromethanesulfonic anhydride (2.8 mL, 16.6 mmol) was added slowly via syringe. The solution was warmed to room temperature and stirred overnight. The reaction mixture was added water (5 mL) at 0° C. and extracted with toluene, dried with MgSO$_4$ and filtered thru a short silica pad and washed with hot toluene and concentrated to give yellow powder. The yellow powder was recrystallized with heptane/toluene (3:1, 40 mL) twice to give 1.54 g (82%) of 5-dibenzo[fg,op]tetracene trifluoromethanesulfonate.

Synthesis of Compound 2-X

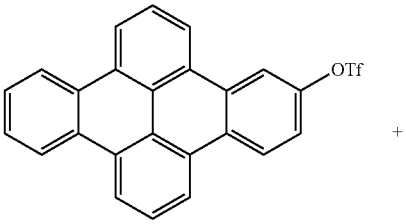

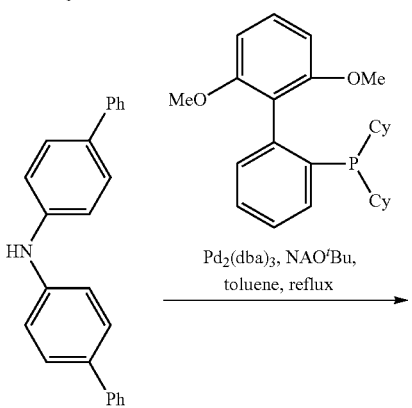

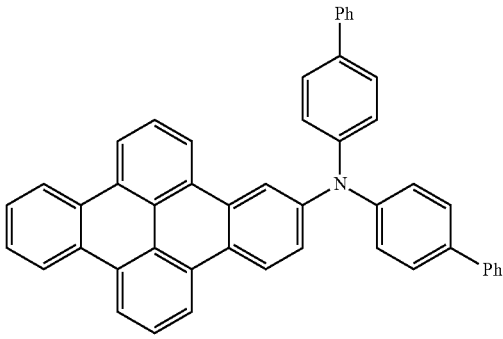 [SMILES: c1ccc(-c2ccc(N(c3ccc(-c4ccccc4)cc3)c3ccc4c(c3)c3cccc5c6ccccc6c6cccc4c6c53)cc2)cc1]

5-Dibenzo[fg,op]tetracene trifluoromethanesulfonate (1.10 g, 2.43 mmol), bis-biphenyl-4-yl-amine (0.82 g, 1.22 mmol) were mixed in dry toluene (80 mL). The solution was bubbled nitrogen while stirring for 15 min. Pd$_2$(dba)$_3$ (0.06 g, 0.07 mmol), 2-dicyclohexylphosphino-2',6'-dimethoxybiphenyl (0.11 g, 0.28 mmol) and sodium tert-butoxide (0.46 g, 4.83 mmol) were added in sequence. The mixture was heated to reflux overnight under nitrogen. After cooling, the reaction mixture was filtered through a short silica pad and washed with hot toluene, the solvent was concentrated. The residue was recrystallized with toluene (30 mL) twice to obtain 1.21 g (80%) of Compound 2-X.

Synthesis of Compound 2-Y (ST notebook 95129406 page 68)

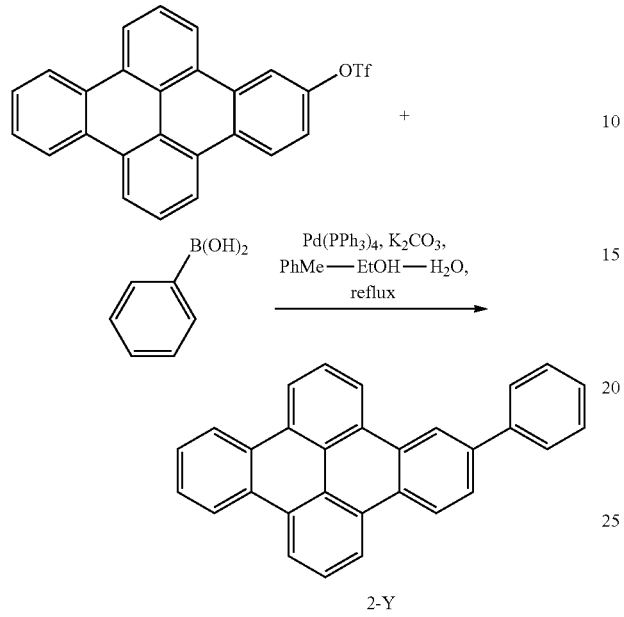

2-Y

5-Dibenzo[fg,op]tetracene trifluoromethanesulfonate (0.17 g, 0.39 mmol), phenylboronic acid (0.06 g, 0.48 mmol), K$_2$CO$_3$ (0.14 g, 1.00 mmol) in toluene (3 mL), water (1 mL) and EtOH (1 mL) was bubbled with nitrogen for 30 min. Pd(PPh$_3$)$_4$ (0.014 g, 0.01 mmol) was added. The mixture was bubbled with nitrogen for 15 min. The resultant mixture was refluxed for 15 hours. After cooling, the reaction mixture was extracted with toluene and filtered through a short silica pad and washed with hot toluene. The solvent was concentrated. The residue was recrystallized with heptane-tolune (3:1, 4 mL) to give 0.04 g (27%) of Compound 2-Y.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoO$_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

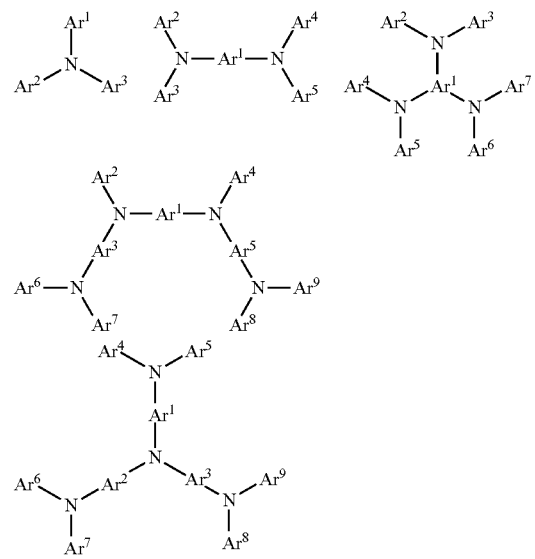

Each of Ar$^1$ to Ar$^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar$^1$ to Ar$^9$ is independently selected from the group consisting of:

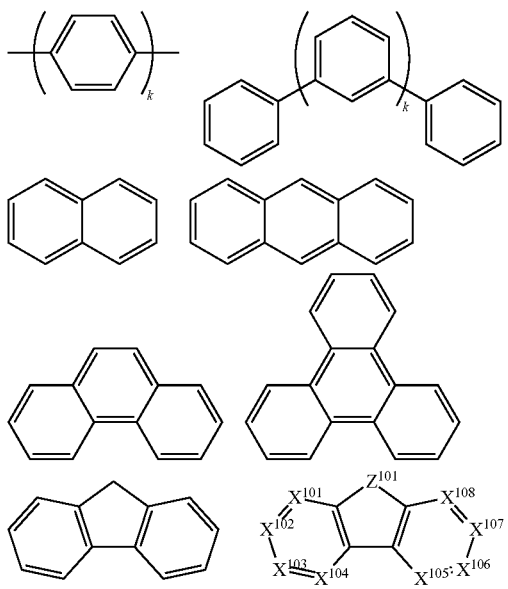

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

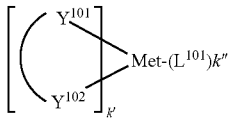

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

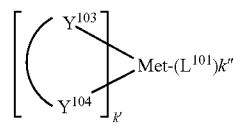

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

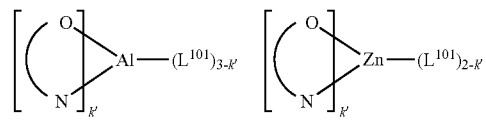

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

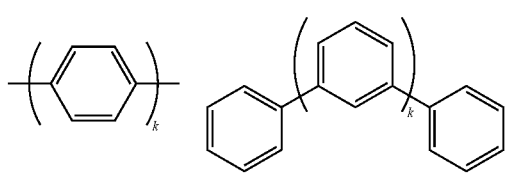

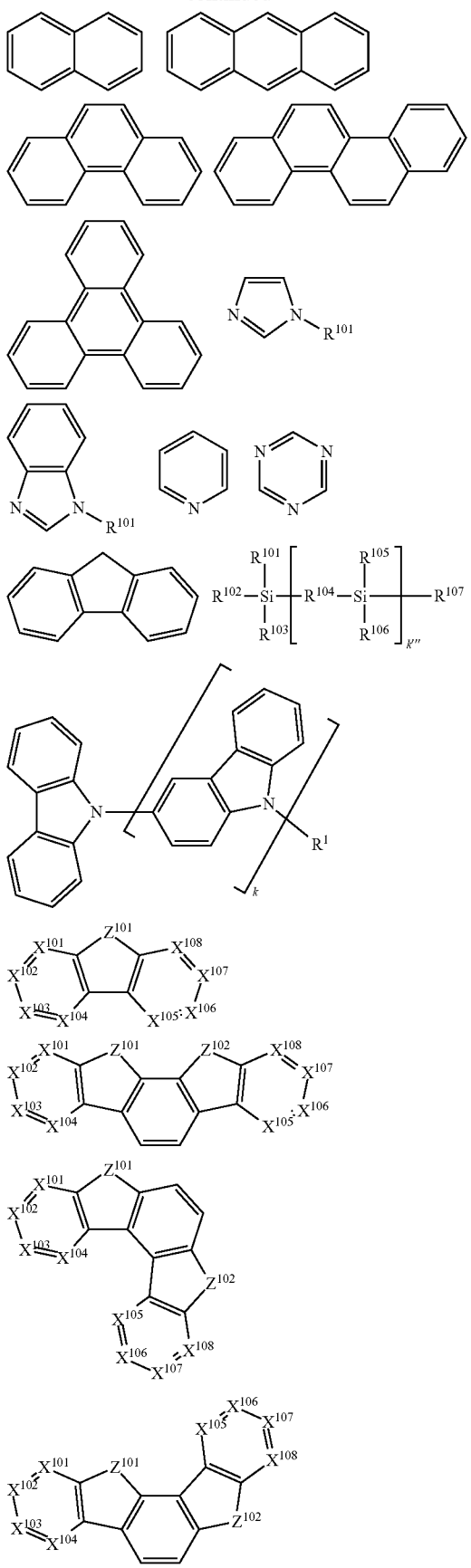

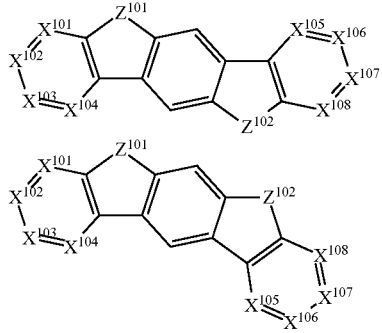

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

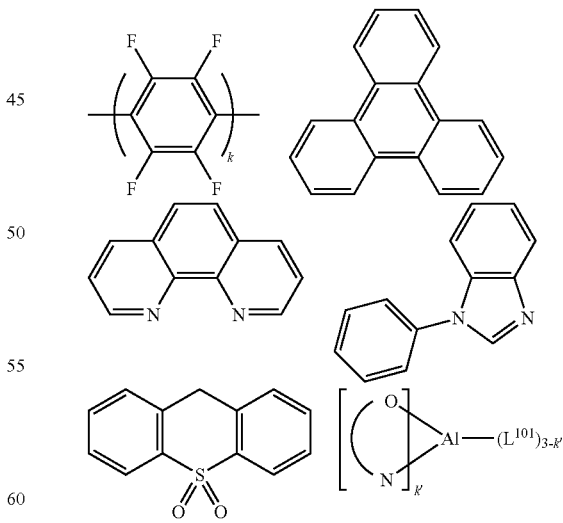

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

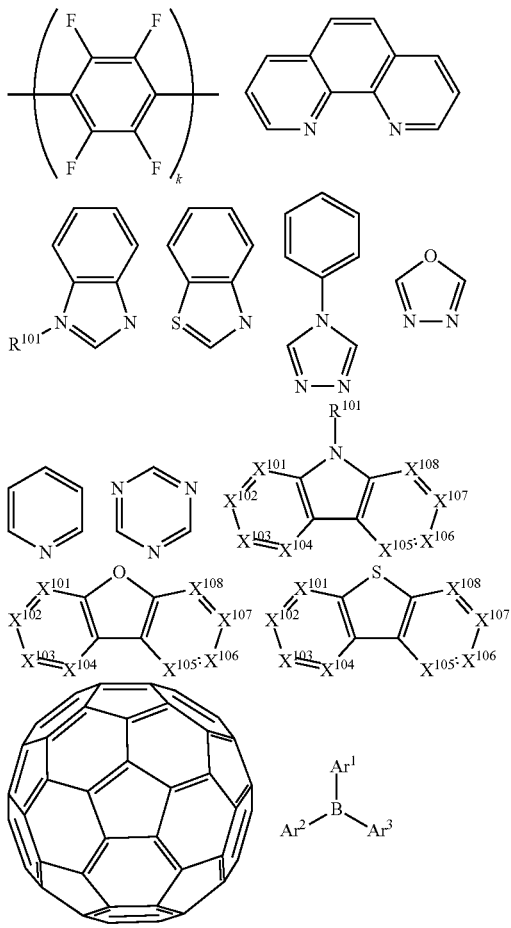

wherein $R^{101}$ is selected from the group consisting of hydrogen, deuterium, halide, alkyl, cycloalkyl, heteroalkyl, aryl- alkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

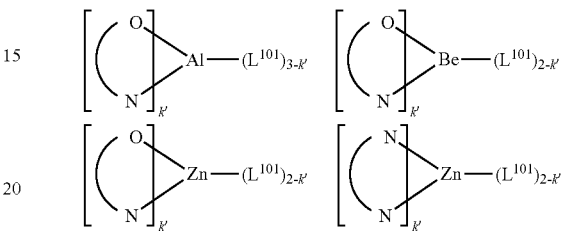

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
|---|---|---|
| | Hole injection materials | |
| Pthalocyanine and porphyrin compounds | 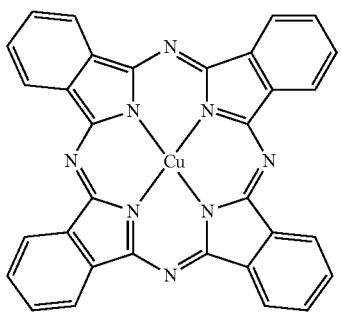 | Appl. Phys. Lett. 69, 2160 (1996) |

TABLE 2-continued

| MATERIAL | EXAMPLES OF MATERIAL | PUBLICATIONS |
|---|---|---|
| Starburst triarylamines | | J. Lumin. 72-74, 985 (1997) |
| $CF_x$ Fluorohydrocarbon polymer | $-\!\!+\!CH_xF_y\!+\!_n\!-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |
| Triarylamine or polythiophene polymers with conductivity dopants | | EP1725079A1 and |

TABLE 2-continued
| MATERIAL | EXAMPLES OF MATERIAL | PUBLICATIONS |
|---|---|---|
|  | 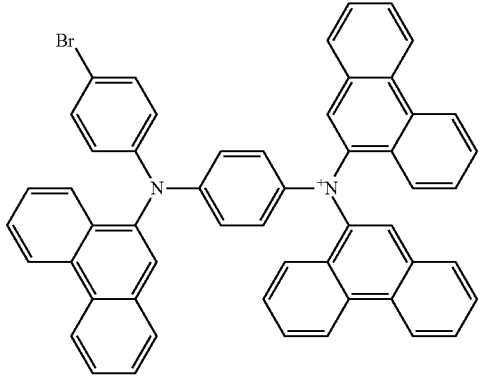 [SMILES: Brc1ccc(N(c2ccc([NH+](c3cc4ccccc4c4ccccc34)c3cc4ccccc4c4ccccc34)cc2)c2cc3ccccc3c3ccccc23)cc1] |  |
|  | 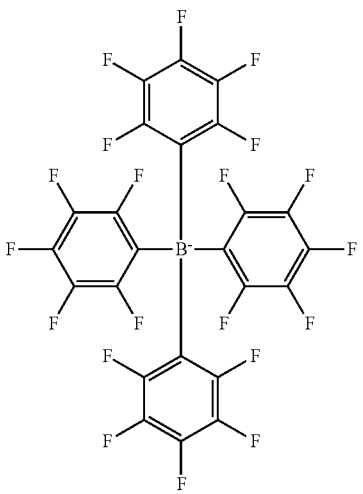 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] |  |
| Organic compounds with conductive inorganic compounds, such as molybdenum and tungsten oxides | 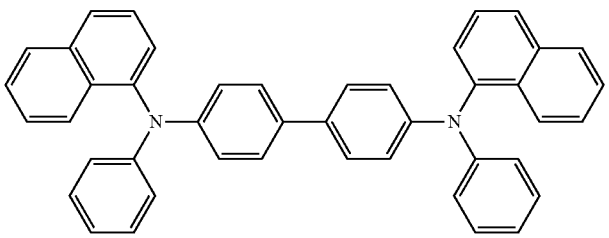 | US20050123751 SID Symposium Digest, 37, 923 (2006) WO2009018009 |
| n-type semiconducting organic complexes | 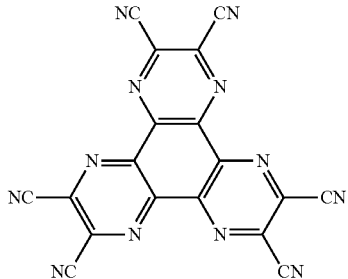 [SMILES: N#Cc1nc2c3nc(C#N)c(C#N)nc3c3nc(C#N)c(C#N)nc3c2nc1C#N] | US20020158242 |

TABLE 2-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| | | |
| --- | --- | --- |
| Triarylamines (e.g., TPD, α-NPD) | | Appl. Phys. Lett. 51, 913 (1987) |

TABLE 2-continued
| MATERIAL | EXAMPLES OF MATERIAL | PUBLICATIONS |
|---|---|---|
| | 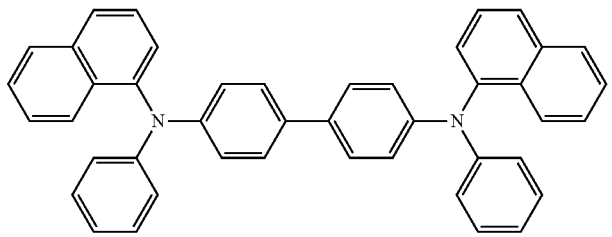 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 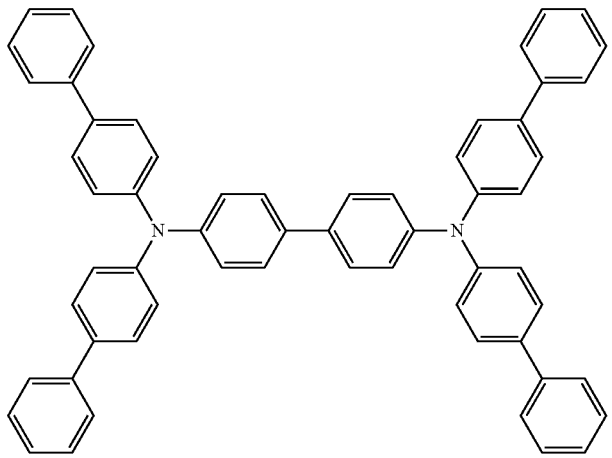 | EP650955 |
| | 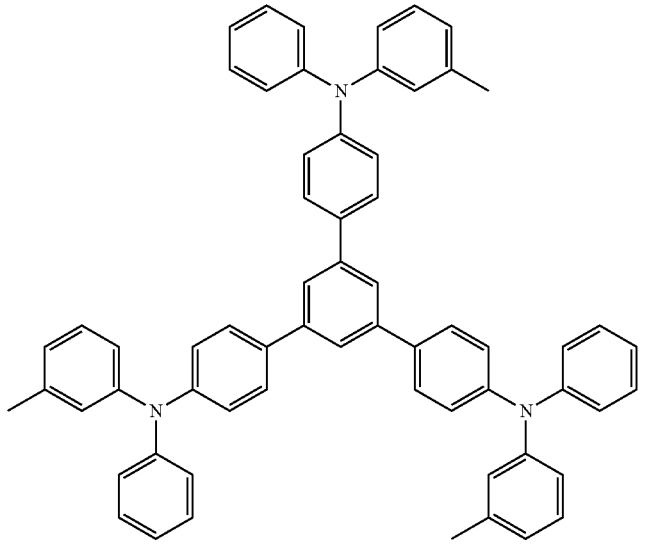 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 2-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 2-continued
| MATERIAL | EXAMPLES OF MATERIAL | PUBLICATIONS |
| --- | --- | --- |
| Triarylamine with (di)benzothiophene/ (di)benzofuran | 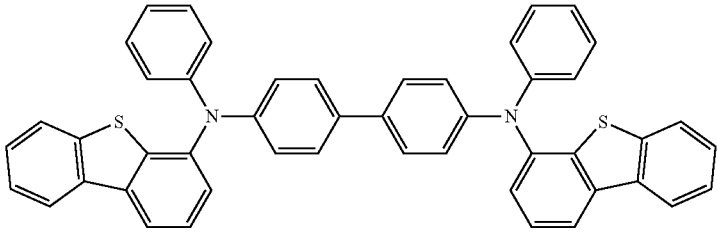 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 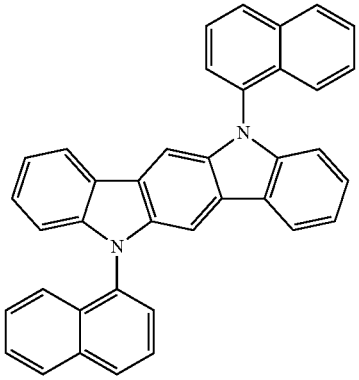 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 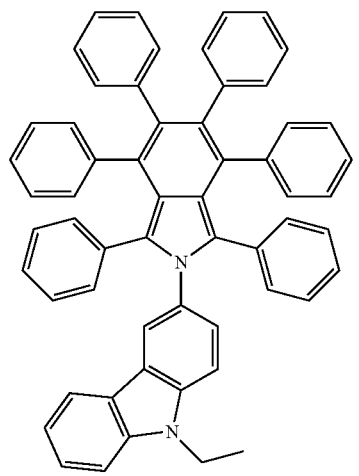 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 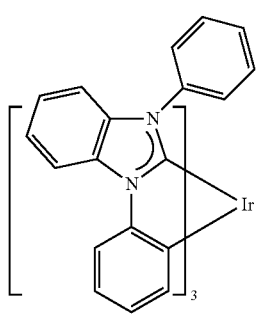 | US20080018221 |

TABLE 2-continued

| MATERIAL | EXAMPLES OF MATERIAL | PUBLICATIONS |
| --- | --- | --- |
| | Phosphorescent OLED host materials | |
| | Red hosts | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

| MATERIAL | EXAMPLES OF MATERIAL | PUBLICATIONS |
|---|---|---|
| Aromatic fused rings | 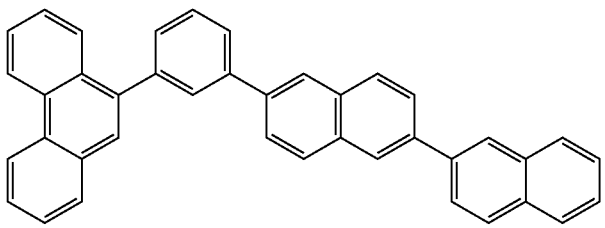 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 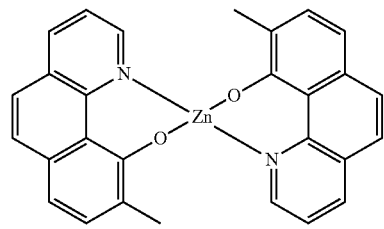 | WO2010056066 |
| Chrysene based compounds | 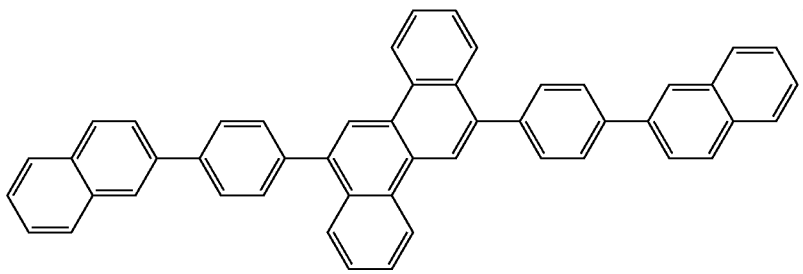 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| Green hosts | | |
| Arylcarbazoles | 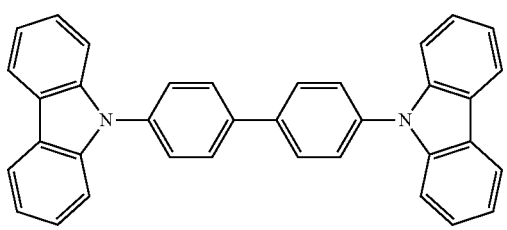 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 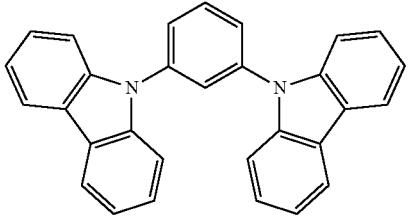 [SMILES: c1cc(-n2c3ccccc3c3ccccc32)cc(-n2c3ccccc3c3ccccc32)c1] | US20030175553 |
| | 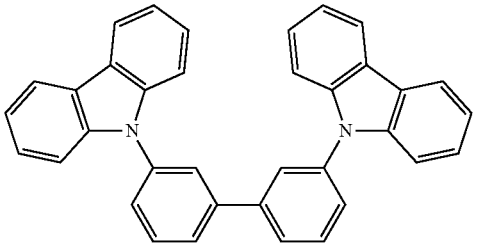 [SMILES: c1cc(-c2cccc(-n3c4ccccc4c4ccccc43)c2)cc(-n2c3ccccc3c3ccccc32)c1] | WO2001039234 |

106
TABLE 2-continued
| MATERIAL | EXAMPLES OF MATERIAL | PUBLICATIONS |
|---|---|---|
| Aryltriphenylene compounds | 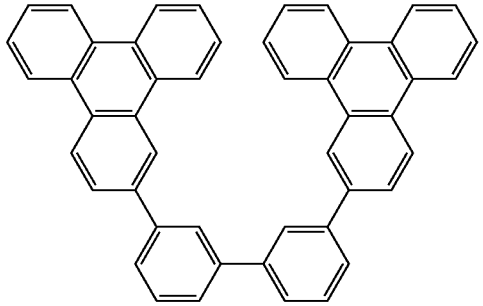 [SMILES: c1cc(-c2cccc(-c3ccc4c5ccccc5c5ccccc5c4c3)c2)cc(-c2ccc3c4ccccc4c4ccccc4c3c2)c1] | US20060280965 |
|  | 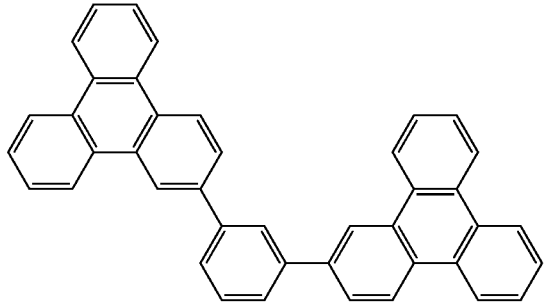 [SMILES: c1cc(-c2ccc3c4ccccc4c4ccccc4c3c2)cc(-c2ccc3c4ccccc4c4ccccc4c3c2)c1] | US20060280965 |
|  | 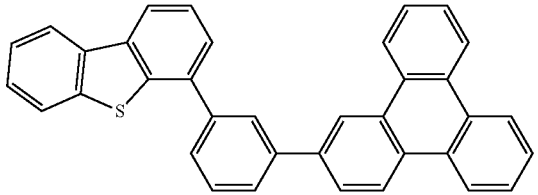 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 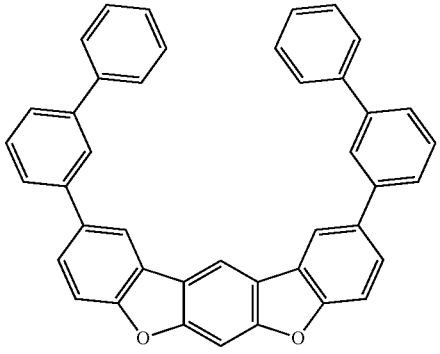 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 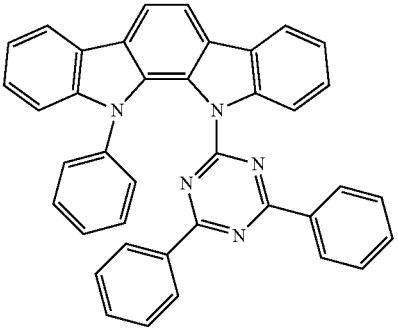 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 2-continued
| MATERIAL | EXAMPLES OF MATERIAL | PUBLICATIONS |
|---|---|---|
|  | 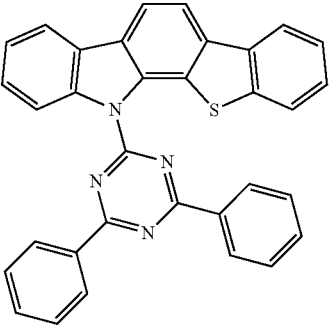 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 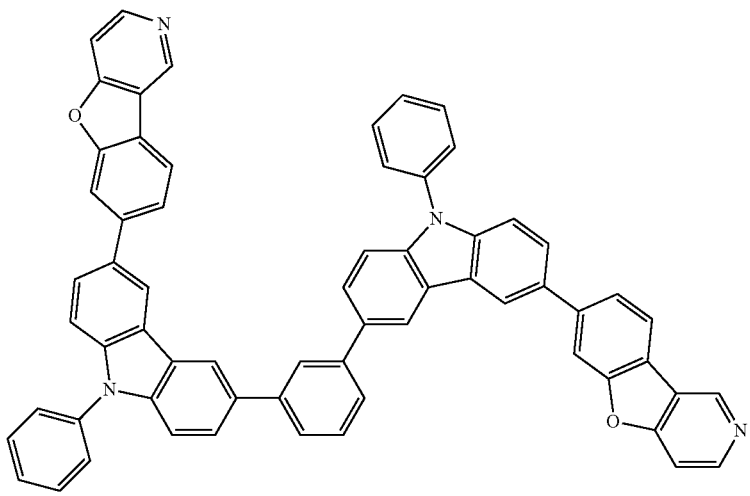 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
|  | 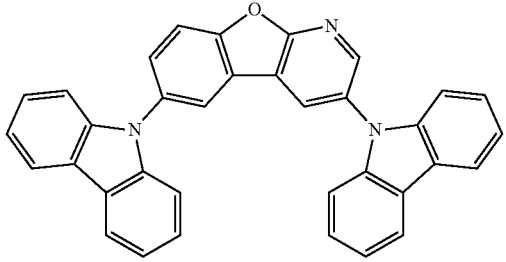 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 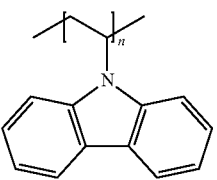 | Appl. Phys. Lett. 77, 2280 (2000) |
| Spirofluorene compounds | 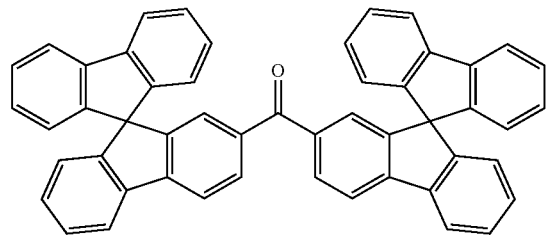 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 2-continued
| MATERIAL | EXAMPLES OF MATERIAL | PUBLICATIONS |
|---|---|---|
| Metal phenoxybenzooxazole compounds | 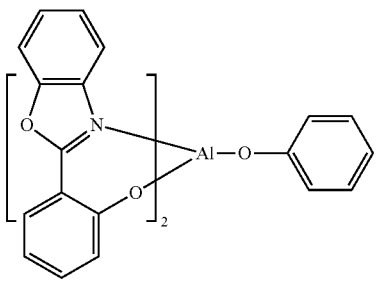 | WO2005089025 |
| | 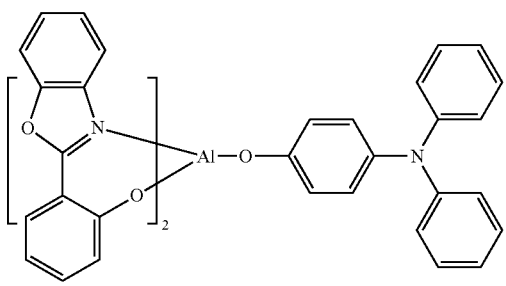 | WO2006132173 |
| | 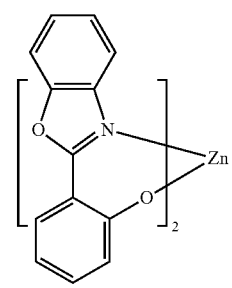 | JP200511610 |
| Spirofluorene-carbazole compounds | 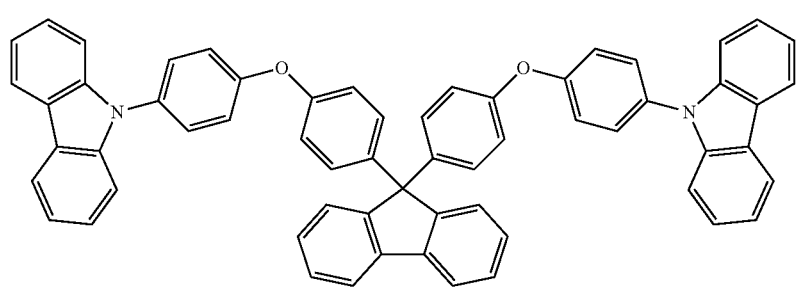 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 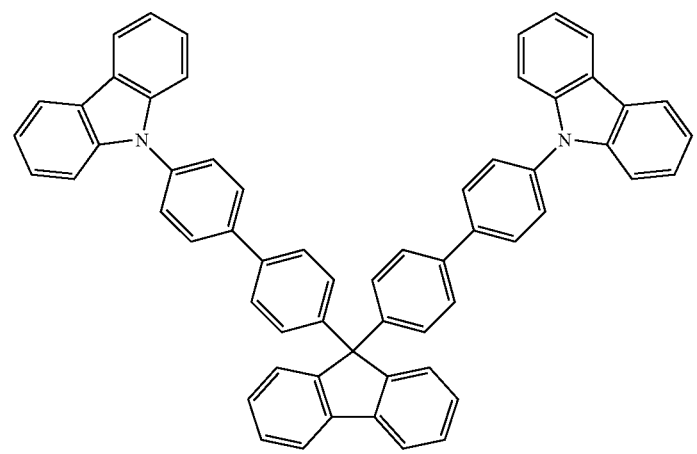 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 2-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 2-continued
| MATERIAL | EXAMPLES OF MATERIAL | PUBLICATIONS |
|---|---|---|
| | 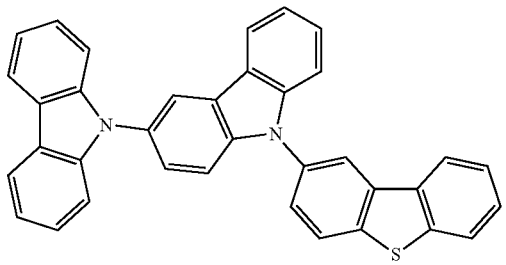 [SMILES: c1ccc2c(c1)sc1ccc(-n3c4ccccc4c4cc(-n5c6ccccc6c6ccccc65)ccc43)cc12] | WO2009086028 |
| | 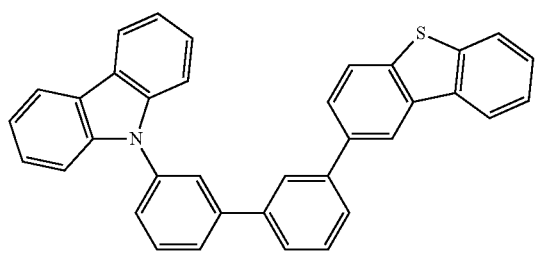 [SMILES: c1cc(-c2cccc(-n3c4ccccc4c4ccccc43)c2)cc(-c2ccc3sc4ccccc4c3c2)c1] | US20090030202, US20090017330 |
| | 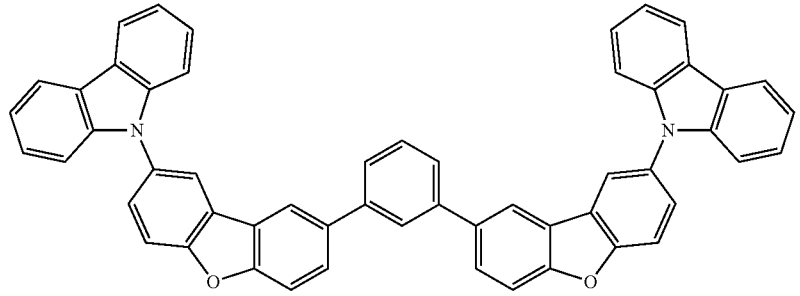 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 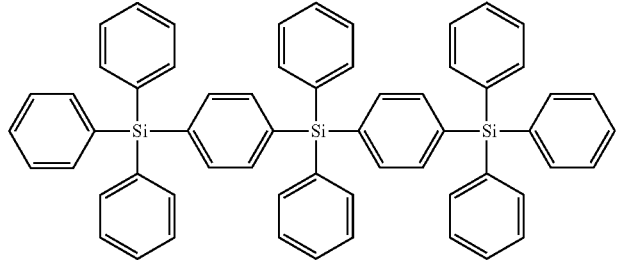 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 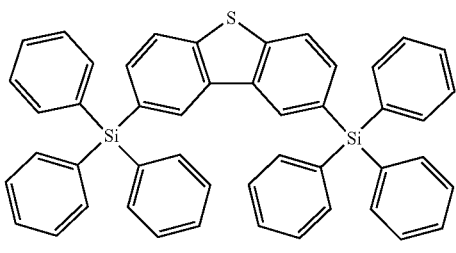 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued
| MATERIAL | EXAMPLES OF MATERIAL | PUBLICATIONS |
|---|---|---|
| Silicon/Germanium aryl compounds | 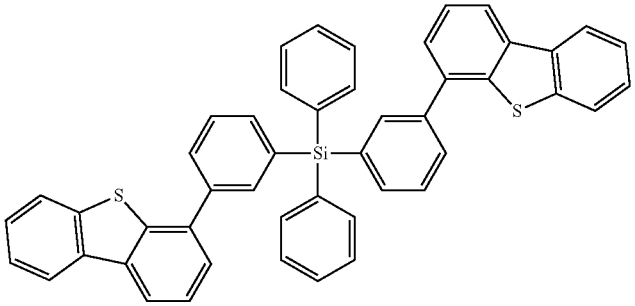 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 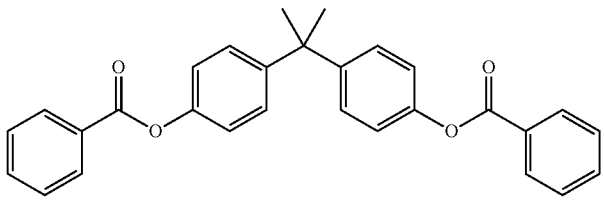 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 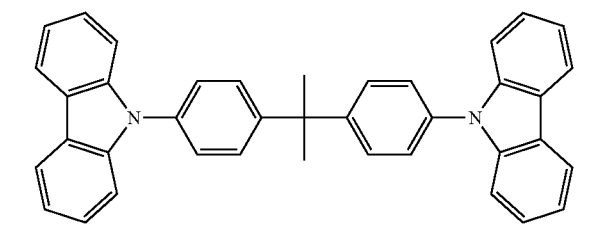 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 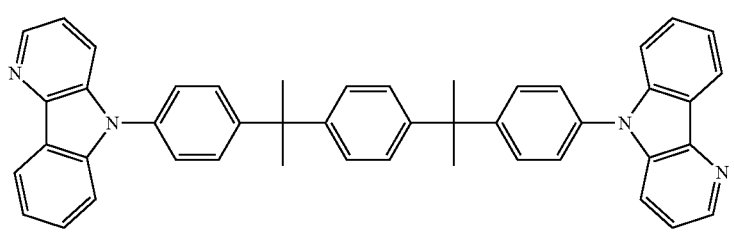 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 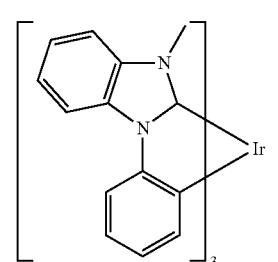 | U.S. Pat. No. 7,154,114 |

TABLE 2-continued

| MATERIAL | EXAMPLES OF MATERIAL | PUBLICATIONS |
| --- | --- | --- |
| | Phosphorescent dopants | |
| | Red dopants | |
| Heavy metal porphyrins (e.g., PtOEP) | | Nature 395, 151 (1998) |
| Iridium (III) organometallic complexes | | Appl. Phys. Lett. 78, 1622 (2001) |
| | | US2006835469 |
| | | US2006835469 |
| | | US20060202194 |

TABLE 2-continued

| MATERIAL | EXAMPLES OF MATERIAL | PUBLICATIONS |
|---|---|---|
|  |  | US20060202194 |
|  |  | US20070087321 |
|  |  | US20080261076<br>US20100090591 |
|  |  | US20070087321 |
|  |  | Adv. Mater. 19, 739 (2007) |

TABLE 2-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum (II) organometallic complexes | | WO2003040257 |
| | | US20070103060 |

TABLE 2-continued

| MATERIAL | EXAMPLES OF MATERIAL | PUBLICATIONS |
| --- | --- | --- |
| Osminum (III) complexes | [structure: F₃C-pyrazole-pyridine with Os(PPhMe₂)₂, subscript 2] | Chem. Mater. 17, 3532 (2005) |
| Ruthenium (II) complexes | [structure: tBu-pyrazole-isoquinoline with Ru(PPhMe₂)₂, subscript 2] | Adv. Mater. 17, 1059 (2005) |
| Rhenium (I), (II), and (III) complexes | [structure: 8-hydroxyquinoline Re—(CO)₄] | US20050244673 |

Green dopants

| | | |
| --- | --- | --- |
| Iridium (III) organometallic complexes | [structure: Ir(ppy)₃] and its derivatives | Inorg. Chem. 40, 1704 (2001) |
| | [structure: Ir(ppy)₂(acac)] | US20020034656 |

TABLE 2-continued
| MATERIAL | EXAMPLES OF MATERIAL | PUBLICATIONS |
|---|---|---|
| | 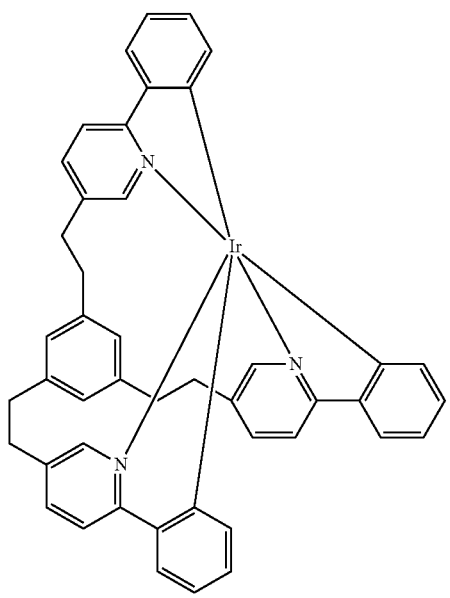 | U.S. Pat. No. 7,332,232 |
| | 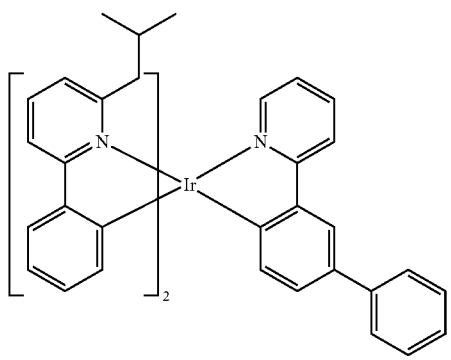 | US20090108737 |
| | 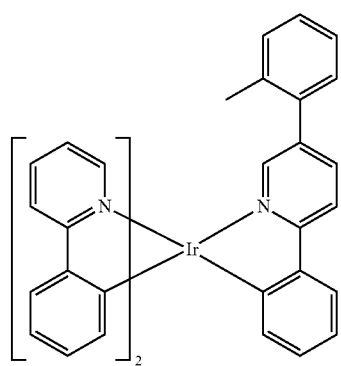 | WO2010028151 |

TABLE 2-continued
| MATERIAL | EXAMPLES OF MATERIAL | PUBLICATIONS |
|---|---|---|
| | 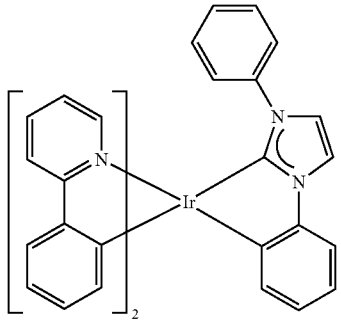 | EP1841834B |
| | 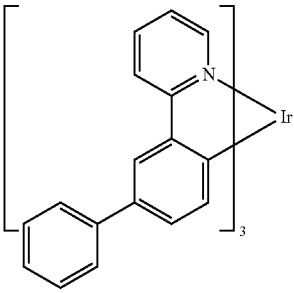 | US20060127696 |
| | 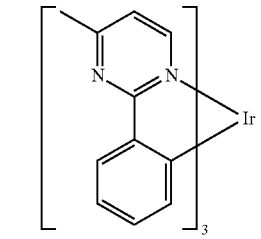 | US20090039776 |
| | 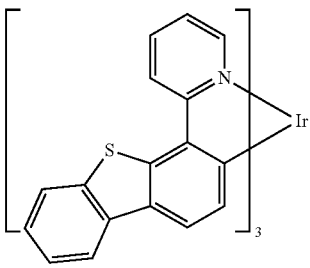 | U.S. Pat. No. 6,921,915 |
| | 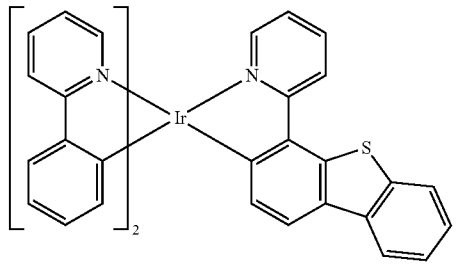 | US20100244004 |

131 132
TABLE 2-continued
| MATERIAL | EXAMPLES OF MATERIAL | PUBLICATIONS |
|---|---|---|
| | 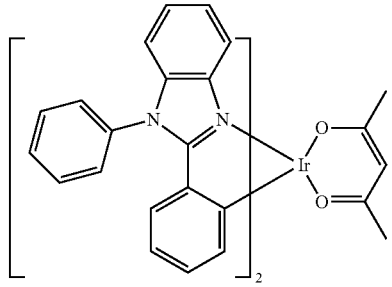 | U.S. Pat. No. 6,687,266 |
| | 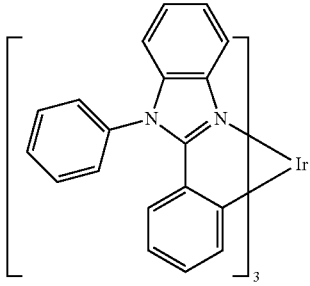 | Chem. Mater. 16, 2480 (2004) |
| | 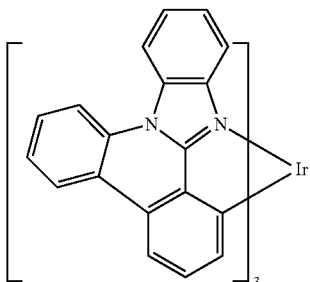 | US20070190359 |
| | 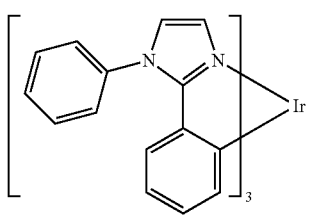 | US 20060008670 JP2007123392 |
| | 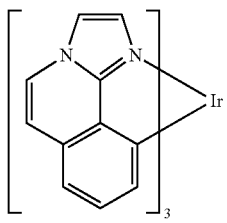 | WO2010086089, WO2011044988 |
| | 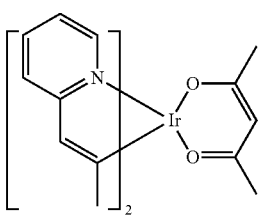 | Adv. Mater. 16, 2003 (2004) |

TABLE 2-continued
| MATERIAL | EXAMPLES OF MATERIAL | PUBLICATIONS |
|---|---|---|
| | 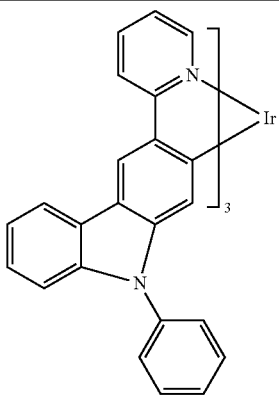 | Angew. Chem. Int. Ed. 2006, 45, 7800 |
| | 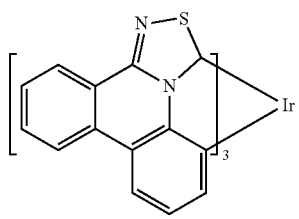 | WO2009050290 |
| | 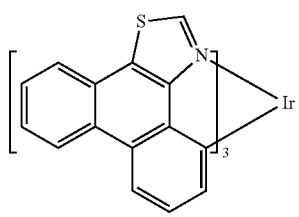 | US20090165846 |
| | 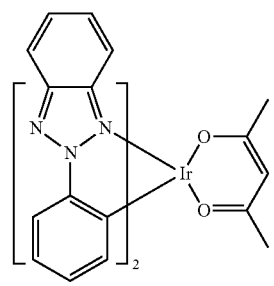 | US20080015355 |
| | 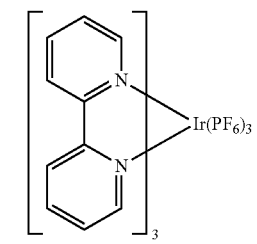 | US20010015432 |
| | 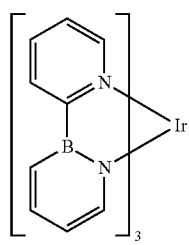 | US20100295032 |

TABLE 2-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt (II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 2-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 2-continued
| MATERIAL | EXAMPLES OF MATERIAL | PUBLICATIONS |
|---|---|---|
| Gold complexes | 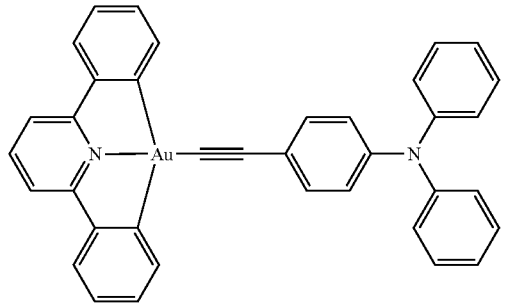 | Chem. Commun. 2906 (2005) |
| Rhenium (III) complexes | 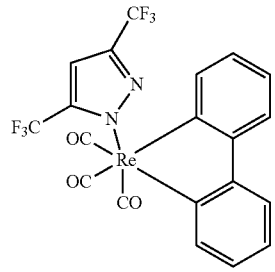 | Inorg. Chem. 42, 1248 (2003) |
| Osmium (II) complexes | 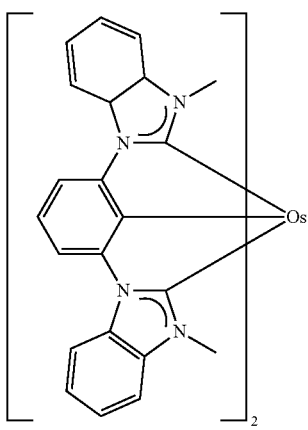 | U.S. Pat. No. 7,279,704 |
| Deuterated organometallic complexes | 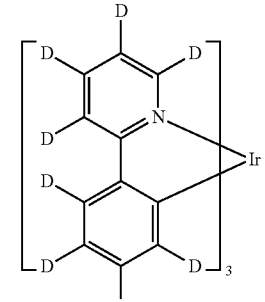 | US20030138657 |

| MATERIAL | EXAMPLES OF MATERIAL | PUBLICATIONS |
|---|---|---|
| Organometallic complexes with two or more metal centers | 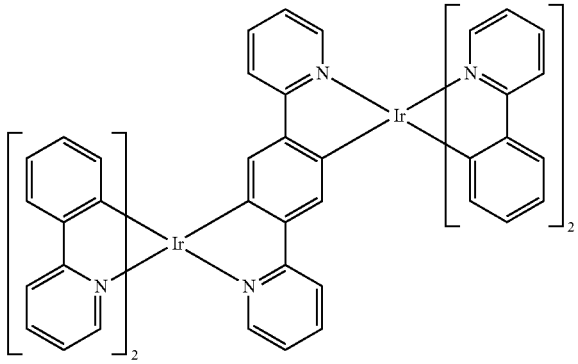 | US20030152802 |
| | 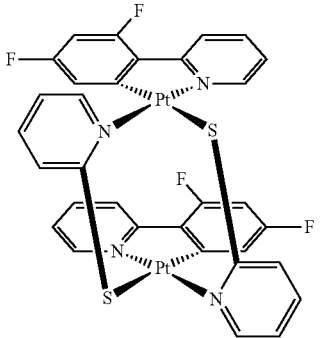 | U.S. Pat. No. 7,090,928 |
| Blue dopants | | |
| Iridium (III) organometallic complexes | 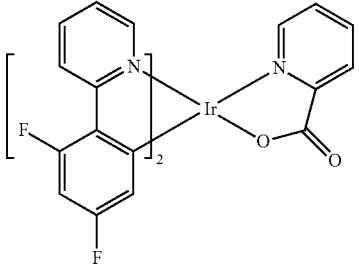 | WO2002002714 |
| | 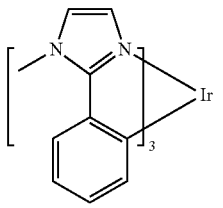 | WO2006009024 |
| | 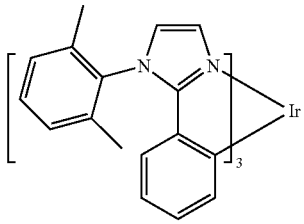 | US20060251923<br>US20110057559<br>US20110204333 |

TABLE 2-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 2-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE 2-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium (II) complexes | | U.S. Pat. No. 7,279,704 |

TABLE 2-continued

| MATERIAL | EXAMPLES OF MATERIAL | PUBLICATIONS |
|---|---|---|
| | 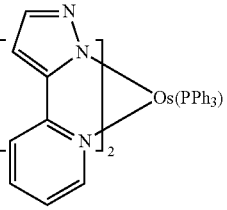 | Organometallics 23, 3745 (2004) |
| Gold complexes | 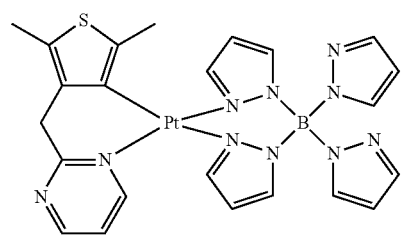 | Appl. Phys. Lett. 74, 1361 (1999) |
| Platinum (II) complexes | | WO2006098120, WO2006103874 |
| Pt tetradentate complexes with at least one metal-carbene bond | 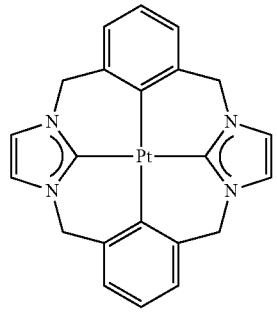 | U.S. Pat. No. 7,655,323 |
| Exciton/hole blocking layer materials | | |
| Bathocuprine compounds (e.g., BCP, BPhen) | 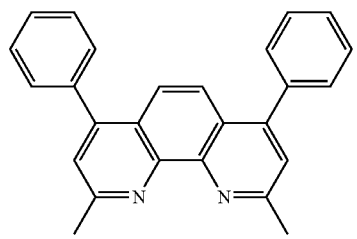 [SMILES: Cc1cc(-c2ccccc2)c2ccc3c(-c4ccccc4)cc(C)nc3c2n1] | Appl. Phys. Lett. 75, 4 (1999) |
| | | Appl. Phys. Lett. 79, 449 (2001) |
| Metal 8-hydroxyquinolates (e.g., BAlq) | 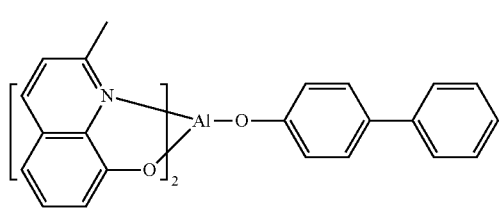 | Appl. Phys. Lett. 81, 162 (2002) |

TABLE 2-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 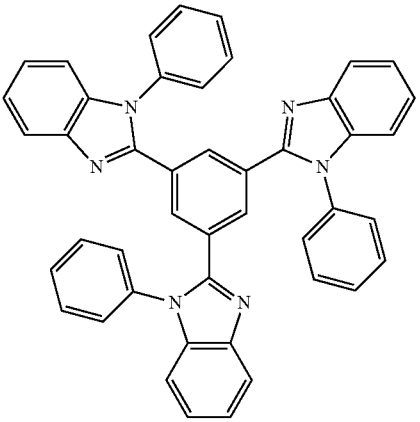 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 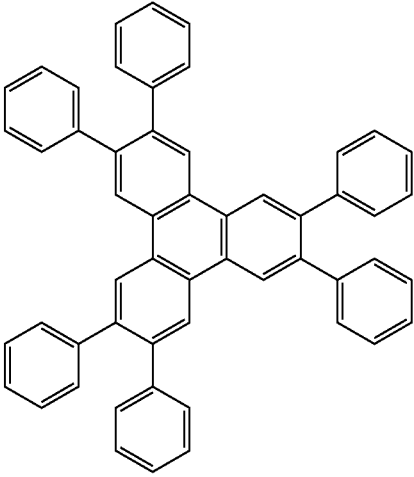 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 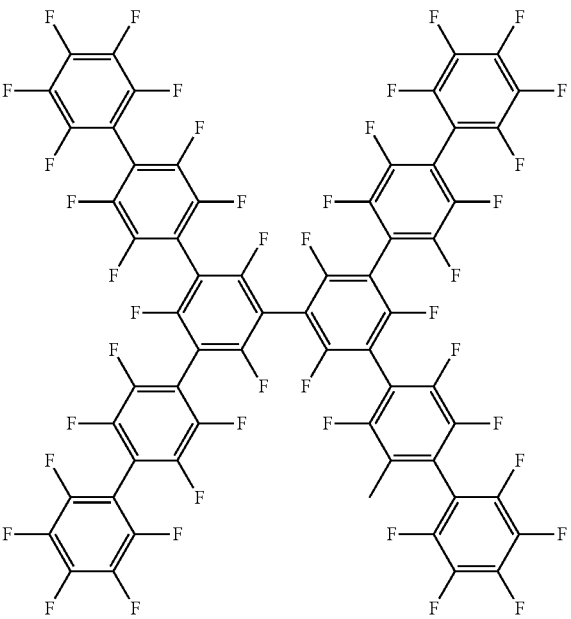 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 2-continued
| MATERIAL | EXAMPLES OF MATERIAL | PUBLICATIONS |
|---|---|---|
| Phenothiazine-S-oxide | 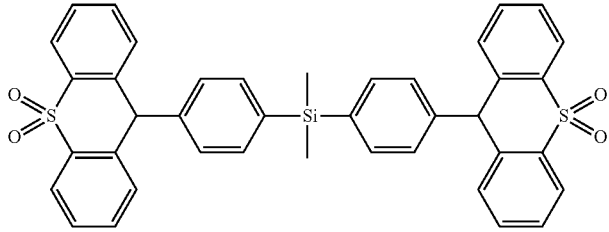 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 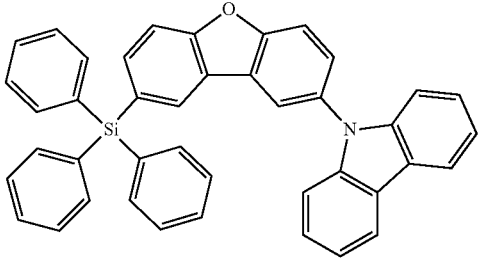 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 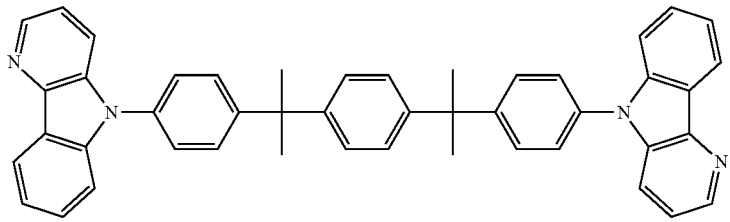 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials
| | | |
|---|---|---|
| Anthracene-benzoimidazole compounds | 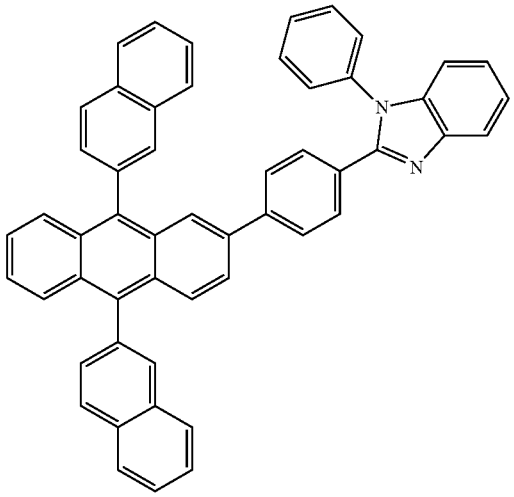 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 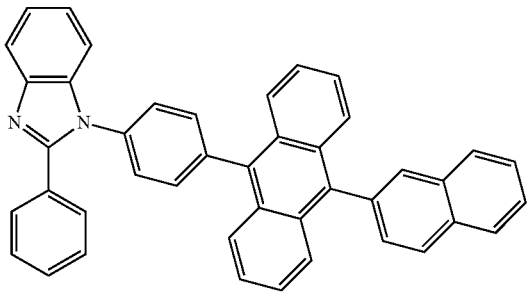 [SMILES: c1ccc(-c2nc3ccccc3n2-c2ccc(-c3c4ccccc4c(-c4ccc5ccccc5c4)c4ccccc34)cc2)cc1] | US20090179554 |

TABLE 2-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987) <br> U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 2-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 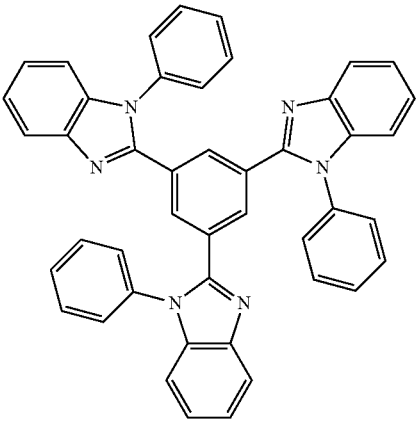 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 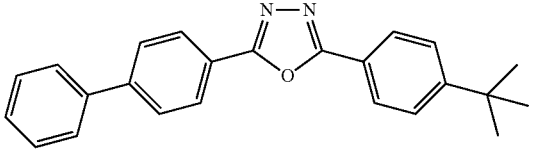 [SMILES: CC(C)(C)c1ccc(-c2nnc(-c3ccc(-c4ccccc4)cc3)o2)cc1] | Appl. Phys. Lett. 55, 1489 (1989) |
| | 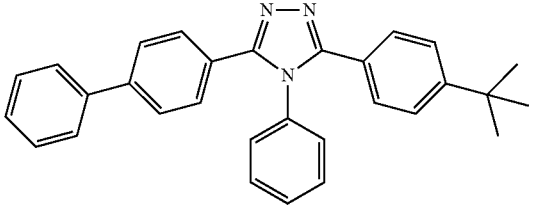 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 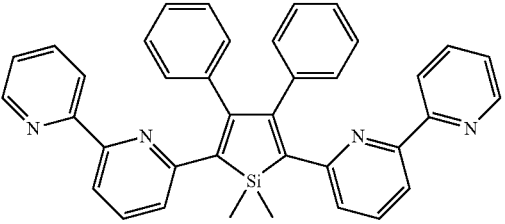 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 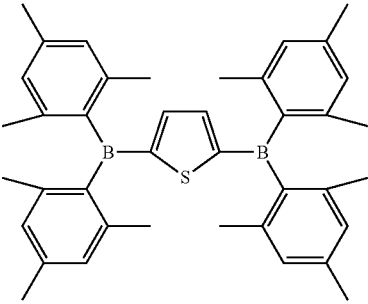 | J. Am. Chem. Soc. 120, 9714 (1998) |
| Fluorinated aromatic compounds | 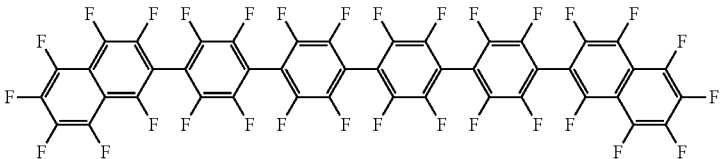 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

| MATERIAL | EXAMPLES OF MATERIAL | PUBLICATIONS |
| --- | --- | --- |
| Fullerene (e.g., C60) | 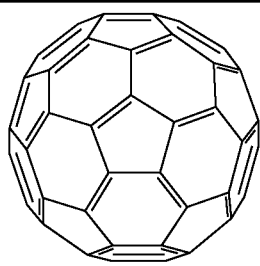 | US20090101890 |
| Triazine complexes | 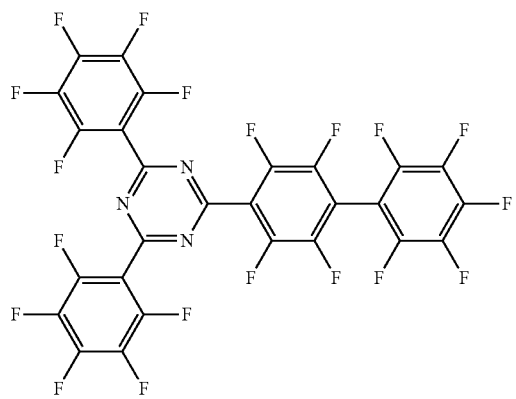 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 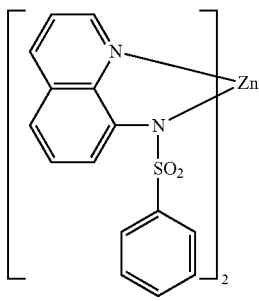 | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having a structure comprising formula (I):

A-L-B     (I), wherein A is selected from the group consisting of

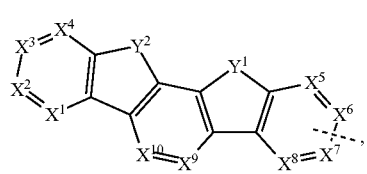

-continued

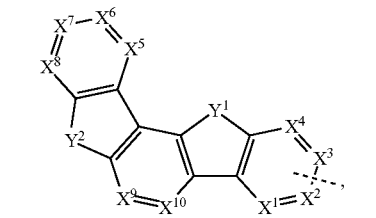

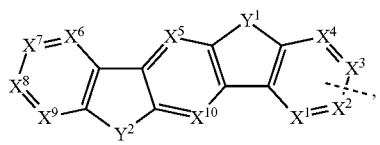

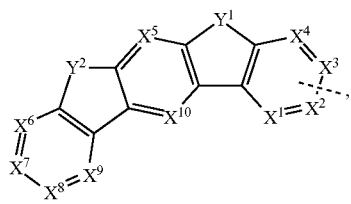

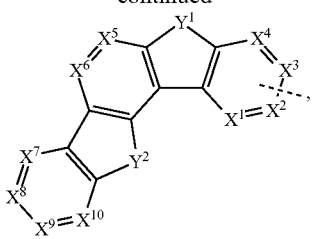

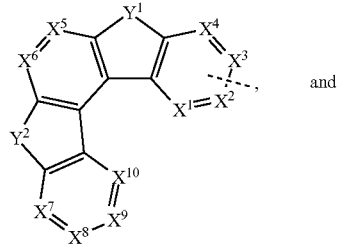
and

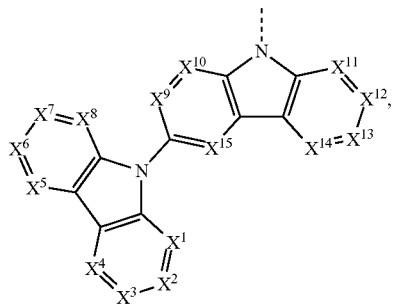

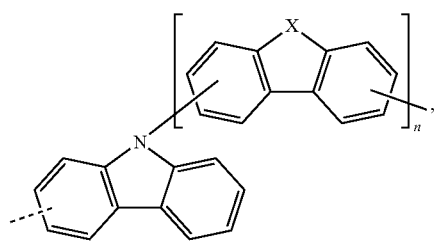

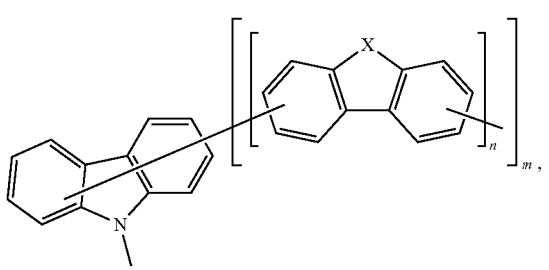

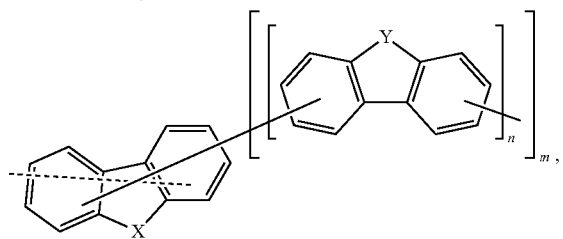

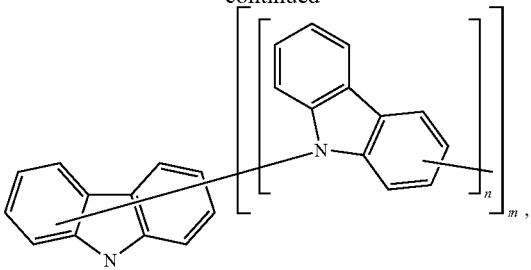

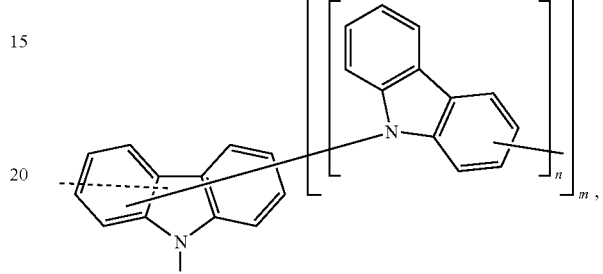

and

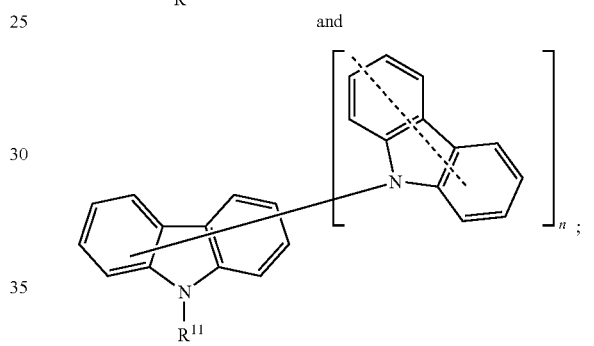

wherein
n is an integer from 1 to 20,
m is an integer from 1 to 20,
X and Y are independently selected from the group consisting of O, S, and $NR^{14}$,
$R^{11}$ and $R^{14}$ are selected from the group consisting of aryl and heteroaryl,
$X^1$-$X^{15}$ are independently selected from the group consisting of N and C—R",
R" is selected from a group consisting of hydrogen, deuterium, alkyl, cycloalkyl, arylalkyl, alkoxy, aryloxy, amino, silyl, aryl, heteroaryl, and combinations thereof; and
$Y^1$ and $Y^2$ are independently selected from the group consisting of O, S, and Se;
wherein L is an aryl or heteroaryl group having from 5-30 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof; and
wherein B is an all-benzenoid group having at least 24 carbon atoms, which are optionally further substituted with one or more groups selected from hydrogen, deuterium, alkyl, cycloalkyl, arylalkyl, alkoxy, aryloxy, amino, silyl, aryl, and combinations thereof.

2. The compound of claim 1, wherein L is selected from the group consisting of:

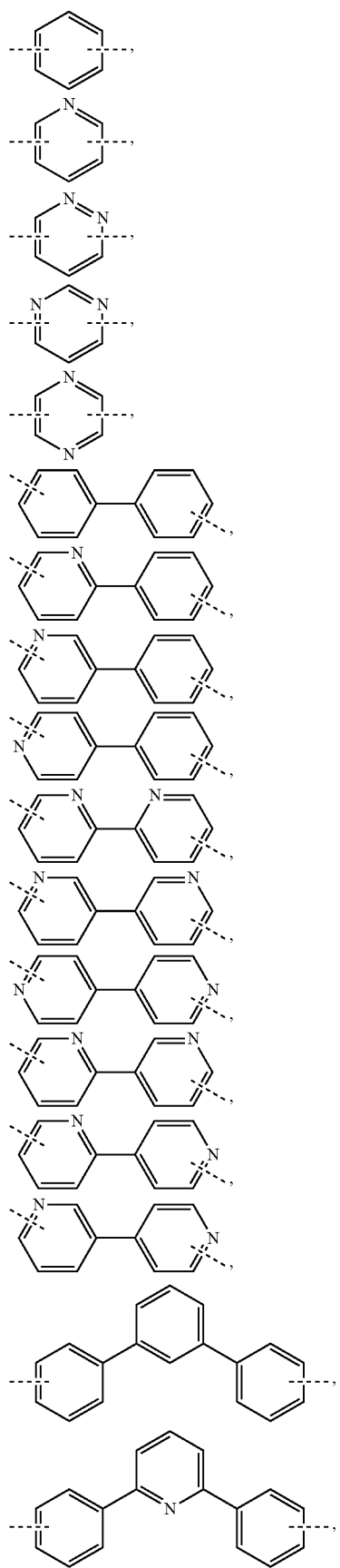
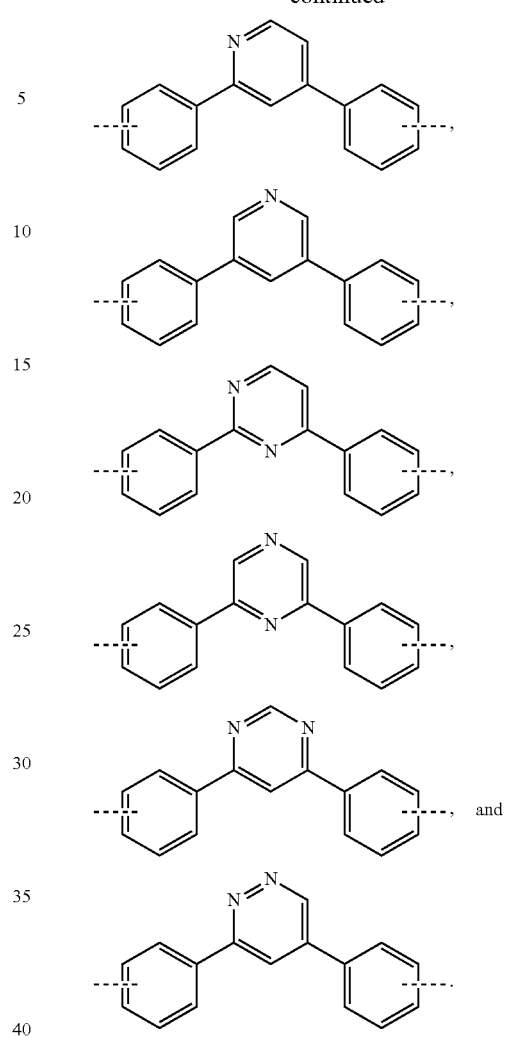
, and
3. The compound of claim 1, wherein A is selected from the group consisting of:
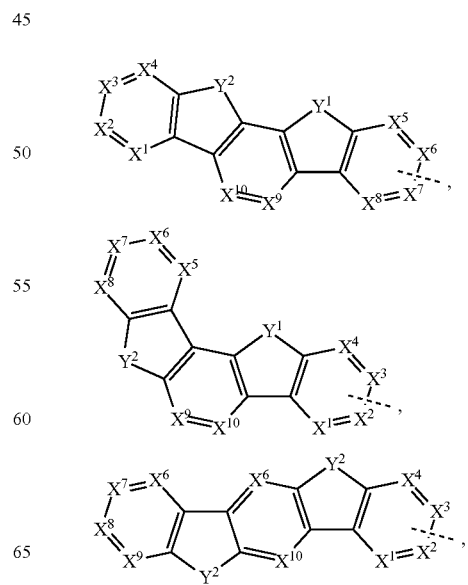

-continued
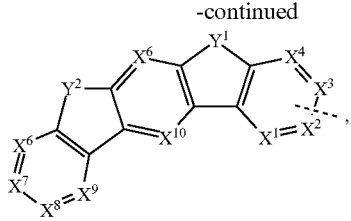
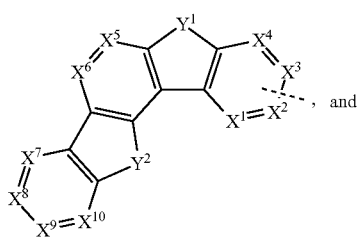
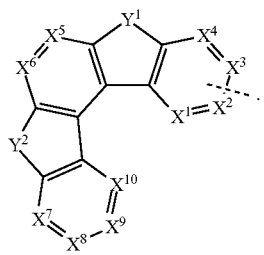
4. The compound of claim 1, wherein A is selected from the group consisting of:
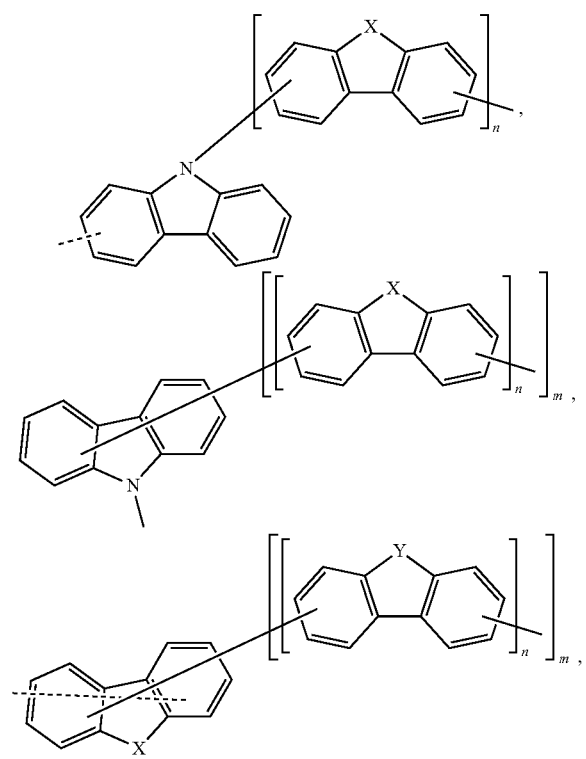
-continued
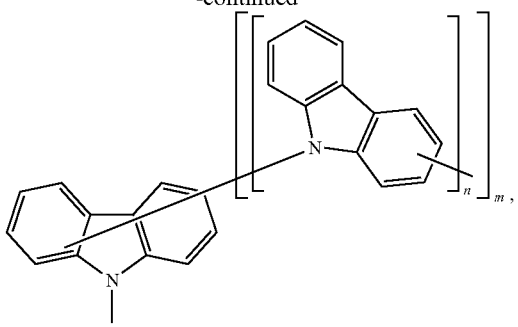
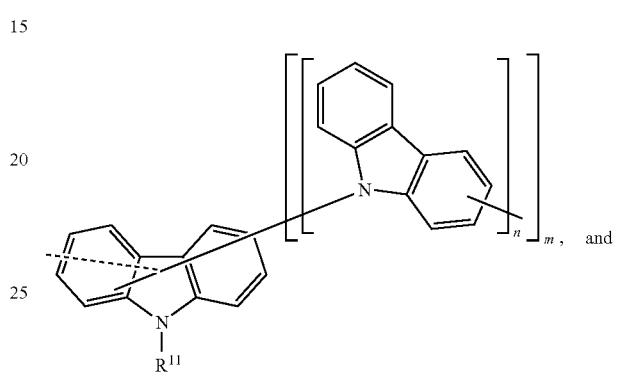
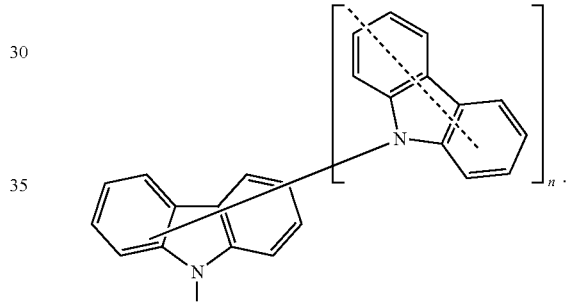
5. The compound of claim 1, wherein B is selected from the group consisting of:
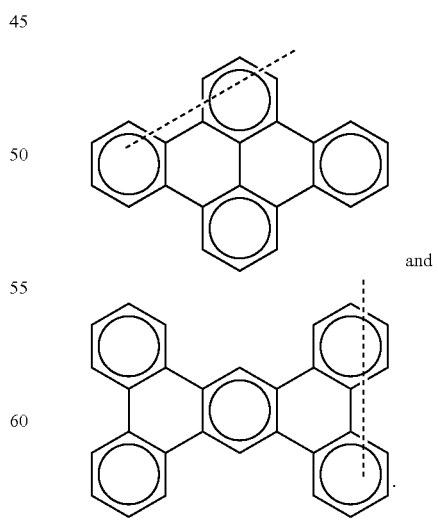
6. The compound of claim 1, wherein A is selected from the group consisting of:

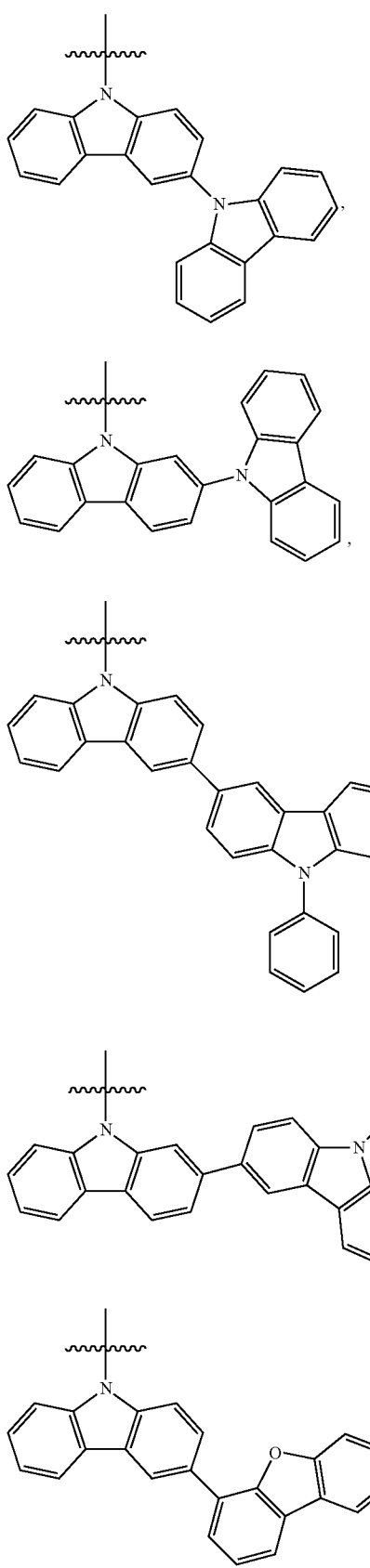
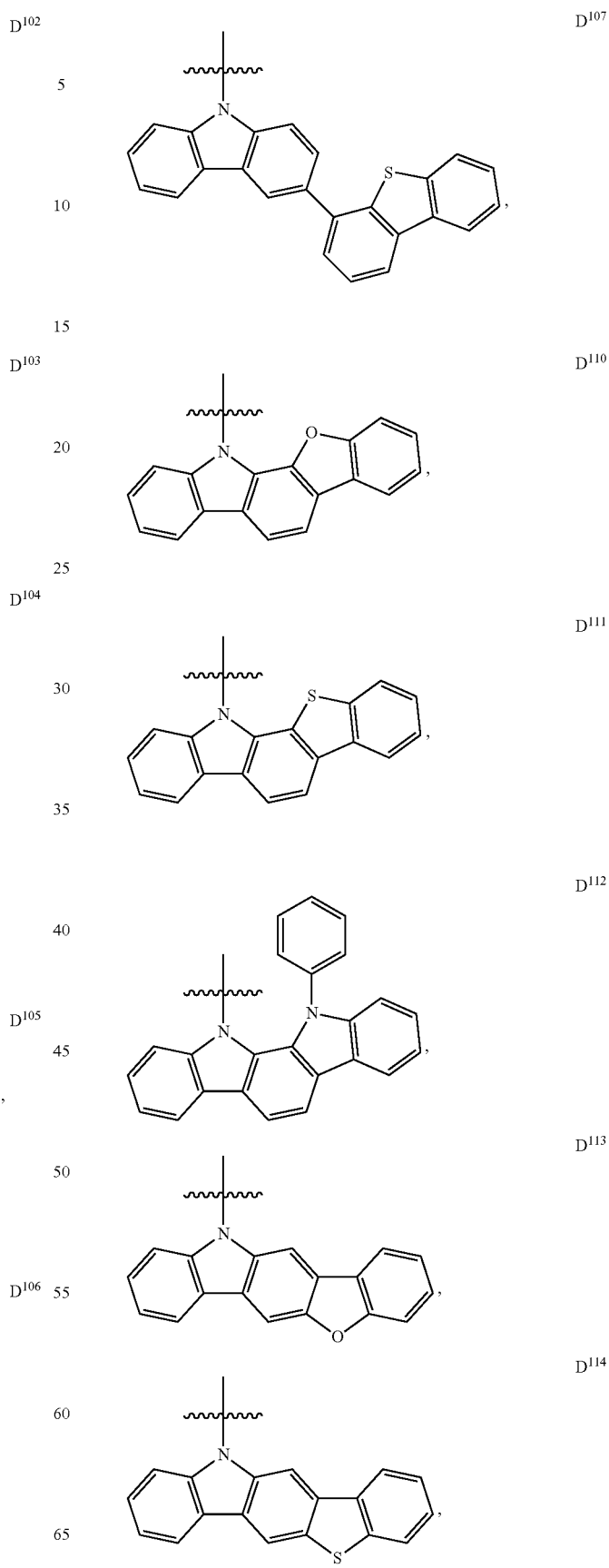

-continued
D115
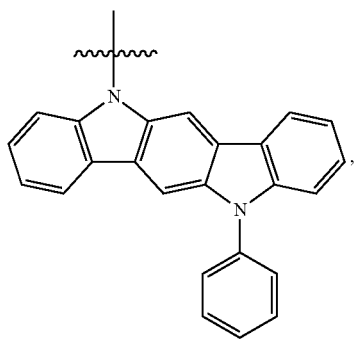,
D116
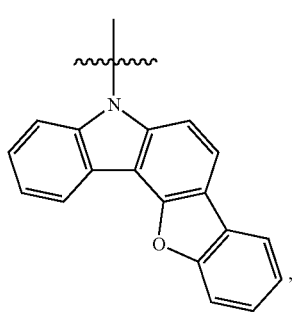,
D117
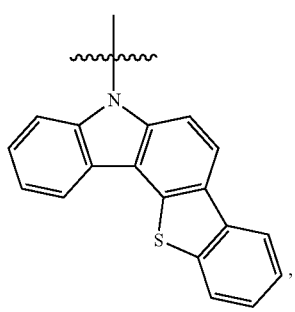,
D118
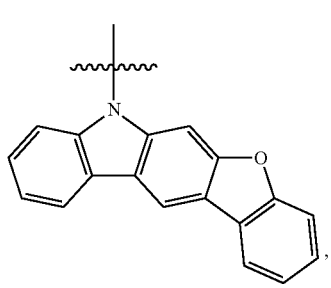,
D119
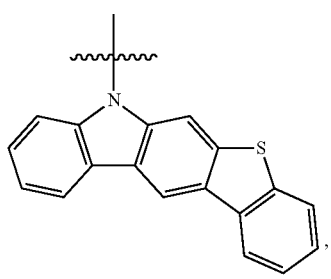,
-continued
D120
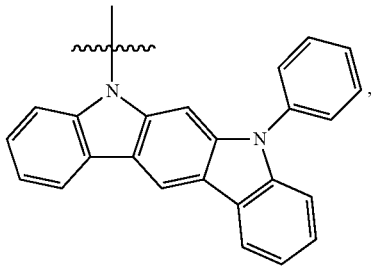,
D141
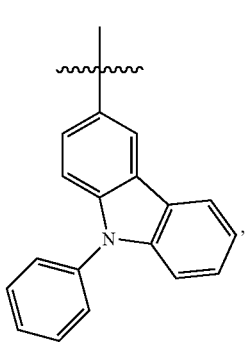,
D142
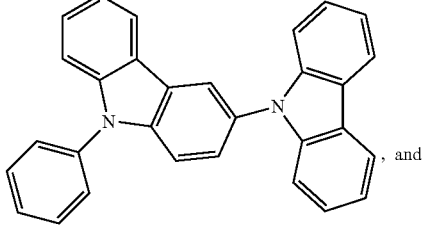, and
D144
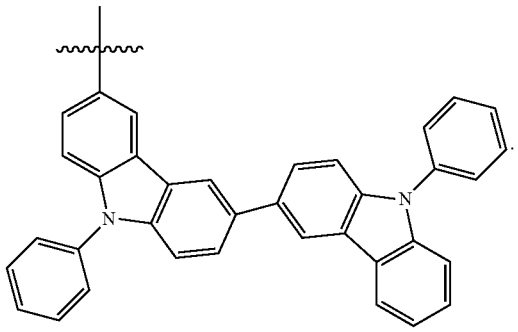, 7. A compound selected from the group consisting of:
Compound 14
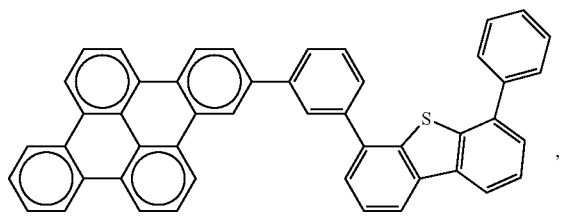
Compound 16
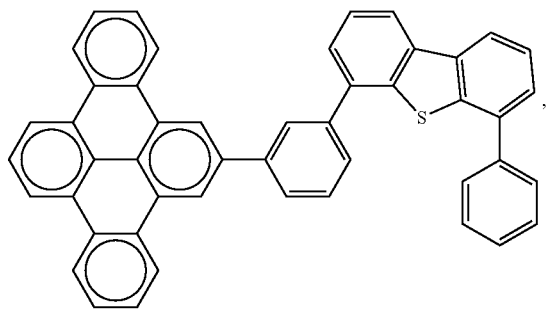
Compound 18
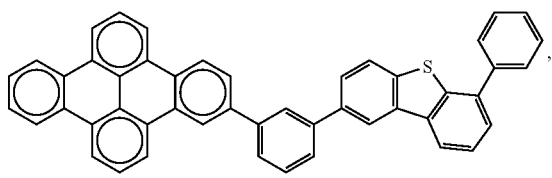
Compound 20
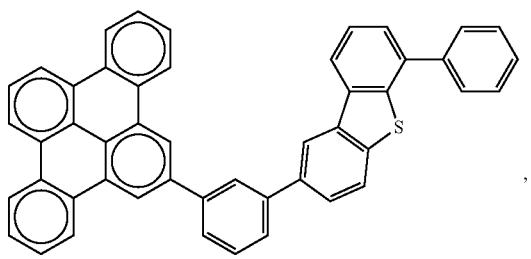
Compound 22
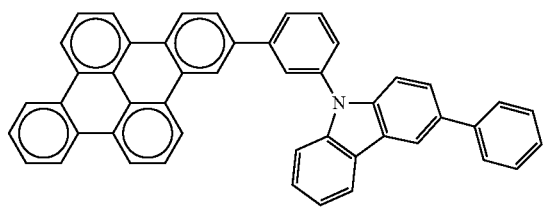

-continued
Compound 24
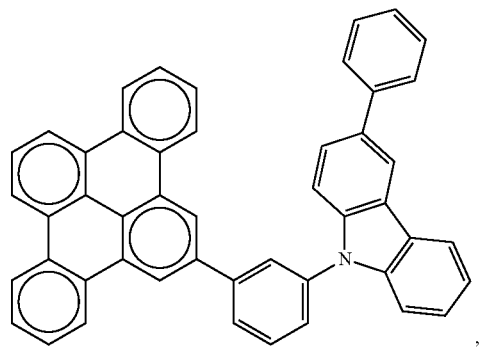
Compound 26
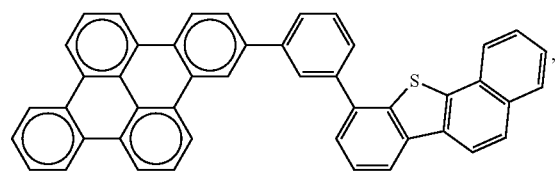
Compound 28
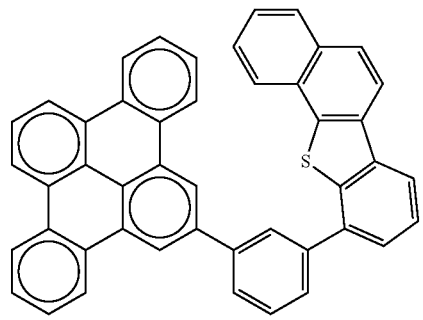
Compound 30
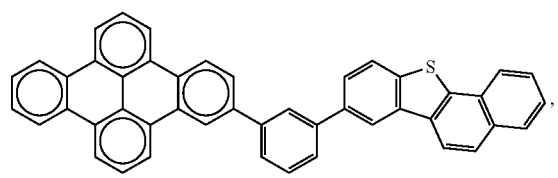
Compound 32
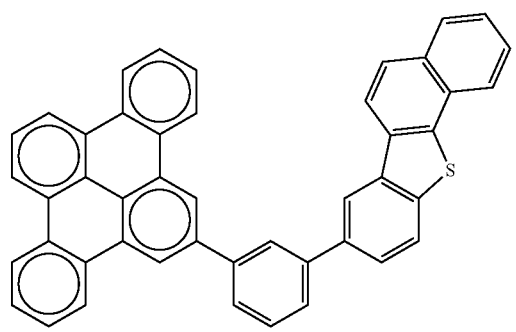

-continued
Compound 34
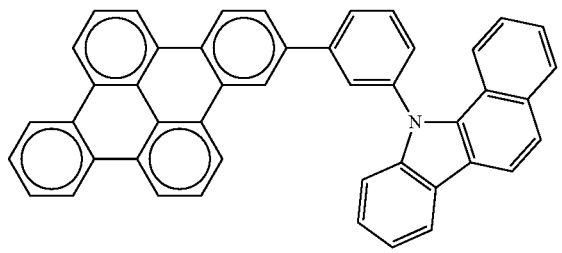
Compound 36
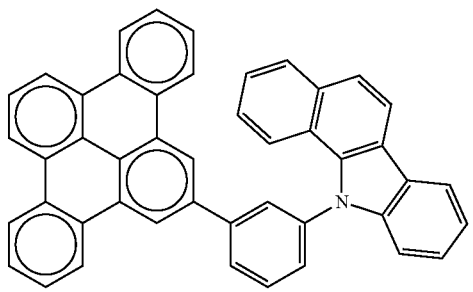
Compound 38
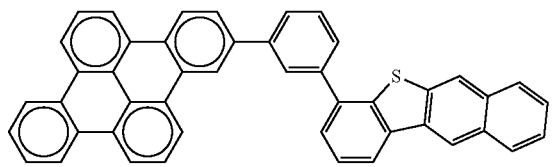
Compound 40
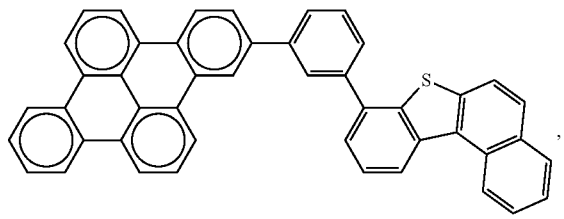
Compound 48
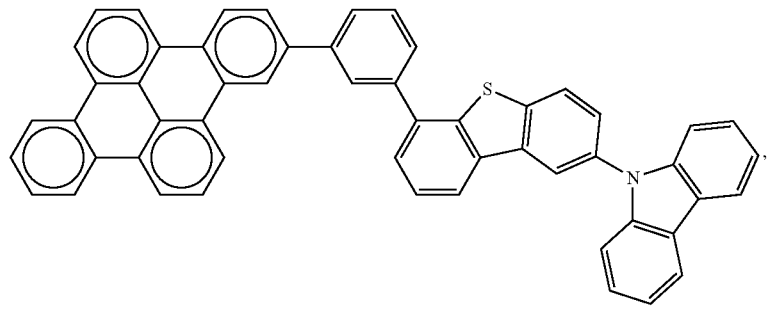

-continued
Compound 49
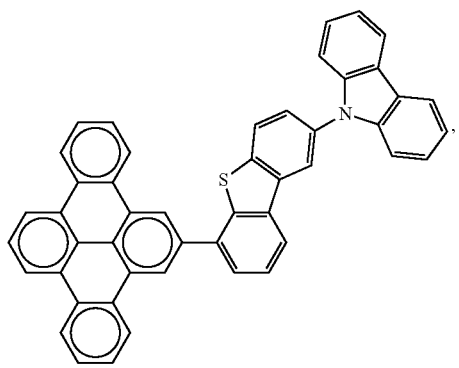
Compound 50
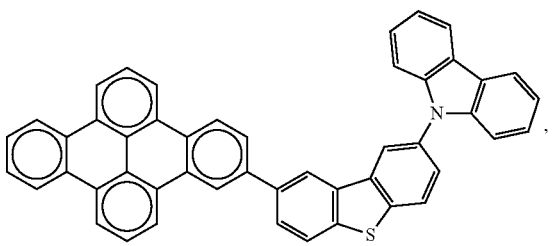
Compound 51
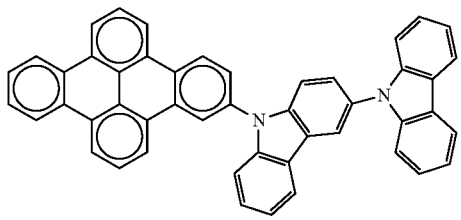
Compound 52
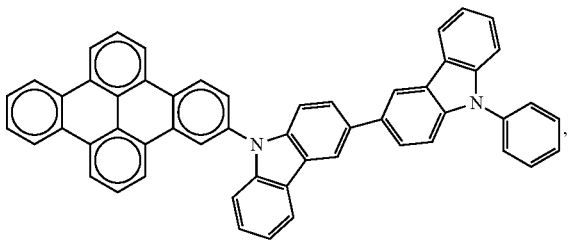
Compound 53
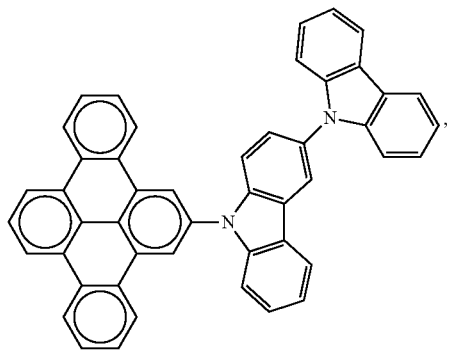
Compound 54
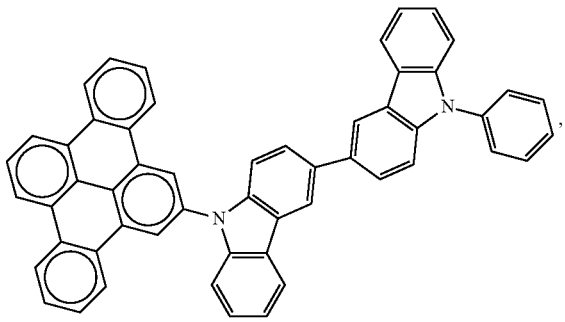
Compound 69
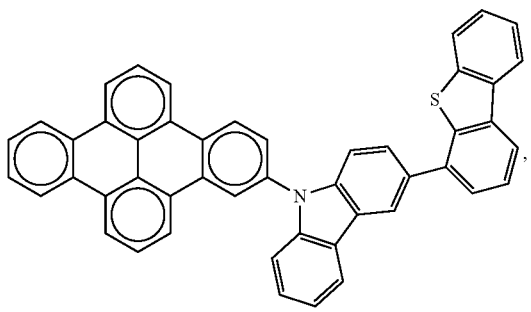
Compound 70
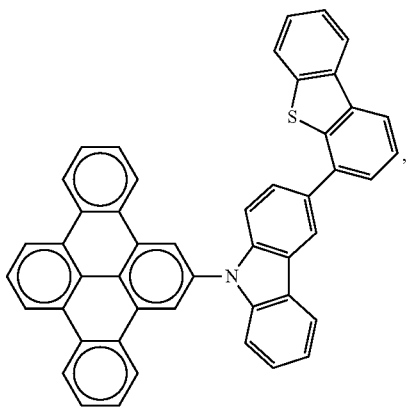

-continued
Compound 72
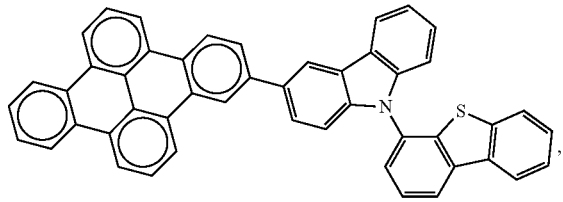
Compound 73
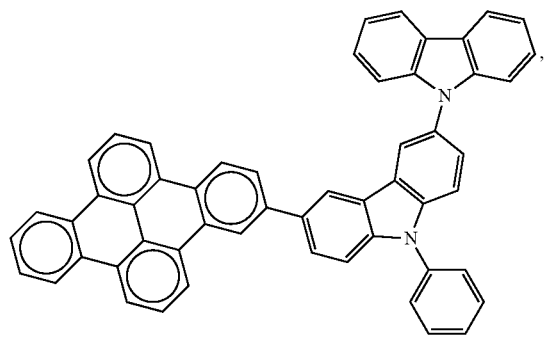
Compound 76
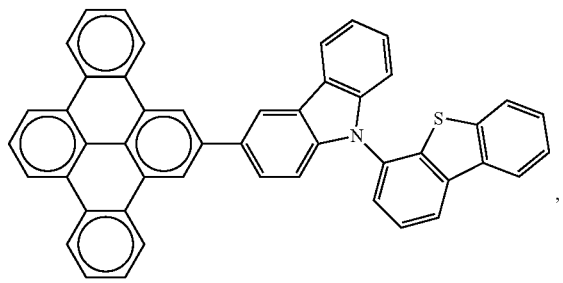
Compound 87
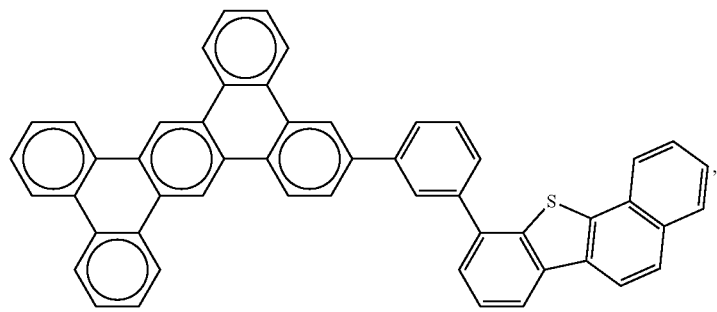
Compound 89
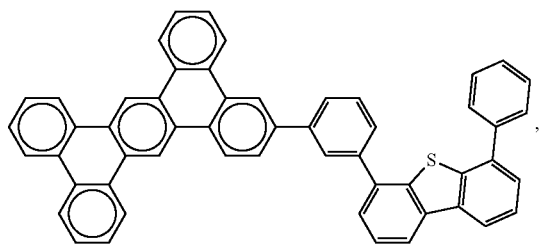

-continued
Compound 90
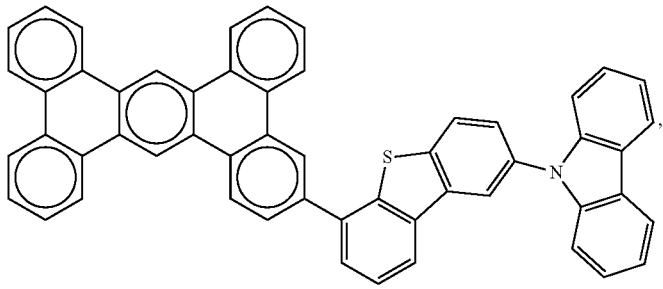
Compound 91
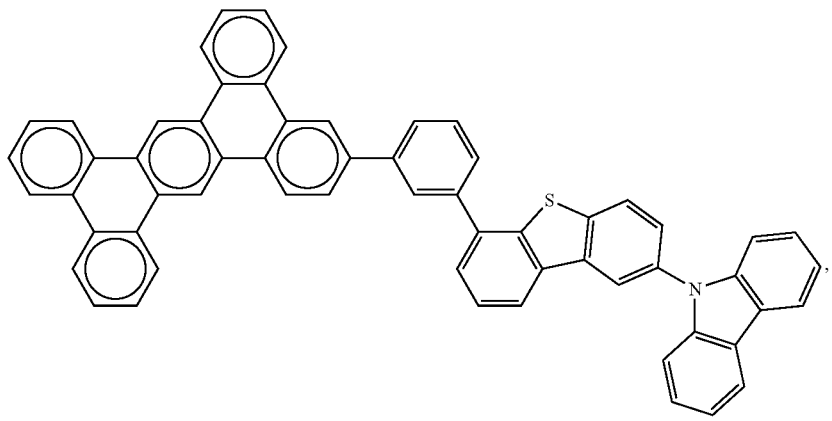
Compound 94
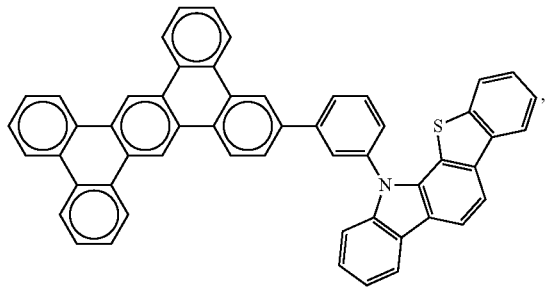
Compound 104
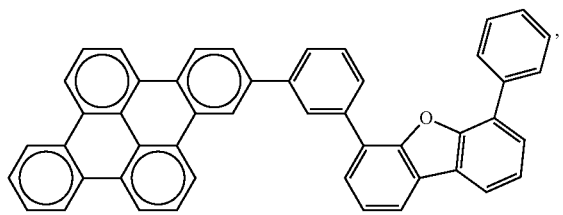
Compound 106
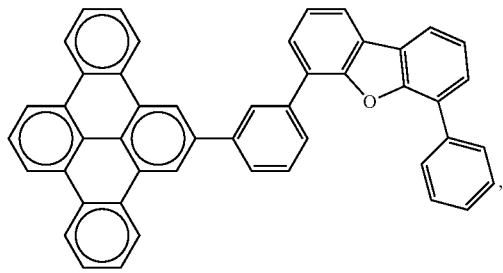

-continued
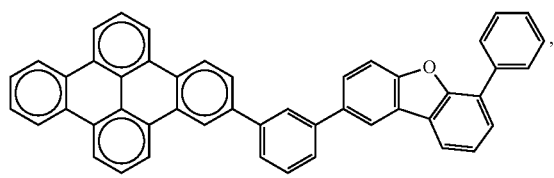
Compound 108
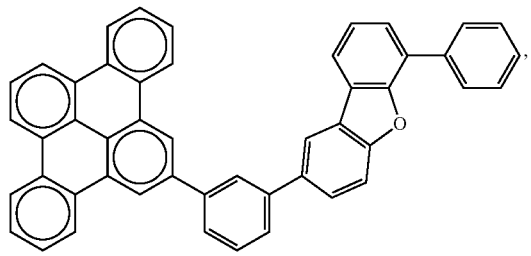
Compound 110
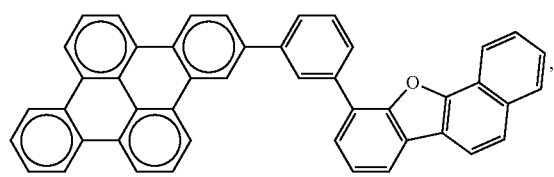
Compound 112
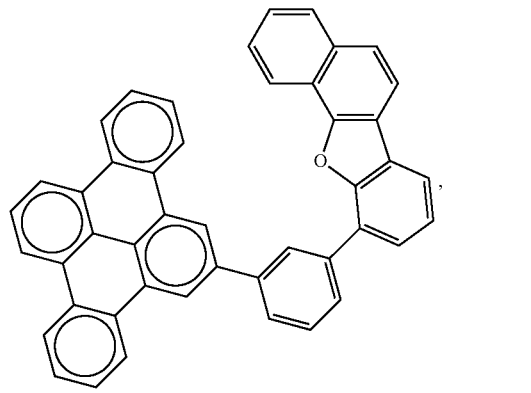
Compound 114
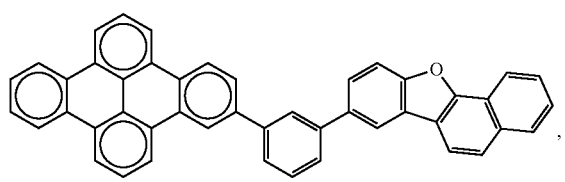
Compound 116
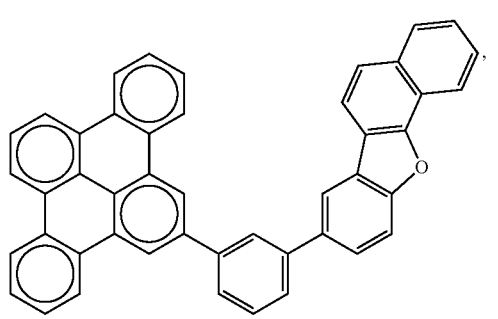
Compound 118

-continued
Compound 120
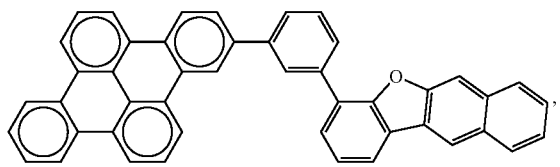
Compound 122
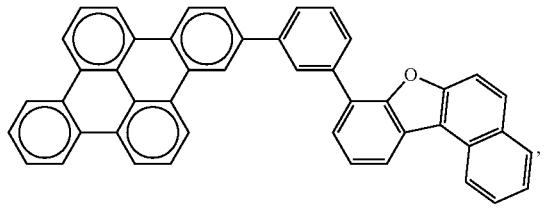
Compound 127
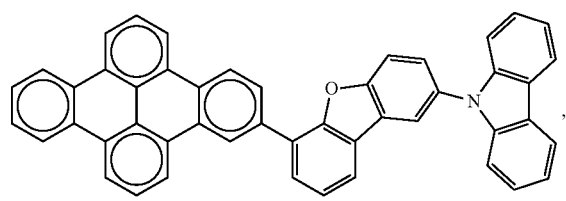
Compound 128
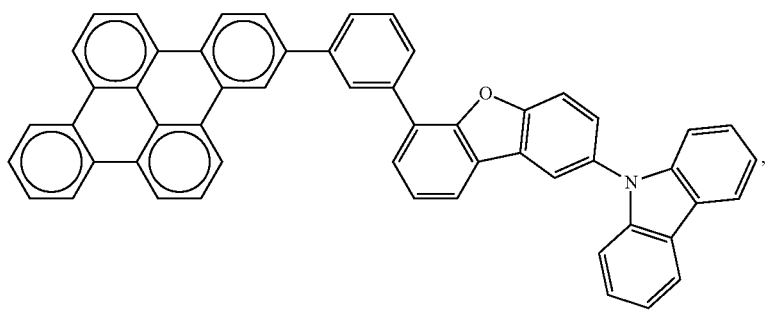
Compound 129
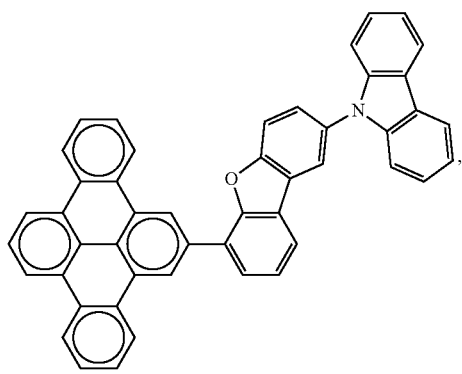
Compound 130
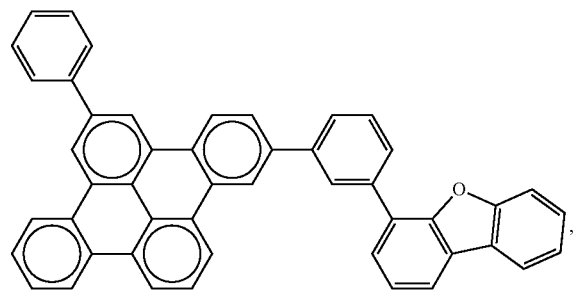
Compound 138

-continued
Compound 141
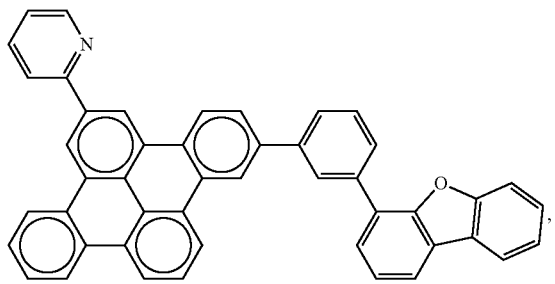
Compound 143
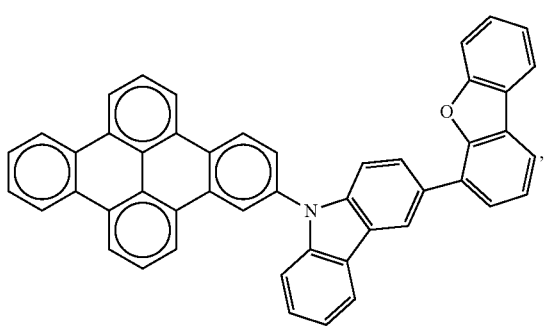
Compound 144
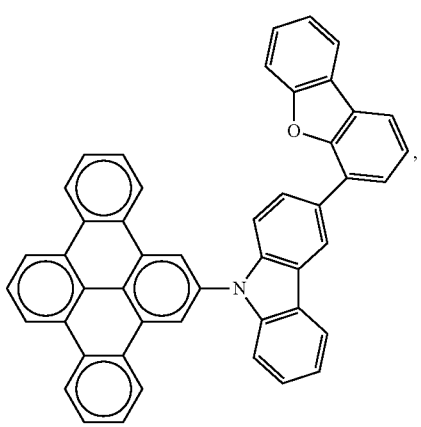
Compound 145
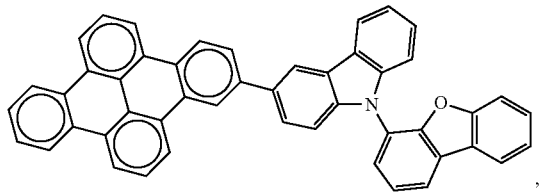
Compound 147
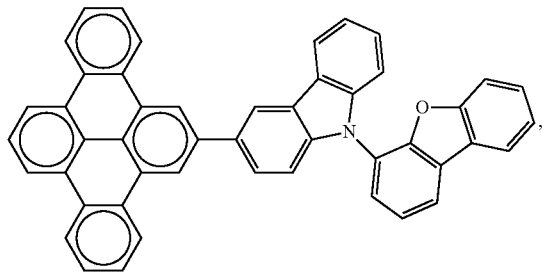
Compound 156
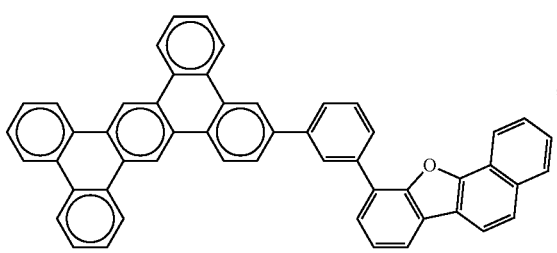

-continued

Compound 158

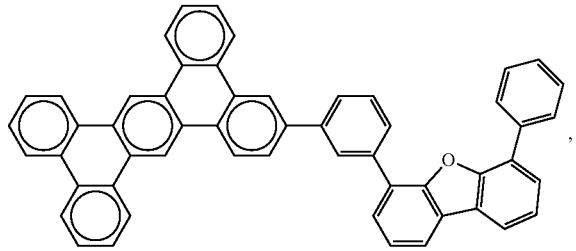

Compound 159

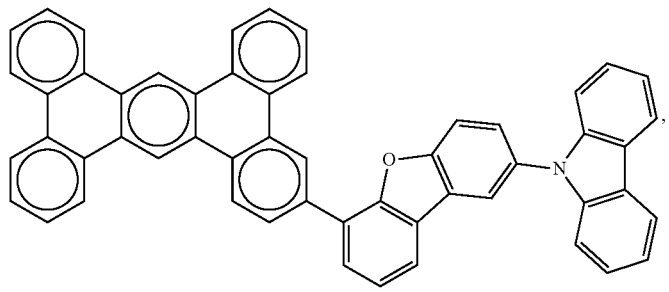

Compound 160

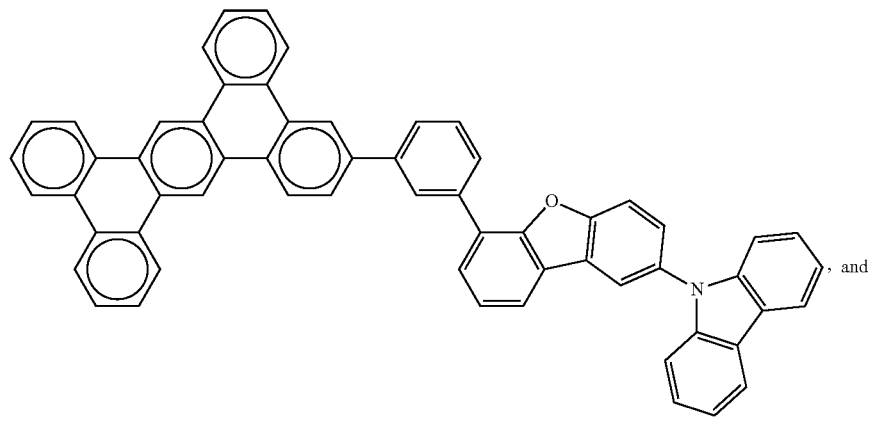, and

Compound 163

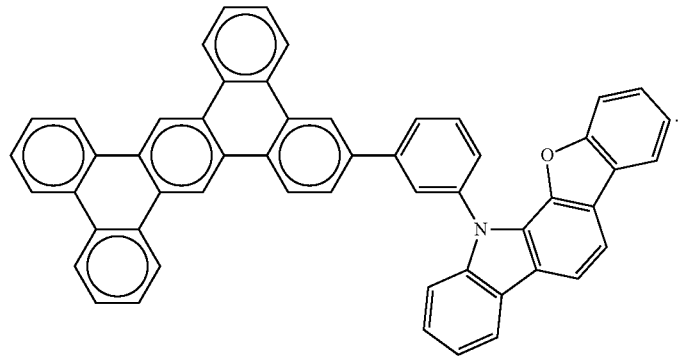.

8. A first device comprising a phosphorescent organic light-emitting device, the phosphorescent organic light-emitting device comprising:
 an anode;
 a cathode; and
 an organic layer, disposed between the anode and the cathode, comprising a compound having a formula I:

A-L-B  (I), wherein A is selected from the group consisting of

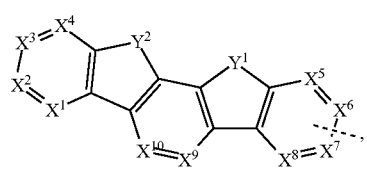

191
-continued
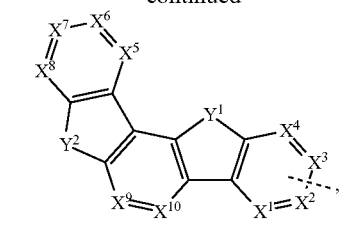
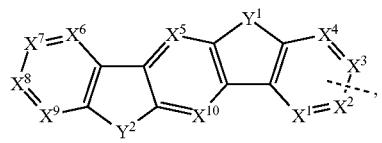
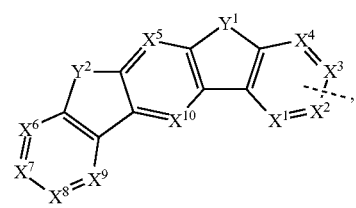
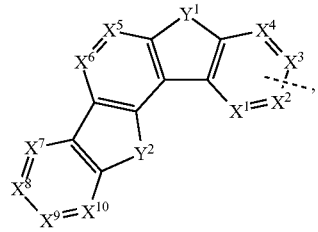
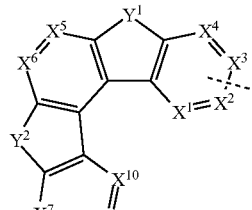
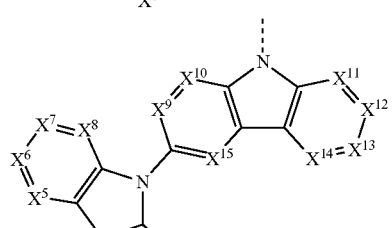
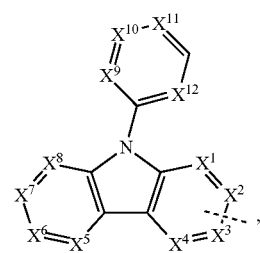
192
-continued
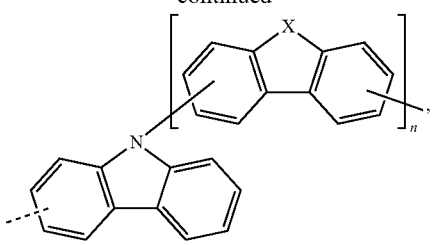
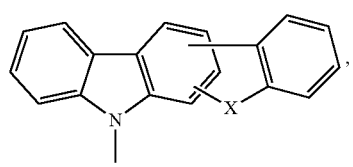
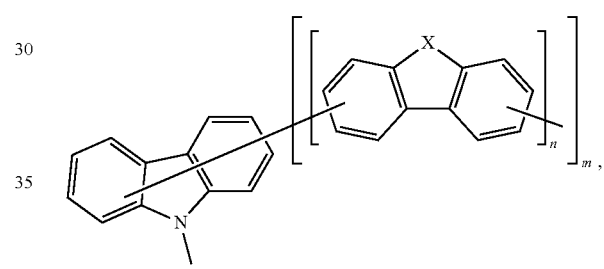
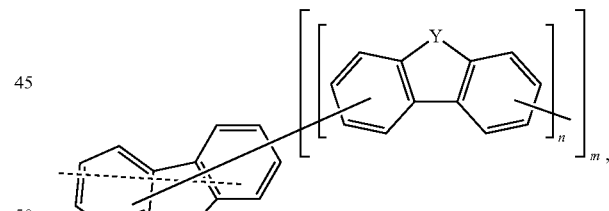
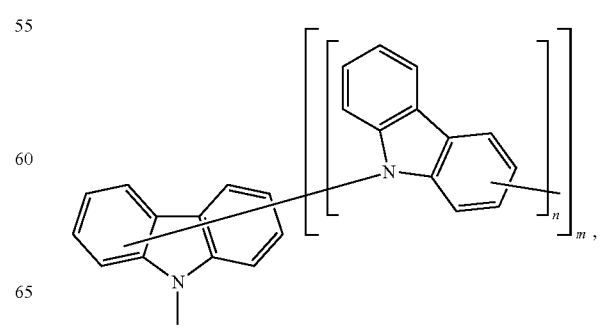

-continued

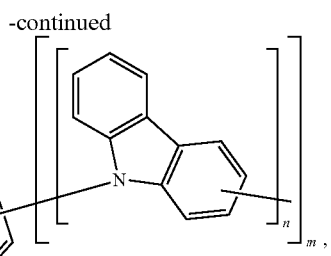

and

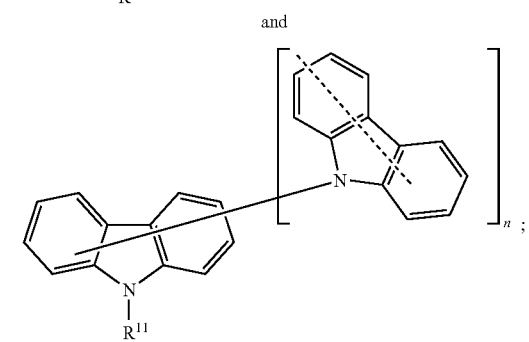

wherein $X^1$-$X^{15}$ are C—R", wherein R" is selected from a group consisting of hydrogen, deuterium, alkyl, cycloalkyl, arylalkyl, alkoxy, aryloxy, amino, silyl, aryl, heteroaryl, and combinations thereof, wherein $Y^1$ and $Y^2$ are independently selected from the group consisting of O, S, and Se, wherein n is an integer from 1 to 20, wherein m is an integer from 1 to 20, wherein X and Y are independently selected from the group consisting of O, S, and $NR^{14}$, wherein $R^{11}$ and $R^{14}$ are selected from the group consisting of aryl and heteroaryl;

wherein L is an aryl or heteroaryl group having from 5-30 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof;

wherein B is an all-benzenoid group having at least 24 carbon atoms, which are optionally further substituted with one or more groups selected from hydrogen, deuterium, alkyl, cycloalkyl, arylalkyl, alkoxy, aryloxy, amino, silyl, aryl, and combinations thereof; and wherein (i) the organic layer is a blocking layer and the compound is a blocking material in the organic layer, or (ii) the organic layer is an electron transporting layer and the compound is an electron transporting material in the organic layer.

9. The first device of claim 8, wherein the organic layer is a blocking layer and the compound is a blocking material in the organic layer.

10. The first device of claim 8, wherein the organic layer is an electron transporting layer and the compound is an electron transporting material in the organic layer.

11. The first device of claim 8, wherein the first device is a consumer product selected from the group consisting of flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a wall, theater or stadium screens, or signs.

12. A first device comprising a phosphorescent organic light-emitting device, the phosphorescent organic light-emitting device comprising:

an anode;

a cathode; and an organic layer, disposed between the anode and the cathode, comprising a compound having a structure comprising formula (I):

A-L-B  (I), wherein A is selected from the group consisting of:

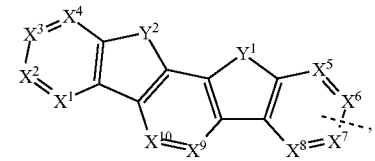

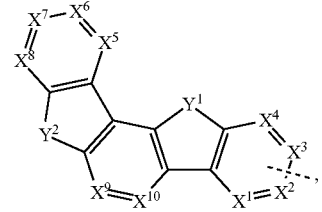

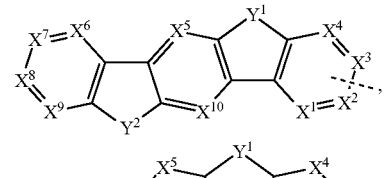

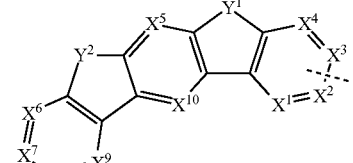

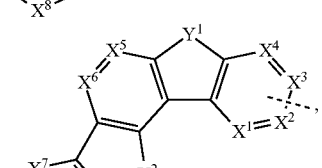

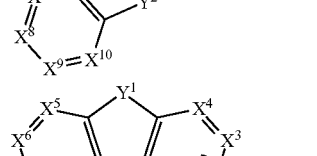
and

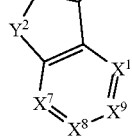

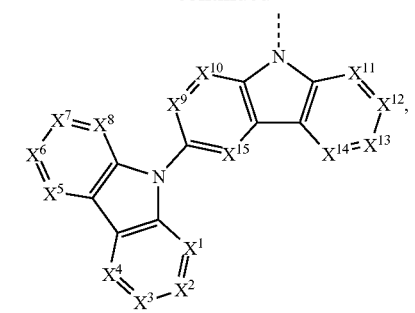

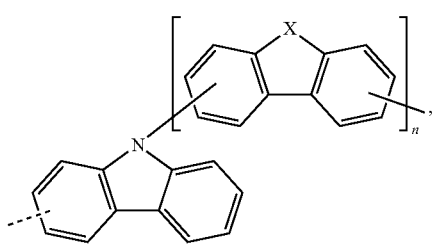

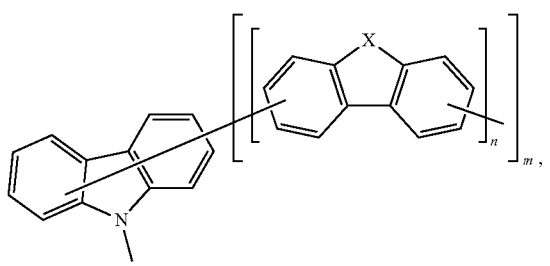

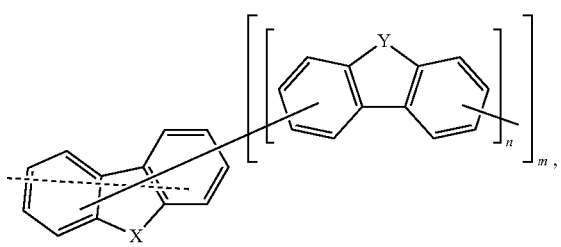

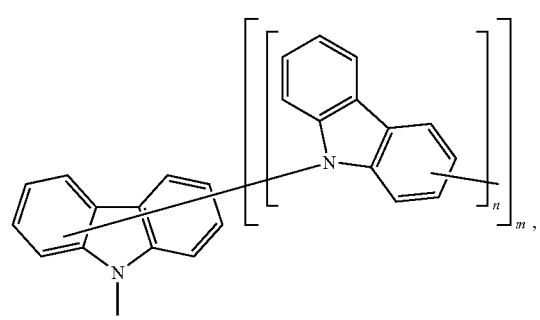

-continued

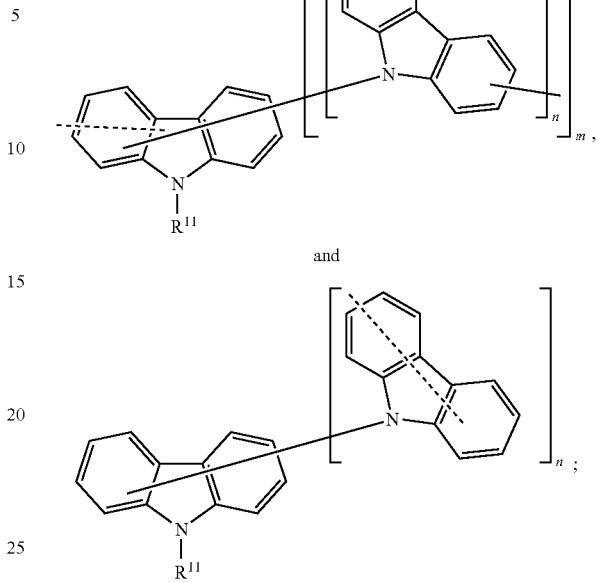

wherein
n is an integer from 1 to 20,
m is an integer from 1 to 20,
X and Y are independently selected from the group consisting of O, S, and NR$^{14}$,
R$^{11}$ and R$^{14}$ are selected from the group consisting of aryl and heteroaryl,
X$^1$-X$^{15}$ are independently selected from the group consisting of N and C—R",
R" is selected from a group consisting of hydrogen, deuterium, alkyl, cycloalkyl, arylalkyl, alkoxy, aryloxy, amino, silyl, aryl, heteroaryl, and combinations thereof; and
Y$^1$ and Y$^2$ are independently selected from the group consisting of O, S, and Se;
wherein L is an aryl or heteroaryl group having from 5-30 carbon atoms, which is optionally further substituted with one or more groups selected from hydrogen, deuterium, alkyl, cycloalkyl, arylalkyl, alkoxy, aryloxy, amino, silyl, aryl, heteroaryl, and combinations thereof; and
wherein B is an all-benzenoid group having at least 24 carbon atoms, which are optionally further substituted with one or more groups selected from hydrogen, deuterium, alkyl, cycloalkyl, arylalkyl, alkoxy, aryloxy, amino, silyl, aryl, and combinations thereof.

13. The first device of claim 12, wherein the organic layer is an emissive layer and the compound of the formula (I) is a host.

14. The first device of claim 12, wherein the organic layer further comprises a phosphorescent emissive dopant.

15. The first device of claim 14, wherein the phosphorescent emissive dopant is a transition metal complex having at least one ligand selected from the group consisting of:

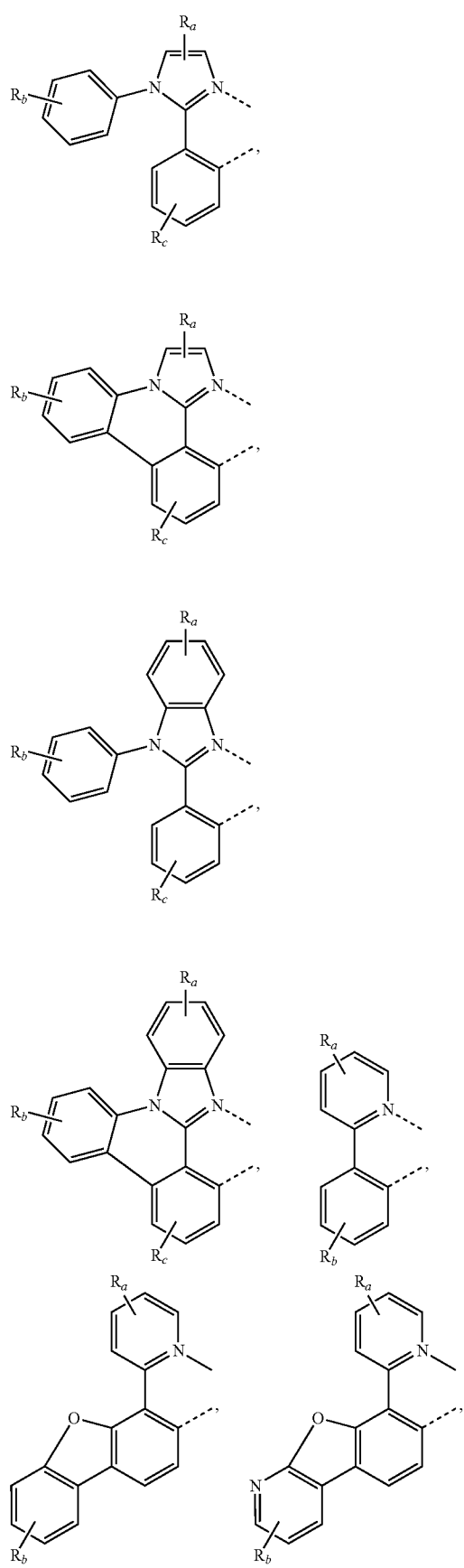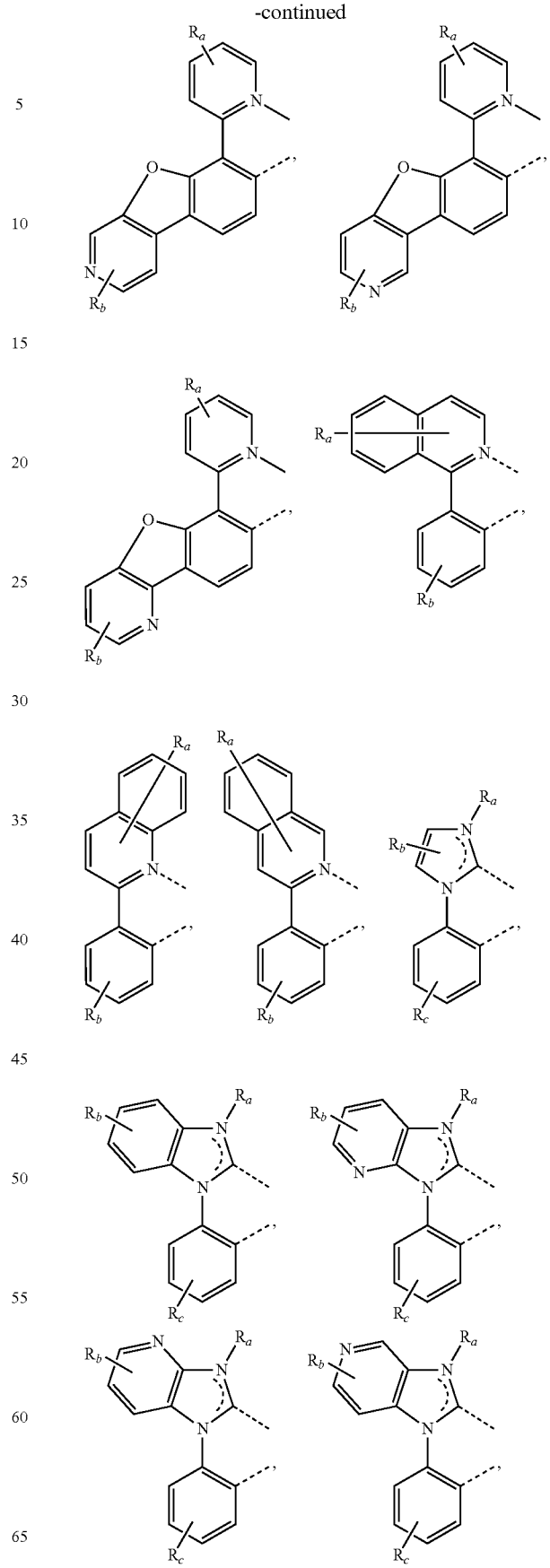

199
-continued

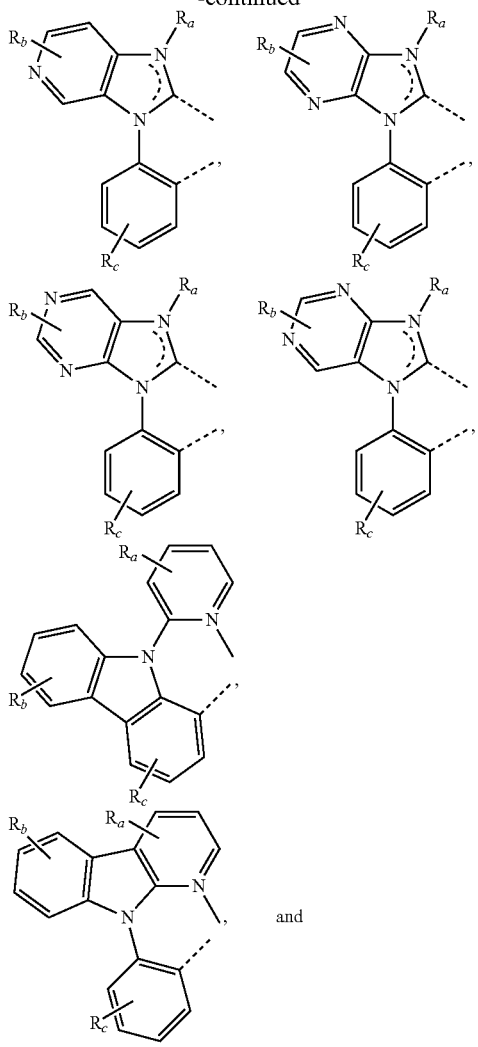

200
-continued

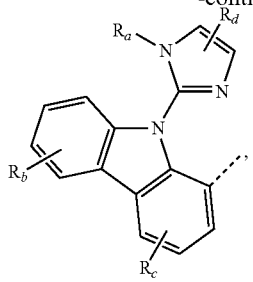

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

16. The first device of claim 12, wherein the first device is a consumer product selected from the group consisting of flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a wall, theater or stadium screens, or signs.

* * * * *

UNITED STATES PATENT AND TRADEMARK OFFICE
CERTIFICATE OF CORRECTION

PATENT NO. : 9,997,712 B2
APPLICATION NO. : 14/186607
DATED : June 12, 2018
INVENTOR(S) : Raymond Kwong, Kit Yee Tsang and Chuanjun Xia Page 1 of 6

It is certified that error appears in the above-identified patent and that said Letters Patent is hereby corrected as shown below:

In the Claims

Column 164, Lines 61-67, please delete the compound

" 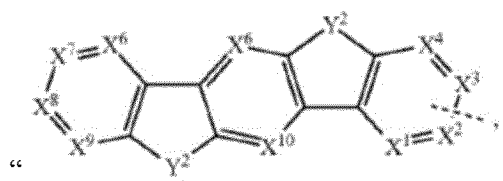 " and insert -- 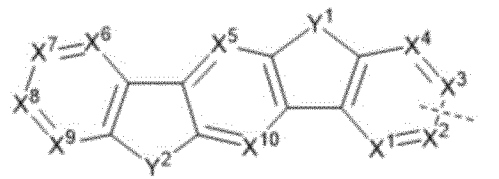 --

Column 165, Lines 3-8, please delete the compound

" 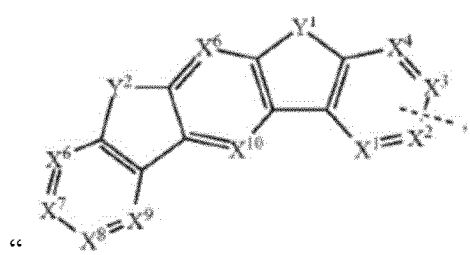 " and insert -- 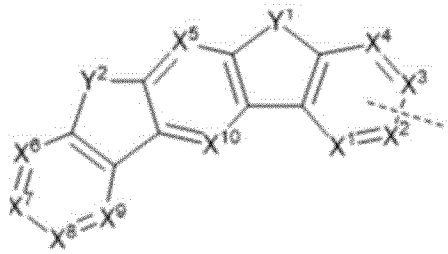 --

Column 165, Lines 48-56, please delete the compound

" 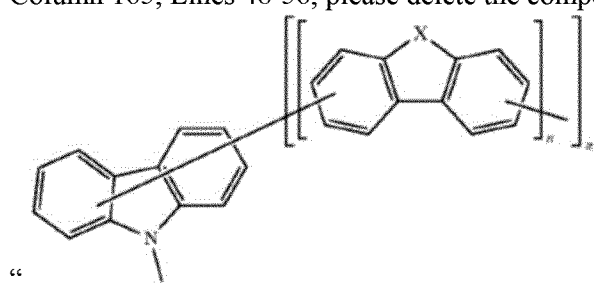 " and

Signed and Sealed this
Ninth Day of October, 2018

Andrei Iancu
*Director of the United States Patent and Trademark Office* insert -- 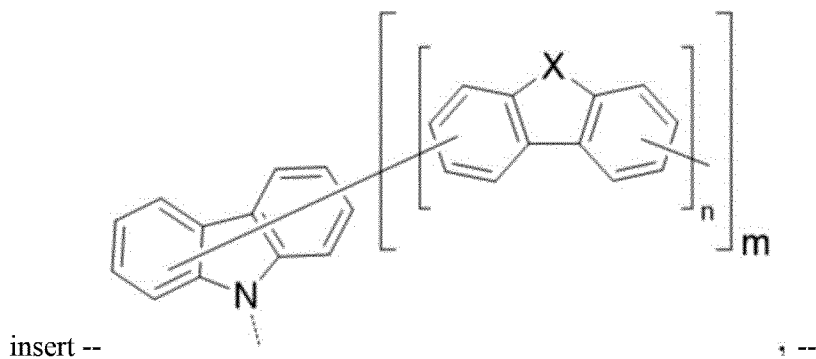 , --
Column 166, Lines 3-16, please delete the compound
" 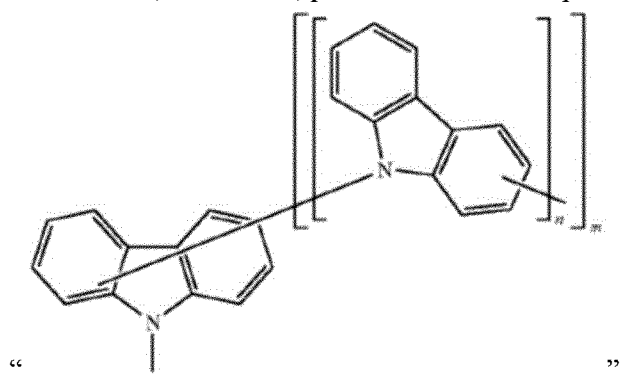 " and
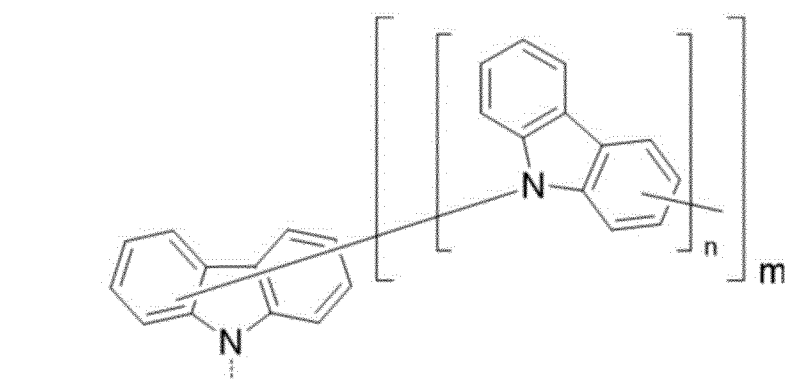
insert -- --
Column 192, Lines 13-22, please delete the compound
" 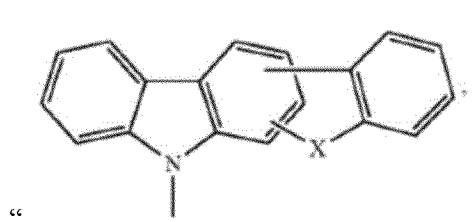 " and insert -- 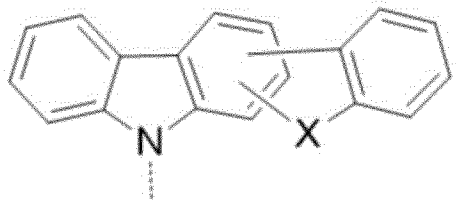 --

Column 192, Lines 28-41, please delete the compound
"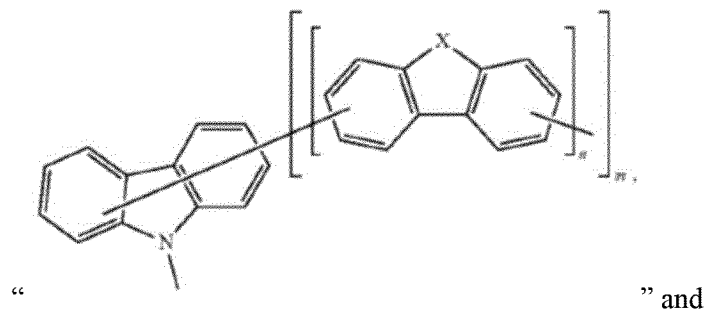" and
insert -- 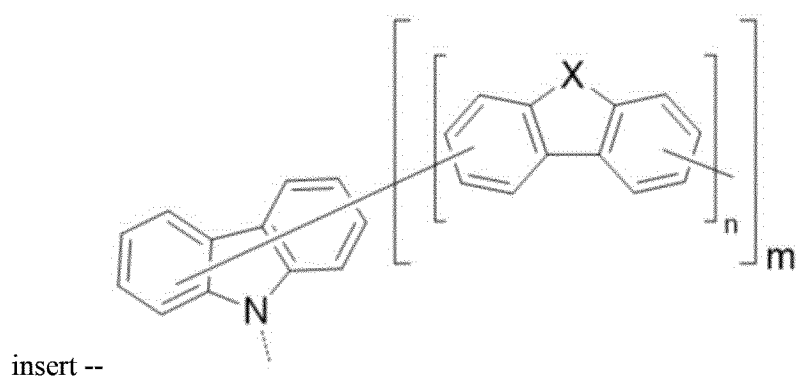 --
Column 192, Lines 55-67, please delete the compound
"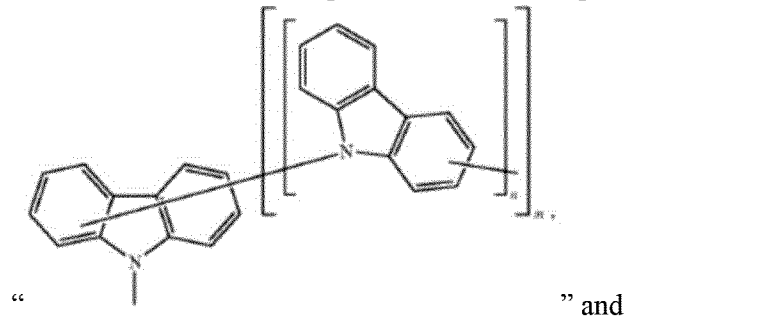" and
insert -- 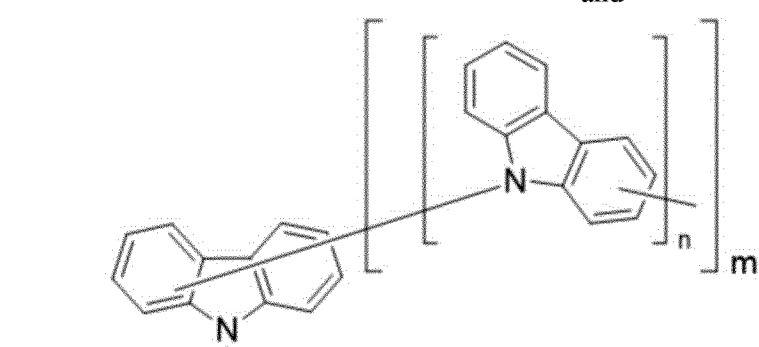 --

Column 195, Lines 28-41, please delete the compound
"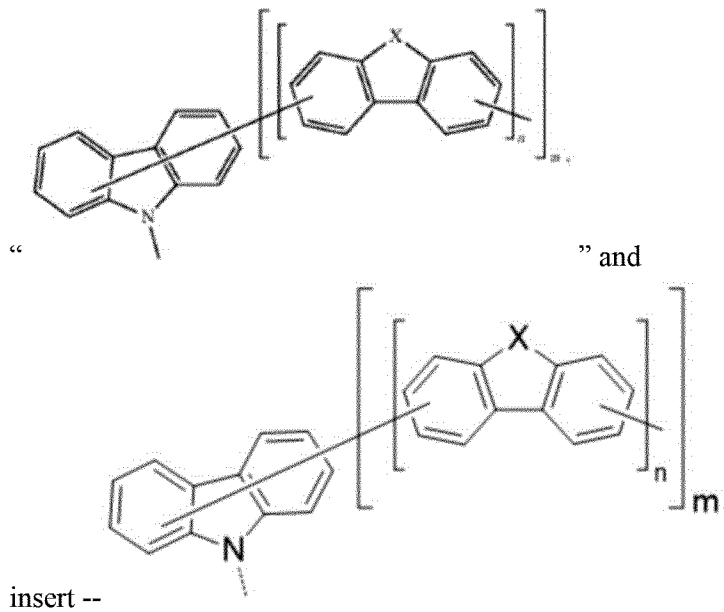" and
insert -- 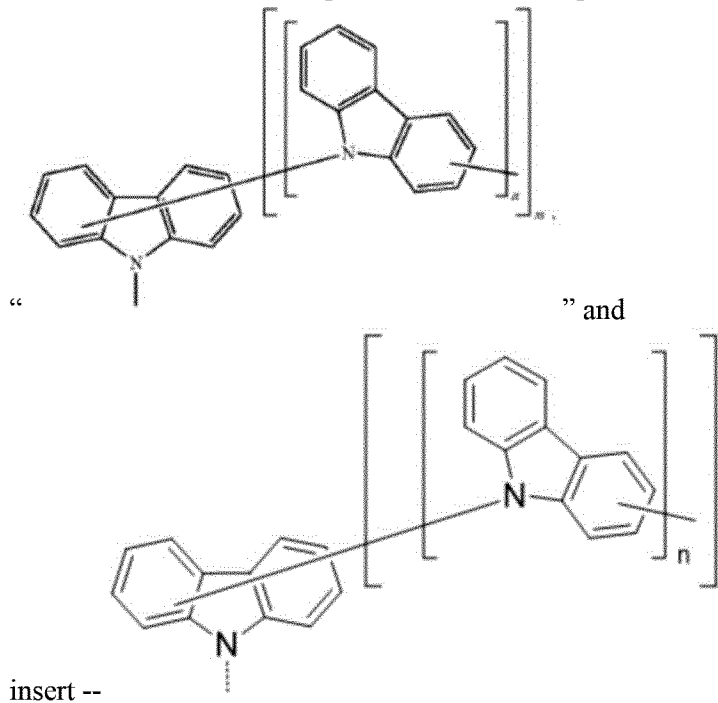 --
Column 195, Lines 55-67, please delete the compound
"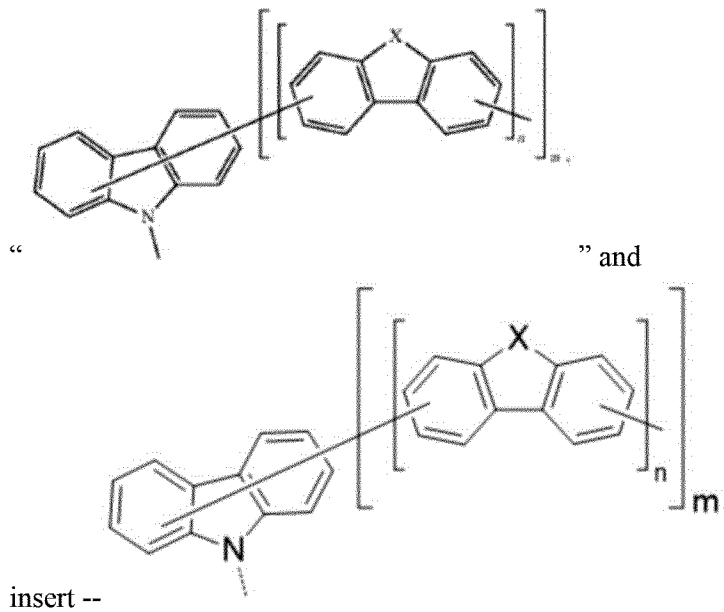" and
insert -- 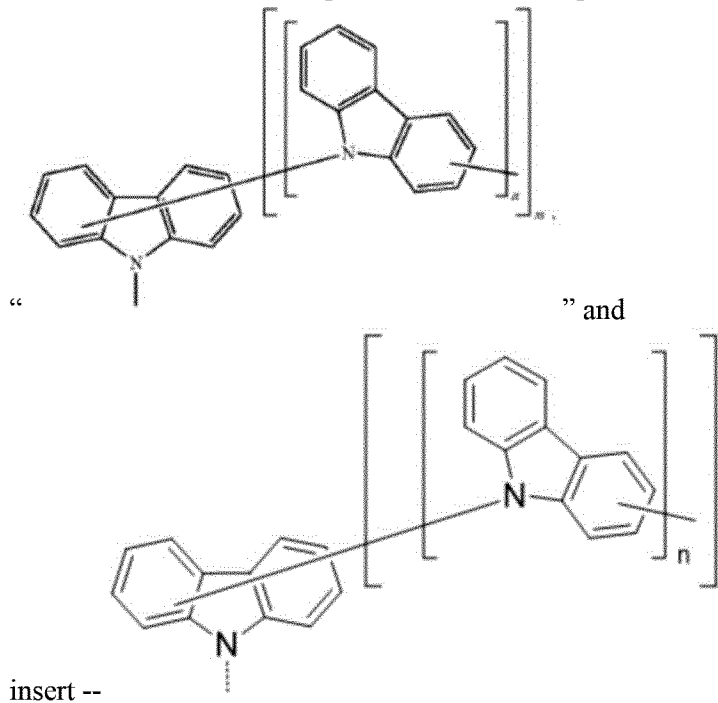 --

CERTIFICATE OF CORRECTION (continued)
U.S. Pat. No. 9,997,712 B2

Column 197, Lines 54-67, please delete the compounds

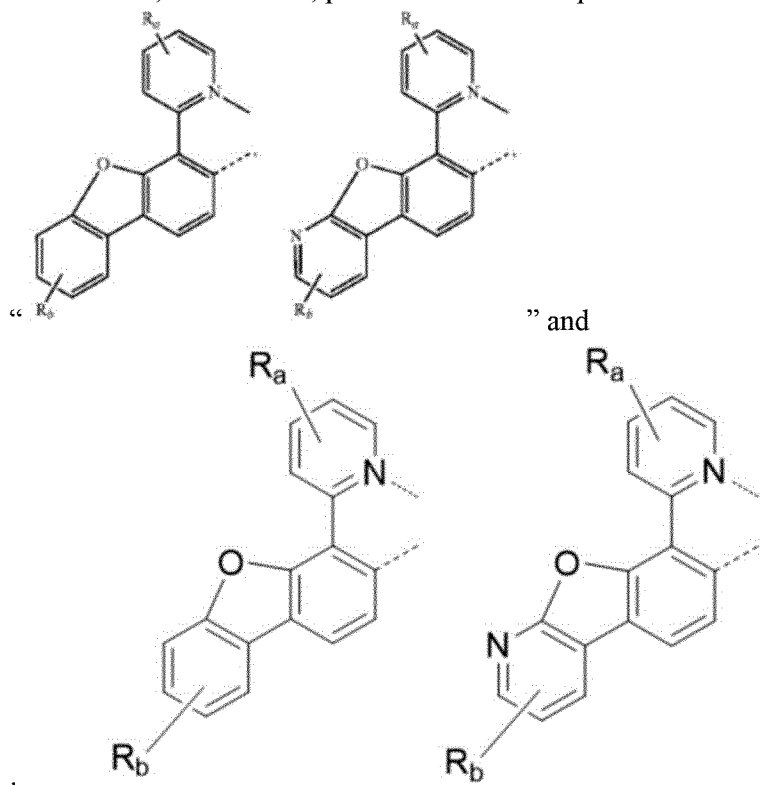

" and insert --

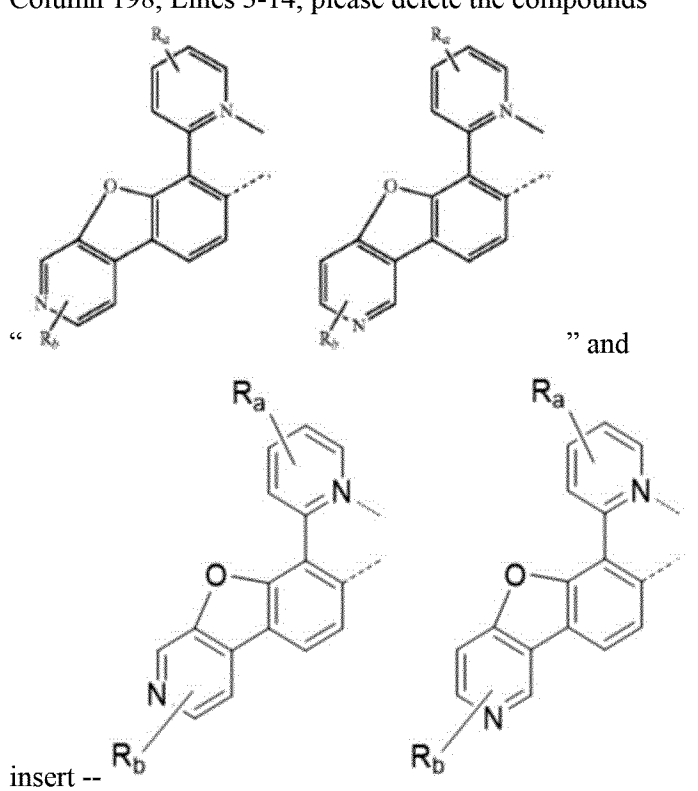

--

Column 198, Lines 3-14, please delete the compounds

" and insert --                                                  --

CERTIFICATE OF CORRECTION (continued)
U.S. Pat. No. 9,997,712 B2

Column 198, Lines 15-31, please delete the compound

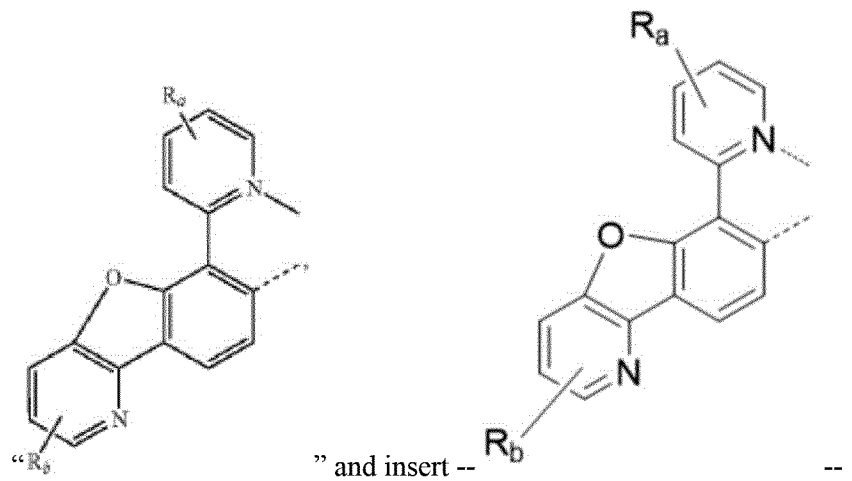

" and insert --

Column 199, Lines 23-31, please delete the compound

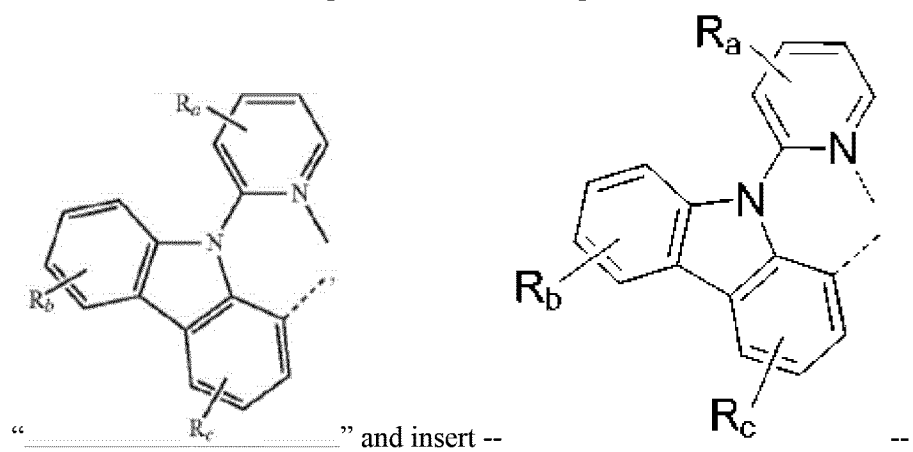

" and insert --

Column 199, Lines 32-40, please delete the compound

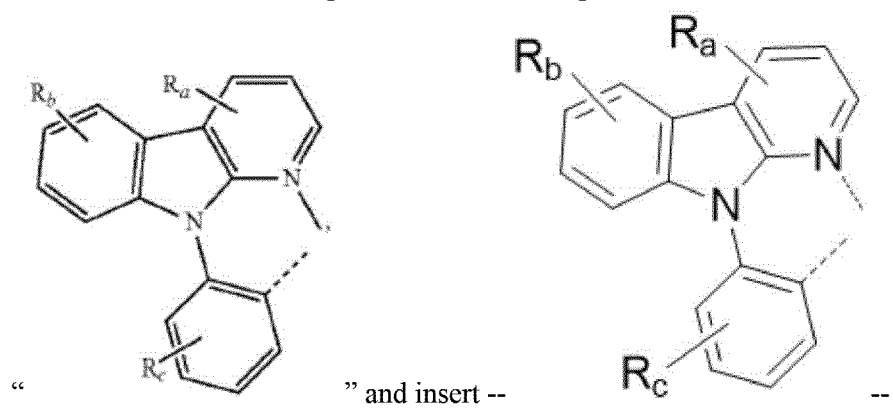

" and insert --